(12) United States Patent
Emptage et al.

(10) Patent No.: US 7,067,300 B2
(45) Date of Patent: Jun. 27, 2006

(54) PROCESS FOR THE BIOLOGICAL PRODUCTION OF 1,3-PROPANEDIOL WITH HIGH TITER

(75) Inventors: Mark Emptage, Wilmington, DE (US); Sharon L. Haynie, Philadelphia, PA (US); Lisa A. Laffend, Claymont, DE (US); Jeff P. Pucci, Pacifica, CA (US); Gregory Marshall Whited, Belmont, CA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 361 days.

(21) Appl. No.: 10/277,249

(22) Filed: Oct. 21, 2002

(65) Prior Publication Data

US 2003/0157674 A1   Aug. 21, 2003

Related U.S. Application Data

(62) Division of application No. 09/641,652, filed on Aug. 18, 2000, now Pat. No. 6,514,733.

(60) Provisional application No. 60/149,534, filed on Aug. 18, 1999.

(51) Int. Cl.
*C12N 1/20* (2006.01)
*C12N 1/14* (2006.01)
*C07H 21/02* (2006.01)

(52) U.S. Cl. .............. 435/252.3; 435/254.11; 435/252.7; 435/252.9; 435/254.3; 435/254.21; 435/254.23; 435/254.8; 435/255.4; 435/252.8; 435/253.5; 435/253.3; 536/23.1; 536/23.2

(58) Field of Classification Search ................ 435/189, 435/252.33, 252.7, 252.9, 254.3, 254.21, 435/254.23, 252.31, 252.8, 252.34, 253.5, 435/254.8, 155; 536/23.2, 23.1
See application file for complete search history.

(56) References Cited

U.S. PATENT DOCUMENTS 5,686,276 A   11/1997   Laffend et al. ............. 435/158
6,013,494 A   1/2000    Nakamura et al. .......... 435/158

FOREIGN PATENT DOCUMENTS

| DE | 3734 764 | 5/1989 |
| EP | 373 230 | 2/1993 |
| WO | WO 9821339 | 5/1998 |
| WO | WO9821341 | 5/1998 |
| WO | WO9928480 | 6/1999 |

OTHER PUBLICATIONS

Daniel et al., FEMS Microbiol. Rev. 22, pp 553-566 Biochemisrty of coenzyme B12-dependent glycerol and diol dehydratases and organization of the encoding genes. (1999).

Toraya and Mori, J. Biol. Chem. vol. 274(6),pp 3372-3377 A reactivating factor for Coenzyme B12-dependent Diol Dehydratase (1999).

GenBank AF026270.

Wang et al., J. Bact., vol. 176(22), pp 7091-7095 Cloning, Sequence, and Disruption of the *Saccharomyces diastaticus* DAR1 Gene Encoding a Glycerol-3-Phosphate Dehydrogenase (1994).

Larason et al., Mol. Microbiol. vol. 10(5), pp, 1101-1111 A gene encoding sn-glycerol 3-phosphate dehydrogenase(NAD+) complements an osmosensitive mutant of *Saccharomyces cerevisiae* (1993).

Albertyn et al., (Mol. Cell. Biol., vol. 14(6),pp 4135-4144 GPD1, Which Encodes Glycerol-3-Phosphate Dehydrogenase, Is Essential for Growth under Osmotic Stress in *Saccharomyces cerevisiae*, and Its Expression Is Regulated by the High-Osmolarity Glycerol Response Pathway, (1994).

Norbeck et al., J. Bio. Chem., vol. 271(23) , pp 13875-13881 Purification and Characterization of Two Isoenzymes of DL-Glycerol-3-phosphatase from *Saccharomyces cerevisiae*. (1996).

Veiga DA Cunha et al., J. Bacteriology,vol. 174(3),pp 1013-1019 Sugar-Glycerol Cofermentations in Lactobacilli: the Fate of Lactate (1992).

Stieb et al., Arch. Microbiol. 140, pp 139-146 A new 3-hydroxybutyrate fermenting anaerobe, Ilyobacter polytropus.gen.nov.sp.nov., possessing various fermentation pathways (1984).

(Continued)

*Primary Examiner*—Rebecca E. Prouty
*Assistant Examiner*—Malgorzata Walicka

(57) ABSTRACT

The present invention provides an improved method for the biological production of 1,3-propanediol from a fermentable carbon source in a single microorganism. In one aspect of the present invention, an improved process for the conversion of glucose to 1,3-propanediol is achieved by the use of an *E. coli* transformed with the *Klebsiella pneumoniae* dha regulon genes dhaR, orfY, dhaT, orfX, orfW, dhaB1, dhaB2, dhaB3, and orfZ, all these genes arranged in the same genetic organization as found in wild type *Klebsiella pneumoniae*. In another aspect of the present invention, an improved process for the production of 1,3-propanediol from glucose using a recombinant *E. coli* containing genes encoding a G3PDH, a G3P phosphatase, a dehydratase, and a dehydratase reactivation factor compared to an identical process using a recombinant *E. coli* containing genes encoding a G3PDH, a G3P phosphatase, a dehydratase, a dehydratase reactivation factor and a 1,3-propanediol oxidoreductase (dhaT). The dramatically improved process relies on the presence in *E. coli* of a gene encoding a non-specific catalytic activity sufficient to convert 3-hydroxypropionaldehyde to 1,3-propanediol.

1 Claim, 6 Drawing Sheets

OTHER PUBLICATIONS

Tong et al., Appl. Biochem. Biotech. vol. 34/35, pp 149-159 Enhancement of 1,3-Propanediol Production by Cofermentation on *Escherichia coli* Expressing Klebsiella pneumoniac dha Regulon Genes (1992).

Tong, Ph.D., Thesis, University of Wisconsin-Madison (1992).

Saint-Amans et al., Biotechnology Ltrs. vol. 16(8), pp 831-836 High Production of 1,3-Propanediol from Glycerol by Clostridium Butyricum VPI 3266 in a simply controlled Fedbatch system (1994).

Abbad-Andaloussi et al., Appl. Environ. Microbiol., vol. 61(12), pp 4413-4417 Isolation and Characterization of Clostridium butyricum DSM 5431 Mutants with Increased Resistance to 1,3-Propanediol and Alered Production of Acids. (1995).

Homann et al., Appl. Bicrobiol., Biotechnol. vol. 33, pp 121-126 Fermentation of glycerol to 1,3-propanediol by Klebsiella and Citrobacter strains. (1990).

Blattner et al. *Escherichia coli* K-12 MG1655 section 273 of 400 of the complete genome XP002162541.

Bouvet et al., Taxonomic diversity of anaerobic glycerol dissimilation in the Enterobacteriaceae, Research in Microbiology vol. 146, No. 4, 1995 pp 279-290 XP000982719.

Skraly et al., Construction and characterization of a 1,3-propanediol operon, Applied and Environmental Microbiology. US, Washington, D.C. vol. 64, No. 1, Jan. 1998 pp 98-105, XP002134649.

SEQUENCE LISTING

<160> NUMBER OF SEQ ID NOS: 68

<210> SEQ ID NO 1
<211> LENGTH: 12145
<212> TYPE: DNA
<213> ORGANISM: Klebsiella pneumoniae

<400> SEQUENCE: 1

```
gtcgaccacc acggtggtga ctttaatgcc gctctcatgc agcagctcgg tggcggtctc      60
aaaattcagg atgtcgccgg tatagttttt gataatcagc aagacgcctt cgccgccgtc     120
aatttgcatc gcgcattcaa acattttgtc cggcgtcggc gaggtgaata tttcccccgg     180
acaggcgccg gagagcatgc cctggccgat atagccgcag tgcatcggtt catgtccgct     240
```

-continued

```
gccgccgccg gagagcaggg ccaccttgcc agccaccggc gcgtcggtgc gggtcacata    300
cagcgggtcc tgatgcaggg tcagctgcgg atgggcttta gccagcccct gtaattgttc    360
attcagtaca tcttcaacac ggttaatcag cttttcatt attcagtgct ccgttggaga     420
aggttcgatg ccgcctctct gctggcggag gcggtcatcg cgtagggta tcgtctgacg     480
gtggagcgtg cctggcgata tgatgattct ggctgagcgg acgaaaaaaa gaatgccccg    540
acgatcgggt tcattacga acattgctt cctgattttg tttctttatg gaacgttttt     600
gctgaggata tggtgaaaat gcgagctggc gcgttttttt tcttctgcca taagcggcgg    660
tcaggatagc cggcgaagcg ggtgggaaaa aattttttgc tgattttctg ccgactgcgg    720
gagaaaaggc ggtcaaacac ggaggattgt aagggcatta tgcggcaaag gagcggatcg    780
ggatcgcaat cctgacagag actaggggttt tttgttccaa tatggaacgt aaaaaattaa    840
cctgtgtttc atatcagaac aaaaaggcga agattttttt tgttccctgc cggccctaca    900
gtgatcgcac tgctccggta cgctccgttc aggccgcgct tcactggccg cgcggataa     960
cgccagggct catcatgtct acatgcgcac ttatttgagg gtgaaaggaa tgctaaaagt   1020
tattcaatct ccagccaaat atcttcaggg tcctgatgct gctgttctgt tcggtcaata   1080
tgccaaaaac ctggcggaga gcttcttcgt catccgctgac gatttcgtaa tgaagctggc   1140
gggagagaaa gtggtgaatg gcctgcagag ccacgatatt cgctgccatg cggaacggtt   1200
taacggcgaa tgcagccatg cggaaatcaa ccgtctgatg gcgattttgc aaaaacaggg   1260
ctgccgcggc gtggtcggga tcggcggtgg taaaaccctc gataccgcga aggcgatcgg   1320
ttactaccag aagctgccgg tggtggtgat cccgaccatc gcctcgaccg atgcgccaac   1380
cagcgcgctg tcggtgatct acaccgaagc gggcgagttt gaagagtatc tgatctatcc   1440
gaaaaacccg gatatggtgg tgatggacac ggcgattatc gccaaagcgc cggtacgcct   1500
gctggtctcc ggcatgggcg atgcgctctc cacctggttc gaggccaaag cttgctacga   1560
tgcgcgcgcc accagcatgg ccggaggaca gtccaccgag gcggcgctga gcctcgcccg   1620
cctgtgctat gatacgctgc tggcggaggg cgaaaaggcc cgtctggcgg cgcaggccgg   1680
ggtagtgacc gaagcgctgg agcgcatcat cgaggcgaac acttacctca gcggcattgg   1740
ctttgaaagc agtggcctgg ccgctgccca tgcaatccac aacggtttca ccattcttga   1800
agagtgccat cacctgtatc acggtgagaa agtggccttc ggtaccctgg cgcagctggt   1860
gctgcagaac agcccgatgg acgagattga acggtgcag ggcttctgcc agcgcgtcgg    1920
cctgccggtg acgctcgcgc agatgggcgt caaagagggg atcgacgaga aaatcgccgc   1980
ggtggcgaaa gctacctgcg cggaagggga accatccat aatatgccgt ttgcggtgac    2040
cccggagagc gtccatgccg ctatcctcac cgccgatctg ttaggccagc agtggctggc   2100
gcgttaattc gcgtggcta aaccgctggc ccaggtcagc ggttttttctt tctcccctcc   2160
ggcagtcgct gccggagggg ttctctatgg tacaacgcgg aaaaggatat gactgttcag   2220
actcaggata ccgggaaggc ggtctcttcc gtcattgccc agtcatggca ccgctgcagc   2280
aagtttatgc agcgcgaaac ctggcaaacg ccgcaccagg cccagggcct gaccttcgac   2340
tccatctgtc ggcgtaaaac cgcgctgctc accatcggcc aggcggcgct ggaagacgcc   2400
tgggagttta tggacggccg cccctgcgcg ctgtttattc ttgatgagtc cgcctgcatc   2460
ctgagccgtt gcggcgagcc gcaaaccctg gcccagctgg ctgccctggg atttcgcgac   2520
ggcagctatt gtgcggagag cattatcggc acctgcgcgc tgtcgctggc cgcgatgcag   2580
```

```
ggccagccga tcaacaccgc cggcgatcgg catttttaagc aggcgctaca gccatggagt   2640
ttttgctcga cgccggtgtt tgataaccac gggcggctgt tcggctctat ctcgctttgc   2700
tgtctggtcg agcaccagtc cagcgccgac ctctccctga cgctggccat cgcccgcgag   2760
gtgggtaact ccctgcttac cgacagcctg ctggcggaat ccaaccgtca cctcaatcag   2820
atgtacggcc tgctggagag catggacgat ggggtgatgg cgtggaacga acagggcgtg   2880
ctgcagtttc tcaatgttca ggcggcgaga ctgctgcatc ttgatgctca ggccagccag   2940
gggaaaaata tcgccgatct ggtgaccctc ccggcgctgc tgcgccgcgc catcaaacac   3000
gcccgcggcc tgaatcacgt cgaagtcacc tttgaaagtc agcatcagtt tgtcgatgcg   3060
gtgatcacct aaaaccgat tgtcgaggcg caaggcaaca gttttattct gctgctgcat    3120
ccggtggagc agatgcggca gctgatgacc agccagctcg gtaaagtcag ccacaccttt   3180
gagcagatgt ctgccgacga tccggaaacc cgacgcctga tccactttgg ccgccaggcg   3240
gcgcgcggcg gcttcccggt gctactgtgc ggcgaagagg gggtcgggaa agagctgctg   3300
agccaggcta ttcacaatga aagcgaacgg gcgggcggcc cctacatctc cgtcaactgc   3360
cagctatatg ccgacagcgt gctgggccag gactttatgg gcagcgcccc taccgacgat   3420
gaaaatggtc gcctgagccg ccttgagctg gccaacggcg gcaccctgtt tctggaaaag   3480
atcgagtatc tggcgccgga gctgcagtcg gctctgctgc aggtgattaa gcagggcgtg   3540
ctcacccgcc tcgacgcccg gcgcctgatc ccggtggatg tgaaggtgat gccaccacc   3600 accgtcgatc tggccaatct ggtggaacag aaccgcttta ccgccagct gtactatgcg   3660 ctgcactcct ttgagatcgt catcccgccg ctgcgcgccc gacgcaacag tattccgtcg   3720
ctggtgcata accggttgaa gagcctggag aagcgtttct cttcgcgact gaaagtggac   3780
gatgacgcgc tggcacagct ggtggcctac tcgtggccgg ggaatgattt tgagctcaac   3840
agcgtcattg agaatatcgc catcagcagc gacaacggcc acattcgcct gagtaatctg   3900
ccggaatatc tcttttccga gcggccgggc ggggatagcg cgtcatcgct gctgccggcc   3960
agcctgactt ttagcgccat cgaaaaggaa gctattattc acgccgcccg ggtgaccagc   4020
gggcgggtgc aggagatgtc gcagctgctc aatatcggcc gcaccaccct gtggcgcaaa   4080
atgaagcagt acgatattga cgccagccag ttcaagcgca agcatcaggc ctagtctctt   4140
cgattcgcgc catggagaac agggcatccg acaggcgatt gctgtagcgt ttgagcgcgt   4200
cgcgcagcgg atgcgcgcgg tccatggccg tcagcaggcg ttcgagccga cgggactggg   4260
tgcgcgccac gtgcagctgg gcagaggcga gattcctccc cgggatcacg aactgtttta   4320
acgggccgct ctcggccata ttgcggtcga taagccgctc cagggcggtg atctcctctt   4380
cgccgatcgt ctggctcagg cgggtcaggc cccgcgcatc gctggccagt tcagccccca   4440
gcacgaacag cgtctgctga atatggtgca ggctttcccg cagcccggcg tcgcgggtcg   4500
tggcgtagca gacgcccagc tgggatatca gttcatcgac ggtgccgtag gcctcgacgc   4560
gaatatggtc tttctcgatg cggctgccgc cgtacagggc ggtggtgcct ttatccccgg   4620
tgcgggtata gatacgatac attcagtttc tctcacttaa cggcaggact ttaaccagct   4680
gcccggcgtt ggcgccgagc gtacgcagtt gatcgtcgct atcggtgacg tgtccggtag   4740
ccagcggcgc gtccgccggc agctgggcat gagtgagggc tatctcgccg gacgcgctga   4800
gcccgatacc cacccgcagg ggcgagcttc tggccgccag ggcgcccagc gcagcggcgt   4860
caccgcctcc gtcataggtt atggtctggc aggggacccc ctgctcctcc agcccccagc   4920
acagctcatt gatggcgccg gcatggtgcc cgcgcggatc gtaaaacagg cgtacgcctg   4980
```

-continued

```
gcggtgaaag cgacatgacg gtcccctcgt taacactcag aatgcctggc ggaaaatcgc    5040
ggcaatctcc tgctcgttgc ctttacgcgg gttcgagaac gcattgccgt cttttagagc    5100
catctccgcc atgtagggga agtcggcctc ttttaccccc agatcgcgca gatgctgcgg    5160
aataccgata tccatcgaca gacgcgtgat agcggcgatg gcttttccg ccgcgtcgag     5220 agtggacagt ccggtgatat tttcgcccat cagttcagcg atatcggcga atttctccgg    5280
gttggcgatc aggttgtagc gcgccacatg cggcagcagg acagcgttgg ccacgccgtg    5340
cggcatgtcg tacaggccgc ccagctggtg cgccatggcg tgcacgtagc cgaggttggc    5400
gttattgaaa gccatcccgg ccagcagaga agcataggcc atgttttccc gcgcctgcag    5460
attgctgccg agggccacgg cctggcgcag gttgcgggcg atgaggcgga tcgcctgcat    5520
ggcggcggcg tccgtcaccg ggttagcgtc tttggagata taggcctcta cggcgtgggt    5580
cagggcatcc atcccggtcg ccgcggtcag ggcggccggt ttaccgatca tcagcagtgg    5640
atcgttgata gagaccgacg gcagtttgcg ccagctgacg atcacaaact tcactttggt    5700
ttcggtgttg gtcaggacgc agtggcgggt gacctcgctg gcggtgccgg cggtggtatt    5760
gaccgcgacg ataggcggca gcgggttggt cagggtctcg attccggcat actggtacag    5820
atcgccctca tgggtggcgg cgatgccgat gcctttgccg caatcgtgcg ggctgccgcc    5880
gcccacggtg acgatgatgt cgcactgttc gcggcgaaac acggcgaggc cgtcgcgcac    5940
gttggtgtct ttcgggttcg gctcgacgcc gtcaaagatc gccacctcga tcccggcctc    6000
ccgcagataa tgcagggttt tgtccaccgc gccatcttta attgcccgca ggcctttgtc    6060
ggtgaccagc agggcttttt tccccccag cagctggcag cgttcgccga ctacggaaat     6120
ggcgttgggg ccaaaaaagt taacgtttgg caccagataa tcaaacatac gatagctcat    6180
aatatacctt ctcgcttcag gttataatgc ggaaaaacaa tccagggcgc actgggctaa    6240
taattgatcc tgctcgaccg taccgccgct aacgccgacg gcgccaatta cctgctcatt    6300
aaaaataact ggcaggccgc cgccaaaaat aataattcgc tgttggttgg ttagctgcag    6360
accgtacaga gattgtcctg gctggaccgc tgacgtaatt tcatgggtac cttgcttcag    6420
gctgcaggcg ctccaggctt tattcaggga aatatcgcag ctggagacga aggcctcgtc    6480
catccgctgg ataagcagcg tgttgcctcc gcggtcaact acggaaaaca ccaccgccac    6540
gttgatctca gtggcttttt tttccaccgc cgccgccatt tgctgggcgg cggccagggt    6600
gattgtctga acttgttggc tcttgttcat cattctctcc cgcaccagga taacgctggc    6660
gcgaatagtc agtaggggc gatagtaaaa aactattacc attcggttgg cttgctttat     6720
ttttgtcagc gttattttgt cgcccgccat gatttagtca ataggttaa aatagcgtcg      6780 gaaaacgta attaagggcg ttttttatta attgatttat atcattgcgg gcgatcacat      6840
tttttatttt tgccgccgga gtaaagtttc atagtgaaac tgtcggtaga tttcgtgtgc    6900
caaattgaaa cgaaattaaa tttatttttt tcaccactgg ctcatttaaa gttccgctat    6960
tgccggtaat ggccgggcgg caacgacgct ggccggcgt attcgctacc gtctgcggat     7020 ttcaccttt gagccgatga acaatgaaa gatcaaaacg atttgcagta ctggcccagc       7080 gcccgtcaa tcaggacggg ctgattggca agtggcctga agaggggctg atcgccatgg     7140 acagccctt tgacccggtc tcttcagtaa aagtggacaa cggtctgatc gtcgaactgg     7200
acggcaaacg ccgggaccag tttgacatga tcgaccgatt tatcgccgat tacgcgatca    7260
acgttgagcg cacagagcag gcaatgcgcc tggaggcggt ggaaatagcc cgtatgctgg    7320
```

```
tggatattca cgtcagccgg gaggagatca ttgccatcac taccgccatc acgccggcca    7380
aagcggtcga ggtgatggcg cagatgaacg tggtggagat gatgatggcg ctgcagaaga    7440
tgcgtgcccg ccggaccccc tccaaccagt gccacgtcac caatctcaaa gataatccgg    7500
tgcagattgc cgctgacgcc gccgaggccg ggatccgcgg cttctcagaa caggagacca    7560
cggtcggtat cgcgcgctac gcgccgttta acgccctggc gctgttggtc ggttcgcagt    7620
gcggccgccc cggcgtgttg acgcagtgct cggtggaaga ggccaccgag ctggagctgg    7680
gcatgcgtgg cttaaccagc tacgccgaga cggtgtcggt ctacggcacc gaagcggtat    7740
ttaccgacgg cgatgatacg ccgtggtcaa aggcgttcct cgcctcggcc tacgcctccc    7800
gcgggttgaa aatgcgctac acctccggca ccggatccga agcgctgatg ggctattcgg    7860
agagcaagtc gatgctctac ctcgaatcgc gctgcatctt cattactaaa ggcgccgggg    7920
ttcagggact gcaaaacggc gcggtgagct gtatcggcat gaccggcgct gtgccgtcgg    7980
gcattcgggc ggtgctggcg gaaaacctga tcgcctctat gctcgacctc gaagtggcgt    8040
ccgccaacga ccagactttc tcccactcgg atattcgccg caccgcgcgc accctgatgc    8100
agatgctgcc gggcaccgac tttatttttct ccggctacag cgcggtgccg aactacgaca    8160
acatgttcgc cggctcgaac ttcgatgcgg aagattttga tgattacaac atcctgcagc    8220
gtgacctgat ggttgacggc ggcctgcgtc cggtgaccga ggcggaaacc attgccattc    8280
gccagaaagc ggcgcgggcg atccaggcgg ttttccgcga gctggggctg ccgccaatcg    8340
ccgacgagga ggtggaggcc gccacctacg cgcacggcag caacgagatg ccgccgcgta    8400
acgtggtgga ggatctgagt gcggtggaag agatgatgaa gcgcaacatc accggcctcg    8460
atattgtcgg cgcgctgagc cgcagcggct ttgaggatat cgccagcaat attctcaata    8520
tgctgcgcca gcgggtcacc ggcgattacc tgcagacctc ggccattctc gatcggcagt    8580
tcgaggtggt gagtgcggtc aacgacatca atgactatca ggggccgggc accggctatc    8640
gcatctctgc cgaacgctgg gcggagatca aaaatattcc gggcgtggtt cagcccgaca    8700
ccattgaata aggcggtatt cctgtgcaac agacaaccca aattcagccc tcttttaccc    8760 tgaaacccg cgagggcggg gtagcttctg ccgatgaacg cgccgatgaa gtggtgatcg    8820
gcgtcggccc tgccttcgat aaacaccagc atcacactct gatcgatatg ccccatggcg    8880
cgatcctcaa agagctgatt gccggggtgg aagaagaggg gcttcacgcc cggtggtgc    8940 gcattctgcg cacgtccgac gtctccttta tggcctggga tgcggccaac ctgagcggct    9000
cggggatcgg catcggtatc cagtcgaagg ggaccacggt catccatcag cgcgatctgc    9060
tgccgctcag caacctggag ctgttctccc aggcgccgct gctgacgctg agacctacc    9120 ggcagattgg caaaaacgct gcgcgctatg cgcgcaaaga gtcaccttcg ccggtgccgg    9180
tggtgaacga tcagatggtg cggccgaaat ttatggccaa agccgcgcta tttcatatca    9240
aagagaccaa acatgtggtg caggacgccg agcccgtcac cctgcacatc gacttagtaa    9300
gggagtgacc atgagcgaga aaaccatgcg cgtgcaggat tatccgttag ccacccgctg    9360 cccgagcat atcctgacgc ctaccggcaa accattgacc gatattaccc tcgagaaggt    9420
gctctctggc gaggtgggcc cgcaggatgt gcggatctcc cgccagaccc ttgagtacca    9480
ggcgcagatt gccgagcaga tgcagcgcca tgcggtggcg cgcaatttcc gccgcgcggc    9540
ggagcttatc gccattcctg acgagcgcat tctggctatc tataacgcgc tgcgcccgtt    9600
ccgctcctcg caggcggagc tgctggcgat cgccgacgag ctggagcaca cctggcatgc    9660
gacagtgaat gccgccttg tccgggagtc ggcggaagtg tatcagcagc ggcataagct    9720
```

-continued

```
gcgtaaagga agctaagcgg aggtcagcat gccgttaata gccgggattg atatcggcaa    9780
cgccaccacc gaggtggcgc tggcgtccga ctacccgcag gcgagggcgt ttgttgccag    9840
cgggatcgtc gcgacgacgg gcatgaaagg gacgcgggac aatatcgccg ggaccctcgc    9900
cgcgctggag caggccctgg cgaaaacacc gtggtcgatg agcgatgtct ctcgcatcta    9960
tcttaacgaa gccgcgccgg tgattggcga tgtggcgatg gagaccatca ccgagaccat   10020
tatcaccgaa tcgaccatga tcggtcataa cccgcagacg ccgggcgggg tgggcgttgg   10080
cgtggggacg actatcgccc tcgggcggct ggcgacgctg ccggcggcgc agtatgccga   10140
ggggtggatc gtactgattg acgacgccgt cgatttcctt gacgccgtgt ggtggctcaa   10200
tgaggcgctc gaccggggga tcaacgtggt ggcggcgatc ctcaaaaagg acgacggcgt   10260
gctggtgaac aaccgcctgc gtaaaaccct gccggtggtg gatgaagtga cgctgctgga   10320
gcaggtcccc gagggggtaa tggcggcggt ggaagtggcc gcgccgggcc aggtggtgcg   10380
gatcctgtcg aatccctacg ggatcgccac cttcttcggg ctaagcccgg aagagaccca   10440
ggccatcgtc cccatcgccc gcgccctgat tggcaaccgt tccgcggtgg tgctcaagac   10500
cccgcagggg gatgtgcagt cgcgggtgat cccggcgggc aacctctaca ttagcggcga   10560
aaagcgccgc ggagaggccg atgtcgccga gggcgcggaa gccatcatgc aggcgatgag   10620
cgcctgcgct ccggtacgcg acatccgcgg cgaaccgggc acccacgccg gcggcatgct   10680
tgagcgggtg cgcaaggtaa tggcgtccct gaccggccat gagatgagcg cgatatacat   10740
ccaggatctg ctggcggtgg atacgtttat tccgcgcaag gtgcagggcg ggatggccgg   10800
cgagtgcgcc atggagaatg ccgtcgggat ggcggcgatg gtgaaagcgg atcgtctgca   10860
aatgcaggtt atcgcccgcg aactgagcgc ccgactgcag accgaggtgg tggtgggcgg   10920
cgtggaggcc aacatggcca tcgccggggc gttaaccact cccggctgtg cggcgccgct   10980
ggcgatcctc gacctcggcg ccggctcgac ggatgcggcg atcgtcaacg cggagggggca   11040 gataacggcg gtccatctcg ccggggcggg gaatatggtc agcctgttga ttaaaaccga   11100
gctgggcctc gaggatcttt cgctggcgga agcgataaaa aaatacccgc tggccaaagt   11160
ggaaagcctg ttcagtattc gtcacgagaa tggcgcggtg gagttctttc gggaagccct   11220
cagcccggcg gtgttcgcca agtggtgta catcaaggag ggcgaactgg tgccgatcga   11280
taacgccagc ccgctggaaa aaattcgtct cgtgcgccgg caggcgaaag agaaagtgtt   11340
tgtcaccaac tgcctgcgcg cgctgcgcca ggtctcaccc ggcggttcca ttcgcgatat   11400
cgcctttgtg gtgctggtgg gcggctcatc gctggacttt gagatcccgc agcttatcac   11460
ggaagccttg tcgcactatg gcgtggtcgc cgggcagggc aatattcggg gaacagaagg   11520
gccgcgcaat gcggtcgcca ccgggctgct actggccggt caggcgaatt aaacgggcgc   11580
tcgcgccagc ctctctcttt aacgtgctat ttcaggatgc cgataatgaa ccagacttct   11640
accttaaccg ggcagtgcgt ggccgagttt cttggcaccg gattgctcat tttcttcggc   11700
gcgggctgcg tcgctgcgct gcgggtcgcc ggggccagct ttggtcagtg ggagatcagt   11760
attatctggg gccttggcgt cgccatggcc atctacctga cggccggtgt ctccggcgcg   11820
cacctaaatc cggcggtgac cattgccctg tggctgttcg cctgttttga acgccgcaag   11880
gtgctgccgt ttattgttgc ccagacggcc ggggccttct cgccgccgcg ctggtgtat    11940 gggctctatc gccagctgtt tctcgatctt gaacagagtc agcatatcgt gcgcggcact   12000
gccgccagtc ttaacctggc cggggtcttt tccacgtacc cgcatccaca tatcactttt   12060
```

```
atacaagcgt tgccgtgga gaccaccatc acggcaatcc tgatggcgat gatcatggcc    12120
ctgaccgacg acggcaacgg aattc                                          12145

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gctttctgtg ctgcggcttt ag                                             22

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
tggtcgagga tccacttcac ttt                                            23

<210> SEQ ID NO 4
<211> LENGTH: 51
<212> TYPE: DNA
<213> ORGANISM: Artificial Sequence
<220> FEATURE:
<223> OTHER INFORMATION: Primer

<400> SEQUENCE: 4
aaagtgaagt ggatcctcga ccaattggat ggtggcgcag tagcaaacaa t             51

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ggatcaccgc cgcagaaact acg                                            23

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
ctgtcagccg ttaagtgttc ctgtg                                          25

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cagttcaacc tgttgatagt acg                                            23

<210> SEQ ID NO 8
<211> LENGTH: 20
```

<212> TYPE: DNA
<213> ORGANISM: Artificial Sequence
<220> FEATURE:
<223> OTHER INFORMATION: Primer

<400> SEQUENCE: 8
atgagtcaaa catcaacctt                                           20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atggagaaaa aaatcactgg                                           20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ttacgccccg ccctgccact                                           20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcagaggatg tgcacctgca                                           20

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
cgagcatgcc gcatttggca ctactc                                    26

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
gcgtctagag taggttattc ccactcttg                                 29

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
gaagtcgacc gctgcgcctt atccgg                                              26

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
cgcgtcgacg tttacaattt caggtggc                                            28

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
gcagcatgct ggactggtag tag                                                 23

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
cagtctagag ttattggcaa acctacc                                             27

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gatgcatgcc cagggcggag acggc                                               25

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
ctaacgattg ttctctagag aaaatgtcc                                           29

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
cacgcatgca gttcaacctg ttgatagtac                                          30

<210> SEQ ID NO 21
<211> LENGTH: 28
<212> TYPE: DNA
<213> ORGANISM: Artificial Sequence

```
<220> FEATURE:
<223> OTHER INFORMATION: Primer

<400> SEQUENCE: 21
gcgtctagat ccttttaaat taaaaatg                                            28

<210> SEQ ID NO 22
<211> LENGTH: 51
<212> TYPE: DNA
<213> ORGANISM: Artificial Sequence
<220> FEATURE:
<223> OTHER INFORMATION: Primer

<400> SEQUENCE: 22
gcgcggatcc aggagtctag aattatggga ttgactacta aacctctatc t                  51

<210> SEQ ID NO 23
<211> LENGTH: 36
<212> TYPE: DNA
<213> ORGANISM: Artificial Sequence
<220> FEATURE:
<223> OTHER INFORMATION: Primer

<400> SEQUENCE: 23
gatacgcccg ggttaccatt tcaacagatc gtcctt                                   36

<210> SEQ ID NO 24
<211> LENGTH: 34
<212> TYPE: DNA
<213> ORGANISM: Artificial Sequence
<220> FEATURE:
<223> OTHER INFORMATION: Primer

<400> SEQUENCE: 24
ttgataatat aaccatggct gctgctgctg atag                                     34

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
gtatgatatg ttatcttgga tccaataaat ctaatcttc                                39

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
catgactagt aaggaggaca attc                                                24

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
catggaattg tcctccttac tagt                                                24
```

-continued

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
ctagtaagga ggacaattc                                             19

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
catggaattg tcctcctta                                             19

<210> SEQ ID NO 30
<211> LENGTH: 15
<212> TYPE: DNA
<213> ORGANISM: Artificial Sequence
<220> FEATURE:
<223> OTHER INFORMATION: Primer

<400> SEQUENCE: 30
gatccaggaa acaga                                                 15

<210> SEQ ID NO 31
<211> LENGTH: 15
<212> TYPE: DNA
<213> ORGANISM: Artificial Sequence
<220> FEATURE:
<223> OTHER INFORMATION: Primer

<400> SEQUENCE: 31
ctagtctgtt tcctg                                                 15

<210> SEQ ID NO 32
<211> LENGTH: 94
<212> TYPE: DNA
<213> ORGANISM: Artificial Sequence
<220> FEATURE:
<223> OTHER INFORMATION: Terminator sequence

<400> SEQUENCE: 32
agcttaggag tctagaatat tgagctcgaa ttcccgggca tgcggtaccg gatccagaaa    60
aaagcccgca cctgacagtg cgggcttttt tttt                                94

<210> SEQ ID NO 33
<211> LENGTH: 37
<212> TYPE: DNA
<213> ORGANISM: Artificial Sequence
<220> FEATURE:
<223> OTHER INFORMATION: Primer

<400> SEQUENCE: 33
ggaattcaga tctcagcaat gagcgagaaa accatgc                          37

<210> SEQ ID NO 34
<211> LENGTH: 27
<212> TYPE: DNA
<213> ORGANISM: Artificial Sequence

```
<220> FEATURE:
<223> OTHER INFORMATION: Primer

<400> SEQUENCE: 34
gctctagatt agcttccttt acgcagc                                          27

<210> SEQ ID NO 35
<211> LENGTH: 33
<212> TYPE: DNA
<213> ORGANISM: Artificial Sequence
<220> FEATURE:
<223> OTHER INFORMATION: Primer

<400> SEQUENCE: 35
ggccaagctt aaggaggtta attaaatgaa aag                                   33

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
gctctagatt attcaatggt gtcggg                                           26

<210> SEQ ID NO 37
<211> LENGTH: 42
<212> TYPE: DNA
<213> ORGANISM: Artificial Sequence
<220> FEATURE:
<223> OTHER INFORMATION: Primer

<400> SEQUENCE: 37
gcgccgtcta gaattatgag ctatcgtatg tttgattatc tg                         42

<210> SEQ ID NO 38
<211> LENGTH: 36
<212> TYPE: DNA
<213> ORGANISM: Artificial Sequence
<220> FEATURE:
<223> OTHER INFORMATION: Primer

<400> SEQUENCE: 38
tctgatacgg gatcctcaga atgcctggcg gaaaat                                36

<210> SEQ ID NO 39
<211> LENGTH: 18
<212> TYPE: DNA
<213> ORGANISM: Artificial Sequence
<220> FEATURE:
<223> OTHER INFORMATION: Linker

<400> SEQUENCE: 39
tcgacgaatt caggagga                                                    18

<210> SEQ ID NO 40
<211> LENGTH: 18
<212> TYPE: DNA
<213> ORGANISM: Artificial Sequence
<220> FEATURE:
<223> OTHER INFORMATION: Linker

<400> SEQUENCE: 40
ctagtcctcc tgaattcg                                                    18
```

<210> SEQ ID NO 41
<211> LENGTH: 4549
<212> TYPE: DNA
<213> ORGANISM: Artificial Sequence
<220> FEATURE:
<223> OTHER INFORMATION: plasmid pCL1920

<400> SEQUENCE: 41

```
agctcgtcag cgggtgttgg cgggtgtcgg ggctggctta actatgcggc atcagagcag      60
attgtactga gagtgcacca tatgcggtgt gaaataccgc acagatgcgt aaggagaaaa     120
taccgcatca ggcgccattc gccattcagg ctgcgcaact gttgggaagg gcgatcggtg     180
cgggcctctt cgctattacg ccagctggcg aaagggggat gtgctgcaag gcgattaagt     240
tgggtaacgc caggggtttttc ccagtcacga cgttgtaaaa cgacggccag tgaattcgag     300
ctcggtaccc ggggatcctc tagagtcgac ctgcaggcat gcaagcttgg cgtaatcatg     360
gtcatagctg tttcctgtgt gaaattgtta tccgctcaca attccacaca acatacgagc     420
cggaagcata aagtgtaaag cctggggtgc ctaatgagtg agctaactca cattaattgc     480
gttgcgctca ctgcccgctt tccagtcggg aaacctgtcg tgccagctgc attaatgaat     540
cggccaacgc gaattcccga cagtaagacg ggtaagcctg ttgatgatac cgctgcctta     600
ctgggtgcat tagccagtct gaatgacctg tcacggggata atccgaagtg gtcagactgg     660
aaaatcagag ggcaggaact gctgaacagc aaaaagtcag atagcaccac atagcagacc     720
cgccataaaa cgccctgaga agcccgtgac gggcttttct tgtattatgg gtagtttcct     780
tgcatgaatc cataaaaggc gcctgtagtg ccatttaccc ccattcactg ccagagccgt     840
gagcgcagcg aactgaatgt cacgaaaaag acagcgactc aggtgcctga tggtcggaga     900
caaaaggaat attcagcgat ttgcccgagc ttgcgagggt gctacttaag cctttagggt     960
tttaaggtct gttttgtaga ggagcaaaca gcgtttgcga catccttttg taatactgcg    1020
gaactgacta aagtagtgag ttatacacag ggctgggatc tattcttttt atctttttttt    1080
attctttctt tattctataa attataacca cttgaatata aacaaaaaaa acacacaaag    1140
gtctagcgga atttacagag ggtctagcag aatttacaag ttttccagca aaggtctagc    1200
agaatttaca gatacccaca actcaaagga aaaggactag taattatcat tgactagccc    1260
atctcaattg gtatagtgat aaaatcacc tagaccaatt gagatgtatg tctgaattag    1320
ttgttttcaa agcaaatgaa ctagcgatta gtcgctatga cttaacggag catgaaacca    1380
agctaatttt atgctgtgtg gcactactca accccacgat tgaaaaccct acaaggaaag    1440
aacggacggt atcgttcact tataaccaat acgctcagat gatgaacatc agtagggaaa    1500
atgcttatgg tgtattagct aaagcaacca gagagctgat gacgagaact gtggaaatca    1560
ggaatccttt ggttaaaggc tttgagattt tccagtggac aaactatgcc aagttctcaa    1620
gcgaaaaatt agaattagtt tttagtgaag agatattgcc ttatcttttc cagttaaaaa    1680
aattcataaa atataatctg gaacatgtta agtcttttga aacaaatac tctatgagga    1740
tttatgagtg gttattaaaa gaactaacac aaaagaaaac tcacaaggca aatatagaga    1800
ttagccttga tgaatttaag ttcatgttaa tgcttgaaaa taactaccat gagtttaaaa    1860
ggcttaacca atgggttttg aaaccaataa gtaaagattt aaacacttac agcaatatga    1920
aattggtggt tgataagcga ggccgcccga ctgatacgtt gattttccaa gttgaactag    1980
atagacaaat ggatctcgta accgaacttg agaacaacca gataaaaatg aatggtgaca    2040
aataccaac aaccattaca tcagattcct acctacataa cggactaaga aaaacactac    2100
```

```
acgatgcttt aactgcaaaa attcagctca ccagttttga ggcaaaattt ttgagtgaca    2160
tgcaaagtaa gtatgatctc aatggttcgt tctcatggct cacgcaaaaa caacgaacca    2220
cactagagaa catactggct aaatacggaa ggatctgagg ttcttatggc tcttgtatct    2280
atcagtgaag catcaagact aacaaacaaa agtagaacaa ctgttcaccg ttacatatca    2340
aagggaaaac tgtccatatg cacagatgaa aacggtgtaa aaaagataga tacatcagag    2400
cttttacgag tttttggtgc attcaaagct gttcaccatg aacagatcga caatgtaaca    2460
gatgaacagc atgtaacacc taatagaaca ggtgaaacca gtaaaacaaa gcaactagaa    2520
catgaaattg aacacctgag acaacttgtt acagctcaac agtcacacat agacagcctg    2580
aaacaggcga tgctgcttat cgaatcaaag ctgccgacaa cacgggagcc agtgacgcct    2640
cccgtgggga aaaatcatg gcaattctgg aagaaatagc gctttcagcc ggcaaaccgg     2700
ctgaagccgg atctgcgatt ctgataacaa actagcaaca ccagaacagc ccgtttgcgg    2760
gcagcaaaac ccgtgggaat taattcccct gctcgcgcag gctgggtgcc aagctctcgg    2820
gtaacatcaa ggcccgatcc ttggagccct tgccctcccg cacgatgatc gtgccgtgat    2880
cgaaatccag atccttgacc cgcagttgca aaccctcact gatccgcatg cccgttccat    2940
acagaagctg ggcgaacaaa cgatgctcgc cttccagaaa accgaggatg cgaaccactt    3000
catccggggt cagcaccacc ggcaagcgcc gcgacggccg aggtcttccg atctcctgaa    3060 gccaggcag atccgtgcac agcaccttgc cgtagaagaa cagcaaggcc gccaatgcct     3120
gacgatgcgt ggagaccgaa accttgcgct cgttcgccag ccaggacaga aatgcctcga    3180
cttcgctgct gcccaaggtt gccgggtgac gcacaccgtg gaaacggatg aaggcacgaa    3240
cccagtggac ataagcctgt tcggttcgta agctgtaatg caagtagcgt atgcgctcac    3300
gcaactggtc cagaaccttg accgaacgca gcggtggtaa cggcgcagtg gcggttttca    3360
tggcttgtta tgactgtttt tttgggggtac agtctatgcc tcgggcatcc aagcagcaag   3420
cgcgttacgc cgtgggtcga tgtttgatgt tatggagcag caacgatgtt acgcagcagg    3480
gcagtcgccc taaaacaaag ttaaacatca tgagggaagc ggtgatcgcc gaagtatcga    3540
ctcaactatc agaggtagtt ggcgtcatcg agcgccatct cgaaccgacg ttgctggccg    3600
tacatttgta cggctccgca gtggatggcg gcctgaagcc acacagtgat attgatttgc    3660
tggttacggt gaccgtaagg cttgatgaaa caacgcggcg agctttgatc aacgaccttt    3720
tggaaacttc ggcttcccct ggagagagcg agattctccg cgctgtagaa gtcaccattg    3780
ttgtgcacga cgacatcatt ccgtggcgtt atccagctaa gcgcgaactg caatttggag    3840
aatggcagcg caatgacatt cttgcaggta tcttcgagcc agccacgatc gacattgatc    3900
tggctatctt gctgacaaaa gcaagagaac atagcgttgc cttggtaggt ccagcggcgg    3960
aggaactctt tgatccggtt cctgaacagg atctatttga ggcgctaaat gaaaccttaa    4020
cgctatggaa ctcgccgccc gactgggctg gcgatgagcg aaatgtagtg cttacgttgt    4080
cccgcatttg gtacagcgca gtaaccggca aaatcgcgcc gaaggatgtc gctgccgact    4140
gggcaatgga gcgcctgccg gcccagtatc agcccgtcat acttgaagct agacaggctt    4200
atcttggaca agaagaagat cgcttggcct cgcgcgcaga tcagttggaa gaatttgtcc    4260
actacgtgaa aggcgagatc accaaggtag tcggcaaata atgtctaaca attcgttcaa    4320
gccgacgccg cttcgcggcg cggcttaact caagcgttag atgcactaag cacataattg    4380
ctcacagcca aactatcagg tcaagtctgc ttttattatt tttaagcgtg cataataagc    4440
```

-continued cctacacaaa ttgggagata tatcatgaaa ggctggcttt ttcttgttat cgcaatagtt    4500
ggcgaagtaa tcgcaacatc cgcattaaaa tctagcgagg gctttacta               4549

<210> SEQ ID NO 42
<211> LENGTH: 199
<212> TYPE: DNA
<213> ORGANISM: Artificial Sequence
<220> FEATURE:
<223> OTHER INFORMATION: glucose isomerase promoter

<400> SEQUENCE: 42
gaattcacta gtcgatctgt gctgtttgcc acgtatgca gcaccagcgc gagattatgg     60
gctcgcacgc tcgactgtcg gacggggca ctggaacgag aagtcaggcg agccgtcacg    120
cccttgacaa tgccacatcc tgagcaaata attcaaccac taaacaaatc aaccgcgttt    180
cccggaggta accaagctt                                                199

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
gacgcaacag tattccgtcg c                                              21

<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44
atgagctatc gtatgttccg ccaggcattc tgagtgttaa cg                       42

<210> SEQ ID NO 45
<211> LENGTH: 33
<212> TYPE: DNA
<213> ORGANISM: Artificial Sequence
<220> FEATURE:
<223> OTHER INFORMATION: Primer

<400> SEQUENCE: 45
gcctggcgga acatacgata gctcataata tac                                 33

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
cggggcgctg ggccagtact g                                              21

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47

```
tcaaacccgg tggtttctcg cgaccggg                                28

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
ctcagccgga tatcgacggc gcgctggt                                28

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49
accagcgcgc cgtcgatatc cggctgagta ctcaacacct gccagctctt tacgcaggtt     60

<210> SEQ ID NO 50
<211> LENGTH: 28
<212> TYPE: DNA
<213> ORGANISM: Artificial Sequence
<220> FEATURE:
<223> OTHER INFORMATION: Primer

<400> SEQUENCE: 50
cagcatgcct gcgaaccaca ggcctatc                                28

<210> SEQ ID NO 51
<211> LENGTH: 28
<212> TYPE: DNA
<213> ORGANISM: Artificial Sequence
<220> FEATURE:
<223> OTHER INFORMATION: Primer

<400> SEQUENCE: 51
atgaacaagt ggggcgtagg gttaacat                                28

<210> SEQ ID NO 52
<211> LENGTH: 28
<212> TYPE: DNA
<213> ORGANISM: Artificial Sequence
<220> FEATURE:
<223> OTHER INFORMATION: Primer

<400> SEQUENCE: 52
ttaattactt gatttattgt cggcttta                                28

<210> SEQ ID NO 53
<211> LENGTH: 1380
<212> TYPE: DNA
<213> ORGANISM: Saccharomyces cerevisiae

<400> SEQUENCE: 53
ctttaatttt cttttatctt actctcctac ataagacatc aagaaacaat tgtatattgt     60
acaccccccc cctccacaaa cacaaatatt gataatataa agatgtctgc tgctgctgat    120
agattaaact taacttccgg ccacttgaat gctggtagaa agagaagttc ctcttctgtt    180
tctttgaagg ctgccgaaaa gccttttcaag gttactgtga ttggatctgg taactggggt    240
```

```
actactattg ccaaggtggt tgccgaaaat tgtaagggat acccagaagt tttcgctcca    300
atagtacaaa tgtgggtgtt cgaagaagag atcaatggtg aaaaattgac tgaaatcata    360
aatactagac atcaaaacgt gaaatacttg cctggcatca ctctacccga caatttggtt    420
gctaatccag acttgattga ttcagtcaag gatgtcgaca tcatcgtttt caacattcca    480
catcaatttt tgccccgtat ctgtagccaa ttgaaaggtc atgttgattc acacgtcaga    540
gctatctcct gtctaaaggg ttttgaagtt ggtgctaaag tgtccaatt gctatcctct     600
tacatcactg aggaactagg tattcaatgt ggtgctctat ctggtgctaa cattgccacc    660
gaagtcgctc aagaacactg gtctgaaaca acagttgctt accacattcc aaaggatttc    720
agaggcgagg gcaaggacgt cgaccataag gttctaaagg ccttgttcca cagaccttac    780
ttccacgtta gtgtcatcga agatgttgct ggtatctcca tctgtggtgc tttgaagaac    840
gttgttgcct taggttgtgg tttcgtcgaa ggtctaggct ggggtaacaa cgcttctgct    900
gccatccaaa gagtcggttt gggtgagatc atcagattcg gtcaaatgtt tttcccagaa    960
tctagagaag aaacatacta ccaagagtct gctggtgttg ctgatttgat caccacctgc   1020
gctggtggta gaaacgtcaa ggttgctagg ctaatggcta cttctggtaa ggacgcctgg   1080
gaatgtgaaa aggagttgtt gaatggccaa tccgctcaag gtttaattac ctgcaaagaa   1140
gttcacgaat ggttggaaac atgtggctct gtcgaagact cccattatt tgaagccgta    1200
taccaaatcg tttacaacaa ctacccaatg aagaacctgc cggacatgat tgaagaatta   1260
gatctacatg aagattagat ttattggaga aagataacat atcatacttc ccccactttt   1320
ttcgaggctc ttctatatca tattcataaa ttagcattat gtcatttctc ataactactt   1380
```

<210> SEQ ID NO 54
<211> LENGTH: 391
<212> TYPE: PRT
<213> ORGANISM: Saccharomyces cerevisiae

<400> SEQUENCE: 54

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175
```

```
Gly Ala Leu Ser Gly Ala Asn Ile Ala Thr Glu Val Ala Gln Glu His
            180                 185                 190
Trp Ser Glu Thr Thr Val Ala Tyr His Ile Pro Lys Asp Phe Arg Gly
            195                 200                 205
Glu Gly Lys Asp Val Asp His Lys Val Leu Lys Ala Leu Phe His Arg
        210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
    290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
    370                 375                 380
Glu Leu Asp Leu His Glu Asp
385                 390
```

```
<210> SEQ ID NO 55
<211> LENGTH: 753
<212> TYPE: DNA
<213> ORGANISM: Saccharomyces cerevisiae

<400> SEQUENCE: 55
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagtt aagctgtgc     300 aacgctttga cgctctacc aaaagagaaa tgggctgtgg caacttccgg tacccgtgat     360
atggcacaaa atggttcga gcatctggga atcaggagac caaagtactt cattaccgct     420
aatgatgtca acagggtaa gcctcatcca gaaccatatc tgaagggcag gaatggctta     480
ggatatccga tcaatgagca agacccttcc aaatctaagg tagtagtatt tgaagacgct     540
ccagcaggta ttgccgccgg aaaagccgcc ggttgtaaga tcattggtat tgccactact     600
ttcgacttgg acttcctaaa ggaaaaggc tgtgacatca ttgtcaaaaa ccacgaatcc     660
atcagagttg gcggctacaa tgccgaaaca gacgaagttg aattcatttt tgacgactac     720
ttatatgcta aggacgatct gttgaaatgg taa                                  753

<210> SEQ ID NO 56
<211> LENGTH: 250
```

```
<212> TYPE: PRT
<213> ORGANISM: Saccharomyces cerevisiae

<400> SEQUENCE: 56

Met Gly Leu Thr Thr Lys Pro Leu Ser Leu Lys Val Asn Ala Ala Leu
1               5                   10                  15

Phe Asp Val Asp Gly Thr Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Lys Ser Ile Glu Val Pro Gly Ala
                85                  90                  95

Val Lys Leu Cys Asn Ala Leu Asn Ala Leu Pro Lys Glu Lys Trp Ala
                100                 105                 110

Val Ala Thr Ser Gly Thr Arg Asp Met Ala Gln Lys Trp Phe Glu His
            115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
    195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 57
<211> LENGTH: 387
<212> TYPE: PRT
<213> ORGANISM: E. coli

<400> SEQUENCE: 57

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95
```

-continued

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
        130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 58
<211> LENGTH: 1164
<212> TYPE: DNA
<213> ORGANISM: E. coli

<400> SEQUENCE: 58
atgaacaact taatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat taaaagcgcc atcccgatgg gctgtgtgct gacgctgcca     420

```
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa aatcatgaca ttacgttgga tgtcagccgc   1140
cgtatatacg aagccgcccg ctaa                                           1164
```

<210> SEQ ID NO 59
<211> LENGTH: 32
<212> TYPE: DNA
<213> ORGANISM: Artificial Sequence
<220> FEATURE:
<223> OTHER INFORMATION: Primer

<400> SEQUENCE: 59
gcggtaccgt tgctcgacgc tcaggttttc gg                                    32

<210> SEQ ID NO 60
<211> LENGTH: 33
<212> TYPE: DNA
<213> ORGANISM: Artificial Sequence
<220> FEATURE:
<223> OTHER INFORMATION: Primer

<400> SEQUENCE: 60
gcgagctcga cgcttgccct gatcgagttt tgc                                   33

<210> SEQ ID NO 61
<211> LENGTH: 33
<212> TYPE: DNA
<213> ORGANISM: Artificial Sequence
<220> FEATURE:
<223> OTHER INFORMATION: Primer

<400> SEQUENCE: 61
gcgagctcga cgcttgccct gatcgagttt tgc                                   33

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
cagctggcaa ttccggttcg                                                  20

<210> SEQ ID NO 63
<211> LENGTH: 30
<212> TYPE: DNA
<213> ORGANISM: Artificial Sequence

```
<220> FEATURE:
<223> OTHER INFORMATION: Primer

<400> SEQUENCE: 63
cccagctggc aattccggtt cgcttgctgt                                  30

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64
ggcgacccga cgctccagac ggaagctggt                                  30

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
ccgcaagatt cacggatgca tcgtgaaggg                                  30

<210> SEQ ID NO 66
<211> LENGTH: 27
<212> TYPE: DNA
<213> ORGANISM: Artificial Sequence
<220> FEATURE:
<223> OTHER INFORMATION: Primer

<400> SEQUENCE: 66
cgccttcttg acgagttctg agcggga                                     27

<210> SEQ ID NO 67
<211> LENGTH: 30
<212> TYPE: DNA
<213> ORGANISM: Artificial Sequence
<220> FEATURE:
<223> OTHER INFORMATION: Primer

<400> SEQUENCE: 67
ggaattcatg aacaacttta atctgcacac                                  30

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
gtttgaggcg taaaagctt agcgggcggc                                   30
```

PROCESS FOR THE BIOLOGICAL PRODUCTION OF 1,3-PROPANEDIOL WITH HIGH TITER

CROSS-REFERENCE TO RELATED APPLICATION

This is a divisional of U.S. patent application Ser. No. 09/641,652 filed Aug. 18, 2000, now U.S. Pat. No. 6,514,733, which claims benefit of provisional application 60/149,534 filed Aug. 18, 1999.

FIELD OF INVENTION

This invention comprises process for the bioconversion of a fermentable carbon source to 1,3-propanediol by a single microorganism.

BACKGROUND 1,3-Propanediol is a monomer having potential utility in the production of polyester fibers and the manufacture of polyurethanes and cyclic compounds.

A variety of chemical routes to 1,3-propanediol are known. For example ethylene oxide may be converted to 1,3-propanediol over a catalyst in the presence of phosphine, water, carbon monoxide, hydrogen and an acid, by the catalytic solution phase hydration of acrolein followed by reduction, or from compounds such as glycerol, reacted in the presence of carbon monoxide and hydrogen over catalysts having atoms from group VIII of the periodic table. Although it is possible to generate 1,3-propanediol by these methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups *Citrobacter, Clostridilm, Enterobacter, Ilyobacter, Klebsiella, Lactobacillus*, and *Pelobacter*. In each case studied, glycerol is converted to 1,3-propanediol in a two step, enzyme catalyzed reaction sequence. In the first step, a dehydratase catalyzes the conversion of glycerol to 3-hydroxypropionaldehyde (3-HPA) and water, Equation 1. In the second step, 3-HPA is reduced to 1,3-propanediol by a NAD$^+$-linked oxidoreductase, Equation 2. The 1,3-propanediol is not metabolized further and, as a result, Glycerol→3-HPA+H$_2$O      (Equation 1)

3-HPA+NADH+H$^+$→1,3-Propanediol+NAD$^+$      (Equation 2)

accumulates in the media. The overall reaction consumes a reducing equivalent in the form of a cofactor, reduced β-nicotinamide adenine dinucleotide (NADH), which is oxidized to nicotinamide adenine dinucleotide (NAD$^+$).

In *Klebsiella pneumonia, Citrobacter freundii*, and *Clostridium pasteurianum*, the genes encoding the three structural subunits of glycerol dehydratase (dhaB1-3 or dhaB, C and E) are located adjacent to a gene encoding a specific 1,3-propanediol oxidoreductase (dhaT) (see FIG. 1). Although the genetic organization differs somewhat among these microorganisms, these genes are clustered in a group which also comprises orfX and orfZ (genes encoding a dehydratase reactivation factor for glycerol dehydratase), as well as orfY and orfW (genes of unknown function). The specific 1,3-propanediol oxidoreductases (dhaT's) of these microorganisms are known to belong to the family of type III alcohol dehydrogenases; each exhibits a conserved iron-binding motif and has a preference for the NAD$^+$/NADH linked interconversion of 1,3-propandiol and 3-HPA. However, the NAD$^+$/NADH linked interconversion of 1,3-propandiol and 3-HPA is also catalyzed by alcohol dehydrogenases which are not specifically linked to dehydratase enzymes (for example, horse liver and baker's yeast alcohol dehydrogenases (E.C. 1.1.1.1)), albeit with less efficient kinetic parameters. Glycerol dehydratase (E.C. 4.2.1.30) and diol [1,2-propanediol] dehydratase (E.C. 4.2.1.28) are related but distinct enzymes that are encoded by distinct genes. Diol dehydratase genes from *Klebsiella oxytoca* and *Salmonella typhimurium* are similar to glycerol dehydratase genes and are clustered in a group which comprises genes analogous to orfX and orfZ (Daniel et al., *FEMS Microbiol. Rev.* 22, 553 (1999); Toraya and Mori, *J. Biol. Chem.* 274, 3372 (1999); GenBank AF026270).

The production of 1,3-propanediol from glycerol is generally performed under anaerobic conditions using glycerol as the sole carbon source and in the absence of other exogenous reducing equivalent acceptors. Under these conditions, in e.g., strains of *Citrobacter, Clostridium*, and *Klebsiella*, a parallel pathway for glycerol operates which first involves oxidation of glycerol to dihydroxyacetone (DHA) by a NAD$^+$-(or NAPD$^+$-) linked glycerol dehydrogenase, Equation 3. The DHA, following phosphorylation to dihydroxyacetone phosphate (DHAP) by a DHA kinase (Equation 4), Glycerol+NAD$^+$→DHA+NADH+H$^+$      (Equation 3)

DHA+ATP→DHAP+ADP      (Equation 4)

becomes available for biosynthesis and for supporting ATP generation via e.g., glycolysis. In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulon, in *Klebsiella pneumoniae* and *Citrobacter freundii*, also encompasses a gene encoding a transcriptional activator protein (dhaR). The dha regulons from *Citrobacter* and *Klebsiella* have been expressed in *Escherichia coli* and have been shown to convert glycerol to 1,3-propanediol.

Neither the chemical nor biological methods described above for the production of 1,3-propanediol are well suited for industrial scale production since the chemical processes are energy intensive and the biological processes are limited to relatively low titer from the expensive starting material, glycerol. These drawbacks could be overcome with a method requiring low energy input and an inexpensive starting material such as carbohydrates or sugars, or by increasing the metabolic efficiency of a glycerol process. Development of either method will require the ability to manipulate the genetic machinery responsible for the conversion of sugars to glycerol and glycerol to 1,3-propanediol.

Biological processes for the preparation of glycerol are known. The overwhelming majority of glycerol producers are yeasts but some bacteria, other fungi and algae are also known. Both bacteria and yeasts produce glycerol by converting glucose or other carbohydrates through the fructose-1,6-bisphosphate pathway in glycolysis or the Embden Meyerhof Parnas pathway, whereas, certain algae convert dissolved carbon dioxide or bicarbonate in the chloroplasts into the 3-carbon intermediates of the Calvin cycle. In a series of steps, the 3-carbon intermediate, phosphoglyceric acid, is converted to glyceraldehyde 3-phosphate which can be readily interconverted to its keto isomer dihydroxyacetone phosphate and ultimately to glycerol.

Specifically, the bacteria *Bacillus licheniformis* and *Lactobacillus lycopersica* synthesize glycerol, and glycerol production is found in the halotolerant algae *Dunaliella* sp. and *Asteromonas gracilis* for protection against high external salt concentrations. Similarly, various osmotolerant yeasts synthesize glycerol as a protective measure. Most strains of *Saccharomyces* produce some glycerol during alcoholic fermentation, and this can be increased physiologically by the application of osmotic stress. Earlier this century commercial glycerol production was achieved by the use of *Saccharomyces* cultures to which "steering reagents" were added such as sulfites or alkalis. Through the formation of an inactive complex, the steering agents block or inhibit the conversion of acetaldehyde to ethanol; thus, excess reducing equivalents (NADH) are available to or "steered" towards DHAP for reduction to produce glycerol. This method is limited by the partial inhibition of yeast growth that is due to the sulfites. This limitation can be partially overcome by the use of alkalis that create excess NADH equivalents by a different mechanism. In this practice, the alkalis initiated a Cannizarro disproportionation to yield ethanol and acetic acid from two equivalents of acetaldehyde.

The gene encoding glycerol-3-phosphate dehydrogenase (DAR1, GPD1) has been cloned and sequenced from *S. diastaticus* (Wang et al., *J. Bact.* 176, 7091–7095 (1994)). The DAR1 gene was cloned into a shuttle vector and used to transform *E. coli* where expression produced active enzyme. Wang et al. (supra) recognize that DAR1 is regulated by the cellular osmotic environment but do not suggest how the gene might be used to enhance 1,3-propanediol production in a recombinant microorganism.

Other glycerol-3-phosphate dehydrogenase enzymes have been isolated: for example, sn-glycerol-3-phosphate dehydrogenase has been cloned and sequenced from *Saccharomyces cerevisiae* (Larason et al., *Mol. Microbiol.* 10, 1101 (1993)) and Albertyn et al. (*Mol. Cell. Biol.* 14, 4135 (1994)) teach the cloning of GPD1 encoding a glycerol-3-phosphate dehydrogenase from *Saccharomyces cerevisiae*. Like Wang et al. (supra), both Albertyn et al. and Larason et al. recognize the osmo-sensitivity of the regulation of this gene but do not suggest how the gene might be used in the production of 1,3-propanediol in a recombinant microorganism.

As with G3PDH, glycerol-3-phosphatase has been isolated from *Saccharomyces cerevisiae* and the protein identified as being encoded by the GPP1 and GPP2 genes (Norbeck et al., *J. Biol. Chem.* 271, 13875 (1996)). Like the genes encoding G3PDH, it appears that GPP2 is osmosensitive.

Although a single microorganism conversion of fermentable carbon source other than glycerol or dihydroxyacetone to 1,3-propanediol is desirable, it has been documented that there are significant difficulties to overcome in such an endeavor. For example, Gottschalk et al. (EP 373 230) teach that the growth of most strains useful for the production of 1,3-propanediol, including *Citrobacter freundii, Clostridium autobutylicum, Clostridium butylicum*, and *Klebsiella pneumoniae*, is disturbed by the presence of a hydrogen donor such as fructose or glucose. Strains of *Lactobacillus brevis* and *Lactobacillus buchner*, which produce 1,3-propanediol in co-fermentations of glycerol and fructose or glucose, do not grow when glycerol is provided as the sole carbon source, and, although it has been shown that resting cells can metabolize glucose or fructose, they do not produce 1,3-propanediol (Veiga DA Cunha et al., *J. Bacteriol.*, 174, 1013 (1992)). Similarly, it has been shown that a strain of *Ilyobacter polytropus*, which produces 1,3-propanediol when glycerol and acetate are provided, will not produce 1,3-propanediol from carbon substrates other than glycerol, including fructose and glucose (Steib et al., *Arch. Microbiol.* 140, 139 (1984)). Finally, Tong et al. (*Appl. Biochem. Biotech.* 34, 149 (1992)) taught that recombinant *Escherichia coli* transformed with the dha regulon encoding glycerol dehydratase does not produce 1,3-propanediol from either glucose or xylose in the absence of exogenous glycerol.

Attempts to improve the yield of 1,3-propanediol from glycerol have been reported where co-substrates capable of providing reducing equivalents, typically fermentable sugars, are included in the process. Improvements in yield have been claimed for resting cells of *Citrobacter freundii* and *Klebsiella pneumoniae* DSM 4270 co-fermenting glycerol and glucose (Gottschalk et al., supra.; and Tran-Dinh et al., DE 3734 764); but not for growing cells of *Klebsiella pneumoniae* ATCC 25955 co-fermenting glycerol and glucose, which produced no 1,3-propanediol (I-T. Tong, Ph.D. Thesis, University of Wisconsin-Madison (1992)). Increased yields have been reported for the cofermentation of glycerol and glucose or fructose by a recombinant *Escherichia coli*; however, no 1,3-propanediol is produced in the absence of glycerol (Tong et al., supra.). In these systems, single microorganisms use the carbohydrate as a source of generating NADH while providing energy and carbon for cell maintenance or growth. These disclosures suggest that sugars do not enter the carbon stream that produces 1,3-propanediol.

Recently, however, the conversion of carbon substrates, other than glycerol or dihydroxyacetone, to 1,3-propanediol by a single microorganism that expresses a dehydratase enzyme has been described (U.S. Pat. No. 5,686,276; WO 9821339; WO 9928480; and WO 9821341 (U.S. Pat. No. 6,013,494)). A specific deficiency in the biological processes leading to the production of 1,3-propanediol from either glycerol or glucose has been the low titer of the product achieved via fermentation; thus, an energy-intensive separation process to obtain 1,3-propanediol from the aqueous fermentation broth is required. Fed batch or batch fermentations of glycerol to 1,3-propanediol have led to final titers of 65 g/L by *Clostridium butyricum* (Saint-Amans et al., *Biotechnology Letters* 16, 831 (1994)), 71 g/L by *Clostridium butyricum* mutants (Abbad-Andaloussi et al., *Appl. Environ. Microbiol.* 61, 4413 (1995)), 61 g/L by *Klebsiella pneumoniae* (Homann et al., *Appl. Bicrobiol. Biotechnol.* 33, 121 (1990)), and 35 g/L by *Citrobacter freundii* (Homann et al., supra). Fermentations of glucose to 1,3-propanediol that exceed the titer obtained from glycerol fermentations have not yet been disclosed.

The problem that remains to be solved is how to biologically produce 1,3-propanediol, with high titer and by a single microorganism, from an inexpensive carbon substrate such as glucose or other sugars. The biological production of 1,3-propanediol requires glycerol as a substrate for a two-step sequential reaction in which a dehydratase enzyme (typically a coenzyme $B_{12}$-dependent dehydratase) converts glycerol to an intermediate, 3-hydroxypropionaldehyde, which is then reduced to 1,3-propanediol by a NADH- (or NADPH) dependent oxidoreductase. The complexity of the cofactor requirements necessitates the use of a whole cell catalyst for an industrial process that utilizes this reaction sequence for the production of 1,3-propanediol.

SUMMARY OF THE INVENTION

Applicants have solved the stated problem and the present invention provides for bioconverting a fermentable carbon source directly to 1,3-propanediol at significantly higher titer than previously obtained and with the use of a single microorganism. Glucose is used as a model substrate and *E. coli* is used as the model host. In one aspect of this invention, recombinant *E. coli* expressing a group of genes (comprising genes that encode a dehydratase activity, a dehydratase reactivation factor, a 1,3-propanediol oxidoreductase (dhaT), a glycerol-3-phosphate dehydrogenase, and a glycerol-3-phosphatase) convert glucose to 1,3-propanediol at titer that approaches that of glycerol to 1,3-propanediol fermentations.

In another aspect of this invention, the elimination of the functional dhaT gene in this recombinant *E. coli* results in a significantly higher titer of 1,3-propanediol from glucose. This unexpected increase in titer results in improved economics, and thus, an improved process for the production of 1,3-propanediol from glucose.

Furthermore, the present invention may be generally applied to include any carbon substrate that is readily converted to 1) glycerol, 2) dihydroxyacetone, 3) $C_3$ compounds at the oxidation state of glycerol (e.g., glycerol 3-phosphate), or 4) $C_3$ compounds at the oxidation state of dihydroxyacetone (e.g., dihydroxyacetone phosphate or glyceraldehyde 3-phosphate). The production of 1,3-propanediol in the dhaT minus strain requires a non-specific catalytic activity that converts 3-HPA to 1,3-propanediol. Identification of the enzyme(s) and/or gene(s) responsible for the non-specific catalytic activity that converts 3-HPA to 1,3-propanediol will lead to production of 1,3-propanediol in a wide range of host microorganisms with substrates from a wide range of carbon-containing substrates. It is also anticipated that the use of this non-specific catalytic activity that converts 3-HPA to 1,3-propanediol will lead to an improved process for the production of 1,3-propanediol from glycerol or dihydroxyacetone, by virtue of an improved titer and the resulting improved economics.

This activity has been isolated from *E. coli* as a nucleic acid fragment encoding a non-specific catalytic activity for the conversion of 3-hydroxypropionaldehyde to 1,3-propanediol, as set out in SEQ ID NO:58 or as selected from the group consisting of:
(a) an isolated nucleic acid fragment encoding all or a substantial portion of the amino acid sequence of SEQ ID NO:57;
(b) an isolated nucleic acid fragment that is substantially similar to an isolated nucleic acid fragment encoding all or a substantial portion of the amino acid sequence of SEQ ID NO:57;
(c) an isolated nucleic acid fragment encoding a polypeptide of at least 387 amino acids having at least 80% with the amino acid sequence of SEQ ID NO:57;
(d) an isolated nucleic acid fragment that hybridizes with (a) under hybridization conditions of 0.1×SSC, 0.1% SDS, 65° C. and washed with 2×SSC, 0.1% SDS followed by 0.1×SSC, 0.1% SDS; and
(d) an isolated nucleic acid fragment that is complementary to (a), (b), (c), or (d). Alternatively, the nonspecific catalytic acitivity is embodied in the polypeptide as set out in SEQ ID NO:57.

A chimeric gene may be constructed comprising the isolated nucleic acid fragment described above operably linked to suitable regulatory sequences. This chimeric gene can be used to transform miciroorganisms selected from the group consisting of *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Salmonella, Bacillus, Aerobacter, Streptomyces, Escherichia,* and *Pseudomonas. E. coli* is the preferred host.

Accordingly, the present invention provides a recombinant microorganism, useful for the production of 1,3-propanediol comprising: (a) at least one gene encoding a polypeptide having glycerol-3-phosphate dehydrogenase activity; (b) at least one gene encoding a polypeptide having glycerol-3-phosphatase activity; (c) at least one gene encoding a polypeptide having a dehydratase activity; (d) at least one gene encoding a dehydratase reactivation factor; (e) at least one endogenous gene encoding an non-specific catalytic activity sufficient to convert 3-hydroxypropionaldehyde to 1,3-propanediol, wherein no functional dhaT gene encoding a 1,3-propanediol oxidoreductase is present. The preferred embodiment is a recombinant microorganism (preferably *E. coli*) where no dhaT gene is present. Optionally, the recombinant microorganism may comprise mutations (e.g., deletion mutations or point mutations) in endogenous genes selected from the group consisting of: (a) a gene encoding a polypeptide having glycerol kinase activity; (b) a gene encoding a polypeptide having glycerol dehydrogenase activity; and (c) gene encoding a polypeptide having triosephosphate isomerase activity.

In another embodiment the invention includes a process for the production of 1,3-propanediol comprising: (a) contacting, under suitable conditions, a recombinant *E. coli* comprising a dha regulon and lacking a functional dhaT gene encoding a 1,3-propanediol oxidoreductase activity with at least one carbon source, wherein the carbon source is selected from the group consisting of monosaccharides, oligosaccharides, polysaccharides, and single-carbon substrates; and (b) optionally recovering the 1,3-propanediol produced in (a).

The invention also provides a process for the production of 1,3-propanediol from a recombinant microorganism comprising: (a) contacting the recombinant microorganism of the present invention with at least one carbon source selected from the group consisting of monosaccharides, oligosaccharides, polysaccharides, and single-carbon substrates whereby 1,3-propanediol is produced; and (b) optionally recovering the 1,3-propanediol produced in (a).

Similarly the invention intends to provide a process for the production of 1,3-propanediol from a recombinant microorganism comprising:

(a) contacting a recombinant microorganism with at least one carbon source, said recombinant microorganism comprising:
(i) at least one gene encoding a polypeptide having a dehydratase activity;
(ii) at least one gene encoding a dehydratase reactivation factor;
(iii) at least one endogenous gene encoding a non-specific catalytic activity sufficient to convert 3-hydroxypropionaldehyde to 1,3-propanediol; wherein no functional dhaT gene encoding a 1,3-propanediol oxidoreductase is present;

said carbon source selected from the group consisting of glycerol and dihydroxyacetone, wherein 1,3-propanediol is produced and;

(b) optionally recovering the 1,3-propanediol produced in (a).

Yet another aspect of the invention provides for the co-feeding of the carbon substrate. In this embodiment for the production of 1,3-propanediol, the steps are: (a) contacting a recombinant *E. coli* with a first source of carbon and with a second source of carbon, said recombinant *E. coli* comprising: (i) at least one exogenous gene encoding a polypeptide having a dehydratase activity; (ii) at least one exogenous gene encoding a dehydratase reactivation factor; (iii) at least one exogenous gene encoding a non-specific catalytic activity sufficient to convert 3-hydroxypropionaldehyde to 1,3-propanediol, wherein no functional dhaT gene encoding a 1,3-propanediol oxidoreductase activity is present in the recombinant *E. coli* and wherein said first carbon source is selected from the group consisting of glycerol and dihydroxyacetone, and said second carbon source is selected from the group consisting of monosaccharides, oligosaccharides, polysaccharides, and single-carbon substrates, and (b) the 1,3-propanediol produced in (a) is optionally recovered. The co-feed may be sequential or simultaneous. The recombinant *E. coli* used in a co-feeding embodiments may further comprise: (a) a set of exogenous genes consisting of (i) at least one gene encoding a polypeptide having glycerol-3-phosphate dehydrogenase activity; (ii) at least one gene encoding a polypeptide having glycerol-3-phosphatase activity; and (iii) at least one subset of genes encoding the gene products of dhaR, orfR, orfX, orfW, dhaB1, dhaB2, dhaB3 and orfZ, and (b) a set of endogenous genes, each gene having a mutation inactivating the gene, the set consisting of: (i) a gene encoding a polypeptide having glycerol kinase activity; (ii) a gene encoding a polypeptide having glycerol dehydrogenase activity; and (iii) a gene encoding a polypeptide having triosephosphate isomerase activity.

Useful recombinant *E. coli* strains include recombinant *E. coli* strain KLP23 comprising: (a) a set of two endogenous genes, each gene having a mutation inactivating the gene, the set consisting of: (i) a gene encoding a polypeptide having a glycerol kinase activity; and (ii) a gene encoding a polypeptide having a glycerol dehydrogenase activity; (b) at least one exogenous gene encoding a polypeptide having glycerol-3-phosphate dehydrogenase activity; (c) at least one exogenous gene encoding a polypeptide having glycerol-3-phosphatase activity; and (d) a plasmid pKP32 and a recombinant *E. coli* strain RJ8 comprising: (a) set of three endogenous genes, each gene having a mutation inactivating the gene, the set consisting of: (i) a gene encoding a polypeptide having a glycerol kinase activity; (ii) a gene encoding a polypeptide having a glycerol dehydrogenase activity; and (iii) a gene encoding a polypeptide having a triosephosphate isomerase activity.

Other useful embodiments include recombinant *E. coli* comprising: (a) a set of exogenous genes consisting of: (i) at least one gene encoding a polypeptide having a dehydratase activity; (ii) at least one gene encoding a polypeptide having glycerol-3-phosphate dehydrogenase activity; (iii) at least one gene encoding a polypeptide having glycerol-3-phosphatase activity; and (iv) at least one gene encoding a dehydratase reactivation factor; and (b) at least one endogenous gene encoding a non-specific catalytic activity to convert 3-hydroxypropionaldehyde to 1,3-propanediol; wherein no functional dhaT gene encoding a 1,3-propanediol oxidoreductase activity is present in the recombinant *E. coli*.

Another embodiments is a recombinant *E. coli* comprising: (a) a set of exogenous genes consisting of (i) at least one gene encoding a polypeptide having glycerol-3-phosphate dehydrogenase activity; (ii) at least one gene encoding a polypeptide having glycerol-3-phosphatase activity; and (iii) at least one subset of genes encoding the gene products of dhaR, orfY, orfX, orfW, dhaB1, dhaB2, dhaB3 and orfZ, and (b) at least one endogenous gene encoding a non-specific catalytic activity to convert 3-hydroxypropionaldehyde to 1,3-propanediol; wherein no functional dhaT gene encoding a 1,3-propanediol oxidoreductase activity is present in the recombinant *E. coli*. This embodiment also includes a process using a recombinant *E. coli* further comprising a set of endogenous genes, each gene having a mutation inactivating the gene, the set consisting of: (a) a gene encoding a polypeptide having glycerol kinase activity; (b) a gene encoding a polypeptide having glycerol dehydrogenase activity; and (c) a gene encoding a polypeptide having triosephosphate isomerase activity.

This embodiment still further includes a process for the bioproduction of 1,3-propanediol comprising: (a) contacting under suitable conditions the immediately disclosed recombinant *E. coli* with at least one carbon source selected from the group consisting of monosaccharides, oligosaccharides, polysaccharides, and single-carbon substrates whereby 1,3-propanediol is produced; and (b) optionally recovering the 1,3-propanediol produced in (a).

And also includes a further process for the bioproduction of 1,3-propanediol comprising: (a) contacting the recombinant *E. coli* of the immediately disclosed embodiments that further comprise: (i) at least one exogenous gene encoding a polypeptide having a dehydratase activity; (ii) at least one exogenous gene encoding a dehydratase reactivation factor; (iii) at least one endogenous gene encoding a non-specific catalytic activity to convert 3-hydroxypropionaldehyde to 1,3-propanediol, with at least one carbon source selected from the group consisting of glycerol and dihydroxyacetone, and (b) optionally recovering the 1,3-propanediol produced in (a).

BRIEF DESCRIPTION OF THE DRAWINGS, SEQUENCE DESCRIPTIONS, AND BIOLOGICAL DEPOSITS

The invention can be more fully understood from the following detailed description, Figures, the accompanying sequence descriptions, and biological deposits that form parts of this application.

FIG. 1 presents the gene organization within the sequence of the dha regulon subclone pHK28-26.

FIG. 2 presents a graph of the extracellular soluble protein (g/L) compared between two fermentations runs essentially as described in Example 7 using a constant feed of vitamin $B_{12}$. In one case, solid lines, the strain used was KLP23/pAH48/pKP32. In the other case, dashed lines, the strain used was KLP23/pAH48/pDT29.

FIG. 3 presents a graph of the cell viability [(viable cells/mL)/OD550] compared between two fermentations runs essentially as described in Example 7 using a constant feed of vitamin $B_{12}$. In one case (solid lines), the strain used was KLP23/pAH48/pKP32. In the other case (dashed lines), the strain used was KLP23/pAH48/pDT29.

FIG. 4 presents a graph of the yield of glycerol from glucose compared between two fermentations runs essentially as described in Example 7, but in the absence of vitamin $B_{12}$ or coenzyme $B_{12}$. In one case (solid lines), the strain used was KLP23/pAH48/pKP32. In the other case (dashed lines), the strain used was KLP23/pAH48/pDT29.

Figure 1:
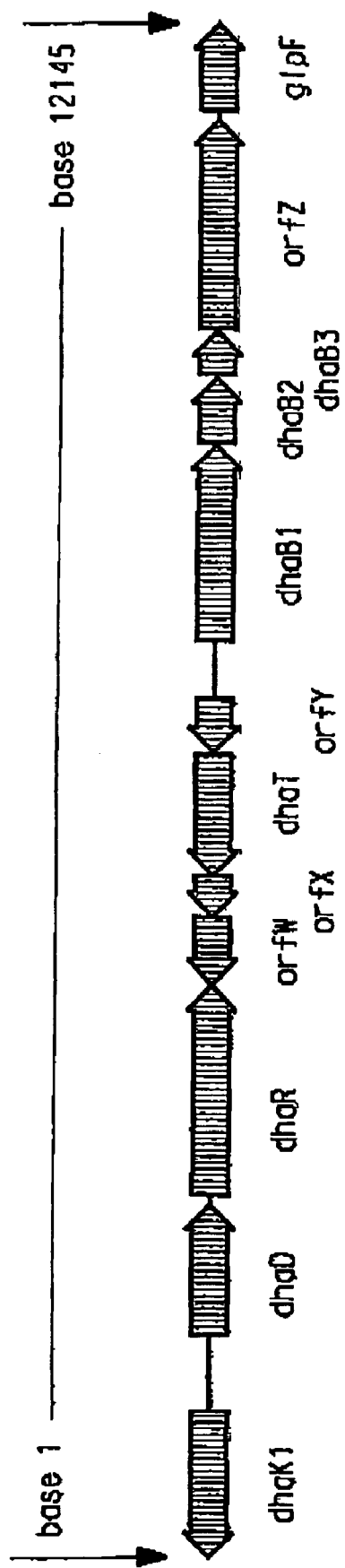

The 68 sequence descriptions and the sequence listing attached hereto will comply with the rules governing nucleotide and/or amino acid sequence disclosures in patent applications as set forth in 37 C.F.R. §1.821–1.825 ("Requirements for Patent Applications Containing Nucleotide Sequences and/or Amino Acid Sequence Disclosures—the Sequence Rules") and will be consistent with World Intellectual Property Organization (WIPO) Standard ST2.5 (1998) and the sequence listing requirements of the EPO and PCT (Rules 5.2 and 49.5(a-bis), and Section 208 and Annex C of the Administration Instructions). The Sequence Descriptions contain the one letter code for nucleotide sequence characters and the three letter codes for amino acids as defined in conformity with the IUPAC-IYUB standards described in *Nucleic Acids Res.* 13, 3021–3030 (1985) and in the *Biochemical Journal* 219, 345–373 (1984) which are herein incorporated by reference.

SEQ ID NO:1 contains the nucleotide sequence determined from a 12.1 kb EcoRI-SalI fragment from pKP1 (cosmid containing DNA from *Klebsiella pneumoniae*), subcloned into pIBI31 (IBI Biosystem, New Haven, Conn.), and termed pHK28-26. Table 1 further details genes, corresponding base pairs identified within SEQ ID NO:1, and associated functionality. See also Example 1.

SEQ ID NO:57 contains the nucleotide sequence determined for yqhD.

SEQ ID NO:58 contains the nucleotide sequence determined for yqhD.

Applicants have made the following biological deposits under the terms of the Budapest Treaty on the International Recognition of the Deposit of Micro-organisms for the Purposes of Patent Procedure:

| Depositor Identification Reference | Int'l Depository Designation | Date of Deposit |
|---|---|---|
| E. coli DH5α; transformed with plasmid pKP1 comprising a portion of the Klebsiella genome encoding the glycerol dehydratase enzyme | ATCC 69789 | 18 Apr. 1995 |
| E. coli DH5α; transformed with plasmid pKP4 comprising a portion of the Klebsiella genome encoding the diol dehydratase enzyme | ATCC 69790 | 18 Apr. 1995 |
| E. coli MSP33.6 comprising a deletion in gldA | ATCC 98598 | 25 Nov. 1997 |
| E. coli RJF10m comprising a deletion in glpK | ATCC 98597 | 25 Nov. 1997 |

The deposit(s) will be maintained in the indicated international depository for at least 30 years and will be made available to the public upon the grant of a patent disclosing it. The availability of a deposit does not constitute a license to practice the subject invention in derogation of patent rights granted by government action.

As used herein, "ATCC" refers to the American Type Culture Collection international depository located 10801 University Blvd., Manassas, Va. 20110-2209 U.S.A. The "ATCC No." is the accession number to cultures on deposit with the ATCC.

DETAILED DESCRIPTION OF THE INVENTION

The present invention provides for an improved process for bioconverting a fermentable carbon source directly to 1,3-propanediol using a single microorganism. The method is characterized by improved titer, yield, and cell viability as well as a decrease in cell lysis during fermentation.

The present invention is based, in part, upon the observation that 1,3-propanediol fermentation processes comprising 1,3-propanediol oxidoreductase (dhaT) are characterized by high levels of 3HPA and other aldehydes and ketones in the medium, which is correlated to a decrease in cell viability. The present invention is also based, in part, upon the unexpected finding that the model host, E. coli, is capable of converting 3-HPA to 1,3-propanediol by an endogenous non-specific catalytic activity capable of converting 3-hydroxypropionaldehyde to 1,3-propanediol. The present invention is further based, in part, upon the unexpected finding that an E. coli fermentation process comprising this non-specific catalytic activity and lacking a functional dhaT results in increased cell viability during fermentation and provides for higher titers and/or yields of 1,3-propanediol than a fermentation process comprising a functional dhaT.

In one aspect, glycerol is a model substrate, the host microorganism has a mutation in wild-type dhaT such that there is no 1,3-propanediol oxidoreductase activity and comprises a non-specific catalytic activity sufficient to convert 3-hydroxypropionaldehyde to 1,3-propanediol. In another aspect, glucose is a model substrate and recombinant E. coli is a model host. In this aspect, E. coli comprises an endogenous non-specific catalytic activity sufficient to convert 3-hydroxypropionaldehyde to 1,3-propanediol. In one embodiment, the non-specific catalytic activity is an alcohol dehydrogenase.

In one aspect, the present invention provides a recombinant E. coli expressing a group of genes comprising (a) at least one gene encoding a polypeptide having glycerol-3-phosphate dehydrogenase activity; (b) at least one gene encoding a polypeptide having glycerol-3-phosphatase activity; (c) at least one gene encoding a polypeptide having a dehydratase activity; (d) at least one gene encoding a dehydratase reactivation factor; and (e) at least one endogenous gene encoding an non-specific catalytic activity sufficient to convert 3-hydroxypropionaldehyde to 1,3-propanediol; use of this microorganism converts glucose to 1,3-propanediol at a high titer. In another aspect of this invention, the elimination of the functional dhaT gene in this recombinant E. coli provides an unexpectedly higher titer of 1,3-propanediol from glucose than previously attained.

The present invention provides an improved method for the biological production of 1,3-propanediol from a fermentable carbon source in a single microorganism. In one aspect of the present invention, an improved process for the conversion of glucose to 1,3-propanediol is achieved by the use of a recombinant microorganism comprising a host E. coli transformed with the *Klebsiella pneumoniae* dha regulon genes dhaR, orfY, dhaT, orfX, orfW, dhaB1, dhaB2, dhaB3, and orfZ, all these genes arranged in the same genetic organization as found in wild type *Klebsiella pneumoniae*. The titer obtained for the fermentation process is significantly higher than any titer previously reported for a similar fermentation. This improvement relies on the use of the plasmid pDT29 as described in Example 6 and Example 7.

In another aspect of the present invention, a further improved process for the production of 1,3-propanediol from glucose is achieved using a recombinant *E. coli* containing genes encoding a G3PDH, a G3P phosphtase, a dehydratase, and a dehydratase reactivation factor compared to a process using a recombinant *E. coli* containing genes encoding a G3PDH, a G3P phosphatase, a dehydratase, a dehydratase reactivation factor, and also a functional dhaT. The dramatically improved process relies on an endogenous gene encoding a non-specific catalytic activity, expected to be an alcohol dehydrogenase, which is present in *E. coli*.

Figure 2:
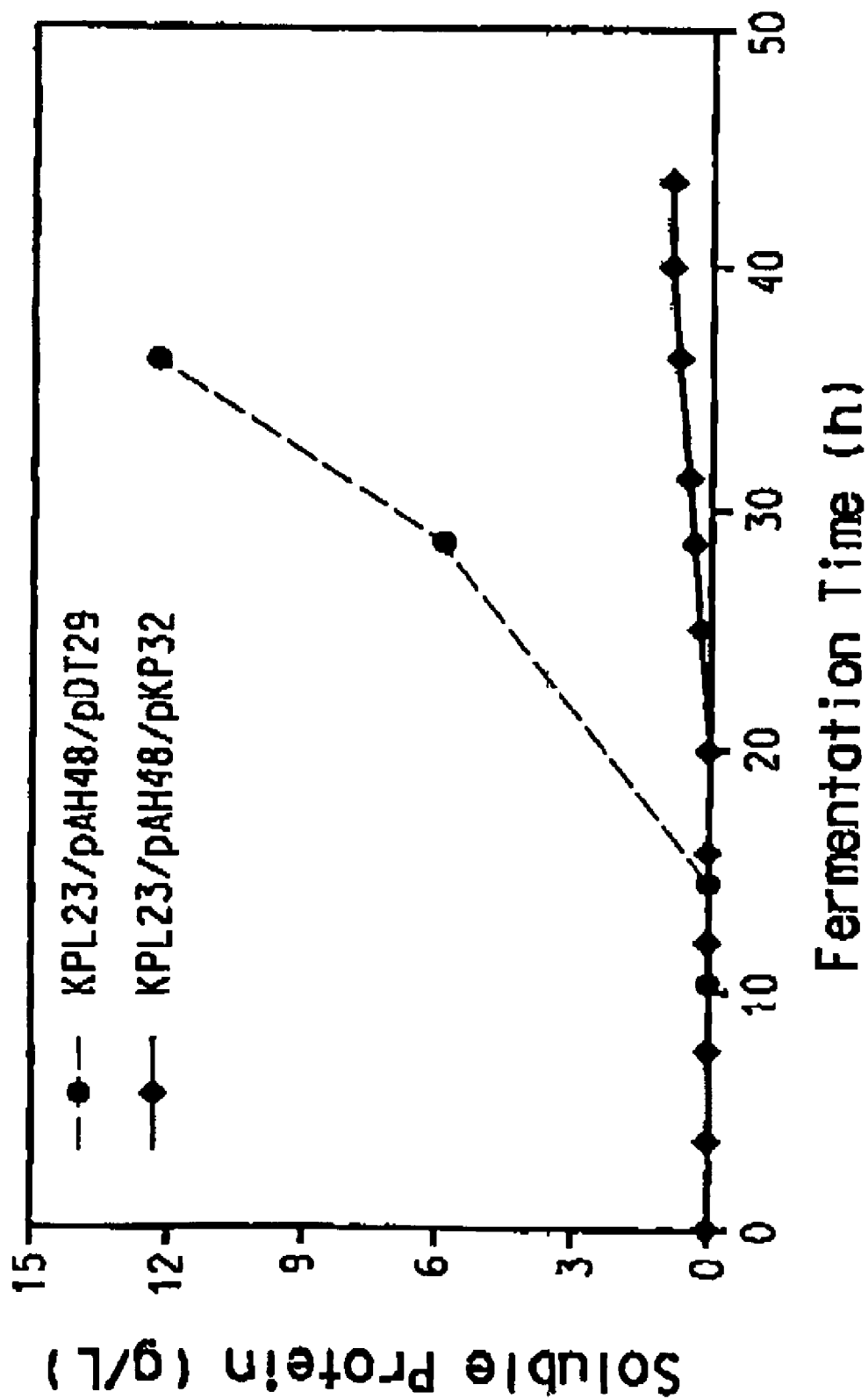
Figure 3:
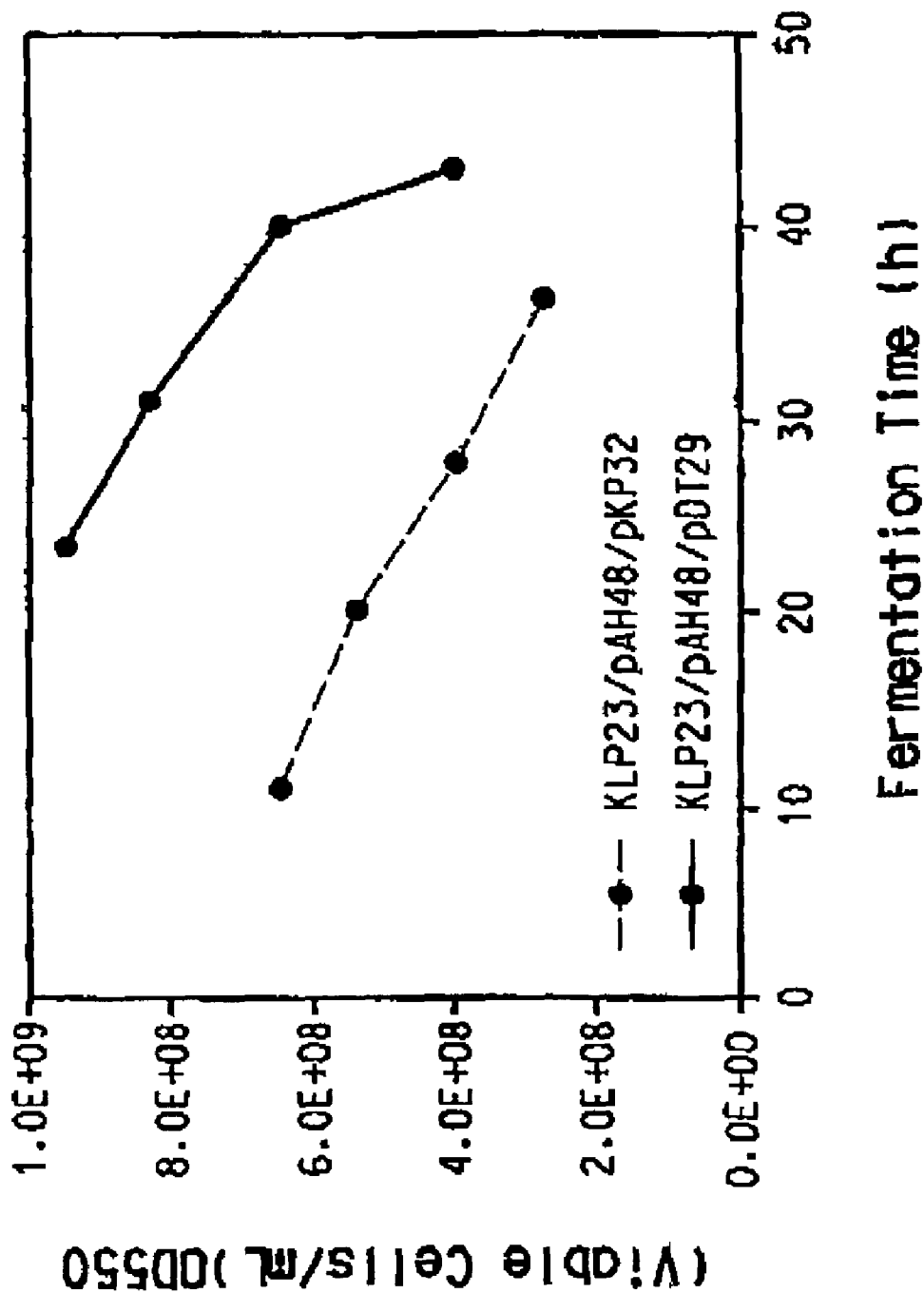
Figure 4:
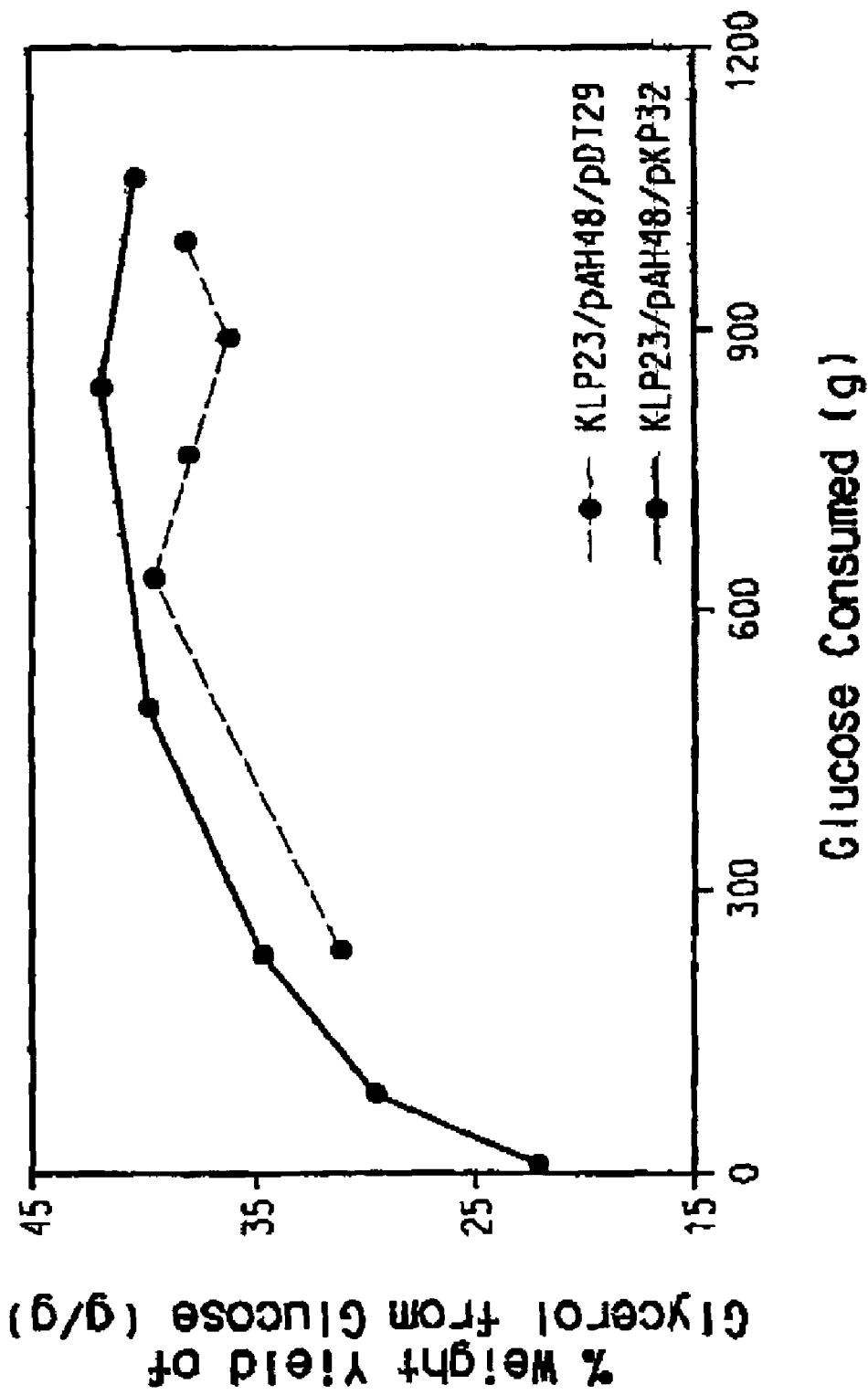

The dramatic improvement in the process is evident as an increase in 1,3-propanediol titer as illustrated in Examples 7 and 9. The improvement in the process is also evident as a decrease in cell lysis as determined by the extracellular soluble protein concentration in the fermentation broth. This aspect of the invention is illustrated in FIG. 2. Additionally, the improvement in the process is evident as prolonged cell viability over the course of the fermentation. This aspect of the invention is illustrated in FIG. 3. Furthermore, the improvement in the process is also evident as an increase in yield. In *E. coli* expressing a 1,3-propanediol oxidoreductase (dhaT) (for example, *E. coli* KLP23 transformed with the plasmid pDT29), glycerol can be metabolized to a product other than 3-HPA. In direct contrast, in *E. coli* not expressing a 1,3-propanediol oxidoreductase (dhaT) (for example, *E. coli* KLP23 transformed with the plasmid pKP32), glycerol is not metabolized to a product other than 3-HPA. That this cryptic pathway is attributable to the presence or absence of a functional dhaT is demonstrated by the lower yield of glycerol from glucose as illustrated in FIG. 4.

As used herein the following terms may be used for interpretation of the claims and specification.

The terms "glycerol-3-phosphate dehydrogenase" and "G3PDH" refer to a polypeptide responsible for an enzyme activity that catalyzes the conversion of dihydroxyacetone phosphate (DHAP) to glycerol-3-phosphate (G3P). In vivo G3PDH may be NADH; NADPH; or FAD-dependent. When specifically referring to a cofactor specific glycerol-3-phosphate dehydrogenase, the terms "NADH-dependent glycerol-3-phosphate dehydrogenase", "NADPH-dependent glycerol-3-phosphate dehydrogenase" and "FAD-dependent glycerol-3-phosphate dehydrogenase" will be used. As it is generally the case that NADH-dependent and NADPH-dependent glycerol-3-phosphate dehydrogenases are able to use NADH and NADPH interchangeably (for example by the gene encoded by gpsA), the terms NADH-dependent and NADPH-dependent glycerol-3-phosphate dehydrogenase will be used interchangeably. The NADH-dependent enzyme (EC 1.1.1.8) is encoded, for example, by several genes including GPD1 (GenBank Z74071x2), or GPD2 (GenBank Z35169x1), or GPD3 (GenBank G984182), or DAR1 (GenBank Z74071x2). The NADPH-dependent enzyme (EC 1.1.1.94) is encoded by gpsA (GenBank U321643, (cds 197911-196892) G466746 and L45246). The FAD-dependent enzyme (EC 1.1.99.5) is encoded by GUT2 (GenBank Z47047x23), or glpD (GenBank G147838), or glpABC (GenBank M20938) (see WO 9928480 and references therein, which are herein incorporated by reference).

The terms "glycerol-3-phosphatase", "sn-glycerol-3-phosphatase", or "d,l-glycerol phosphatase", and "G3P phosphatase" refer to a polypeptide responsible for an enzyme activity that catalyzes the conversion of glycerol-3-phosphate and water to glycerol and inorganic phosphate. G3P phosphatase is encoded, for example, by GPP1 (GenBank Z47047x125), or GPP2 (GenBank U18813x11) (see WO 9928480 and references therein, which are herein incorporated by reference).

The term "glycerol kinase" refers to a polypeptide responsible for an enzyme activity that catalyzes the conversion of glycerol and ATP to glycerol-3-phosphate and ADP. The high-energy phosphate donor ATP may be replaced by physiological substitutes (e.g., phosphoenolpyruvate). Glycerol kinase is encoded, for example, by GUT1 (GenBank U11583x19) and glpK (GenBank L19201) (see WO 9928480 and references therein, which are herein incorporated by reference).

The term "glycerol dehydrogenase" refers to a polypeptide responsible for an enzyme activity that catalyzes the conversion of glycerol to dihydroxyacetone (E.C. 1.1.1.6) or glycerol to glyceraldehyde (E.C. 1.1.1.72). A polypeptide responsible for an enzyme activity that catalyzes the conversion of glycerol to dihydroxyacetone is also referred to as a "dihydroxyacetone reductase". Glycerol dehydrogenase may be dependent upon NADH (E.C. 1.1.1.6), NADPH (E.C. 1.1.1.72), or other cofactors (e.g., E.C. 1.1.99.22). A NADH-dependent glycerol dehydrogenase is encoded, for example, by gldA (GenBank U00006) (see WO 9928480 and references therein, which are herein incorporated by reference).

The term "dehydratase enzyme" or "dehydratase" will refer to any enzyme activity that catalyzes the conversion of a glycerol molecule to the product 3-hydroxypropionaldehyde. For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium*, and *Klebsiella oxytoca*. In each case, the dehydratase is composed of three subunits: the large or "α" subunit, the medium or "β" subunit, and the small or "γ" subunit. Due to the wide variation in gene nomenclature used in the literature, a comparative chart is given in Table 1 to facilitate identification. The genes are also described in, for example, Daniel et al. (*FEMS Microbiol. Rev.* 22, 553 (1999)) and Toraya and Mori (*J. Biol. Chem.* 274, 3372 (1999)). Referring to Table 1, genes encoding the large or "α" subunit of glycerol dehydratase include dhaB1, gldA and dhaB; genes encoding the medium or "β" subunit include dhaB2, gldB, and dhaC; genes encoding the small or "γ" subunit include dhaB3, gldC, and dhaE. Also referring to Table 1, genes encoding the large or "α" subunit of diol dehydratase include pduC and pddA; genes encoding the medium or "β" subunit include pduD and pddB; genes encoding the small or "γ" subunit include pduE and pddC.

TABLE 1

Comparative chart of gene names and GenBank references for dehydratase and dehydratase linked functions.

| ORGANISM (GenBank Reference) | GENE FUNCTION: regulatory | | unknown | | reactivation | | 1,3-PD dehydrogenase | | unknown | |
|---|---|---|---|---|---|---|---|---|---|---|
| | gene | base pairs | gene | base pairs | gene | base pairs | gene | base pairs | gene | base pairs |
| K. pneumoniae (SEQ ID NO: 1) | dhaR | 2209–4134 | orfW | 4112–4642 | orfX | 4643–4996 | dhaT | 5017–6108 | orfY | 6202–6630 |
| K. pneumoniae (U30903) | | | orf2c | 7116–7646 | orf2b | 6762–7115 | dhaT | 5578–6741 | orf2a | 5125–5556 |
| K. pneumoniae (U60992) | | | | | gdrB | | | | | |
| C. freundii (U09771) | dhaR | 3746–5671 | orfW | 5649–6179 | orfX | 6180–6533 | dhaT | 6550–7713 | orfY | 7736–8164 |
| C. pasteurianum (AF051373) | | | | | | | | | | |
| C. pasteurianum (AF006034) | | | orfW | 210–731 | orfX | 1–196 | dhaT | 1232–2389 | orfY | 746–1177 |
| S. typhimurium (AF026270) | | | | | pduH | 8274–8645 | | | | |
| K. oxytoca (AF017781) | | | | | ddrB | 2063–2440 | | | | |
| K. oxytoca (AF051373) | | | | | | | | | | |

| ORGANISM (GenBank Reference) | GENE FUNCTION: dehydratase, α | | dehydratase, β | | dehydratase, γ | | reactivation | |
|---|---|---|---|---|---|---|---|---|
| | gene | base pairs | gene | base pairs | gene | base pairs | gene | base pairs |
| K. pneumoniae (SEQ ID NO: 1) | dhaB1 | 7044–8711 | dhaB2 | 8724–9308 | dhaB3 | 9311–9736 | orfZ | 9749–11572 |
| K. pneumoniae (U30903) | dhaB1 | 3047–4714 | dhaB2 | 2450–2890 | dhaB3 | 2022–2447 | dhaB4 | 186–2009 |
| K. pneumoniae (U60992) | gldA | 121–1788 | gldB | 1801–2385 | gldC | 2388–2813 | gdrA | |
| C. freundii (U09771) | dhaB | 8556–10223 | dhaC | 10235–10819 | dhaE | 10822–11250 | orfZ | 11261–13072 |
| C. pasteurianum (AF051373) | dhaB | 84–1748 | dhaC | 1779–2318 | dhaE | 2333–2773 | orfZ | 2790–4598 |
| C. pasteurianum (AF006034) | | | | | | | | |
| S. typhimurium (AF026270) | pduC | 3557–5221 | pduD | 5232–5906 | pduE | 5921–6442 | pduG | 6452–8284 |
| K. oxytoca (AF017781) | | | | | | | ddrA | 241–2073 |
| K. oxytoca (AF051373) | pddA | 121–1785 | pddB | 1796–2470 | pddC | 2485–3006 | | |

Glycerol and diol dehydratases are subject to mechanism-based suicide inactivation by glycerol and some other substrates (Daniel et al., FEMS Microbiol. Rev. 22, 553 (1999)). The term "dehydratase reactivation factor" refers to those proteins responsible for reactivating the dehydratase activity. The terms "dehydratase reactivating activity", "reactivating the dehydratase activity" or "regenerating the dehydratase activity" refers to the phenomenon of converting a dehydratase not capable of catalysis of a substrate to one capable of catalysis of a substrate or to the phenomenon of inhibiting the inactivation of a dehydratase or the phenomenon of extending the useful half-life of the dehydratase enzyme in vivo. Two proteins have been identified as being involved as the dehydratase reactivation factor (see WO 9821341 (U.S. Pat. No. 6,013,494) and references therein, which are herein incorporated by reference; Daniel et al., supra; Toraya and Mori, J. Biol. Chem. 274, 3372 (1999); and Tobimatsu et al., J. Bacteriol. 181, 4110 (1999)). Referring to Table 1, genes encoding one of the proteins include orfZ, dhaB4, gdrA, pduG and ddrA. Also referring to Table 1, genes encoding the second of the two proteins include orfX, orf2b, gdrB, pduH and ddrB.

The terms "1,3-propanediol oxidoreductase", "1,3-propanediol dehydrogenase" or "DhaT" refer to the polypeptide(s) responsible for an enzyme activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from Klebsiella pneumonia. Referring to Table 1, genes encoding a 1,3-propanediol oxidoreductase include dhaT from Klebsiella pneumoniae, Citrobacter freundii, and Clostridium pasteurianum. Each of these genes encode a polypeptide belonging to the family of type III alcohol dehydrogenases, exhibits a conserved iron-binding motif, and has a preference for the NAD$^+$/NADH linked intercoversion of 3-HPA and 1,3-propanediol (Johnson and Lin, J. Bacteriol. 169, 2050 (1987); Daniel et al., J. Bacteriol. 177, 2151 (1995); and Leurs et al., FEMS Microbiol. Lett. 154, 337 (1997)). Enzymes with similar physical properties have been isolated from Lactobacillus brevis and Lactobacillus buchneri (Veiga da Dunha and Foster, Appl. Environ. Microbiol. 58, 2005 (1992)).

The term "dha regulon" refers to a set of associated genes or open reading frames encoding various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described herein.

The term "non-specific catalytic activity" refers to the polypeptide(s) responsible for an enzyme activity that is sufficient to catalyze the interconversion of 3-HPA and 1,3-propanediol and specifically excludes 1,3-propanediol oxidoreductase(s). Typically these enzymes are alcohol dehydrogenases. Such enzymes may utilize cofactors other than NAD$^+$/NADH, including but not limited to flavins such as FAD or FMN. A gene(s) for a non-specific alcohol dehydrogenase(s) is found, for example, to be endogenously encoded and functionally expressed within the microorganism E. coli KLP23.

The terms "function" or "enzyme function" refer to the catalytic activity of an enzyme in altering the energy required to perform a specific chemical reaction. It is understood that such an activity may apply to a reaction in equilibrium where the production of either product or substrate may be accomplished under suitable conditions.

The terms "polypeptide" and "protein" are used interchangeably.

The terms "carbon substrate" and "carbon source" refer to a carbon source capable of being metabolized by host microorganisms of the present invention and particularly carbon sources selected from the group consisting of monosaccharides, oligosaccharides, polysaccharides, and one-carbon substrates or mixtures thereof.

The terms "host cell" or "host microorganism" refer to a microorganism capable of receiving foreign or heterologous genes and of expressing those genes to produce an active gene product.

The terms "foreign gene", "foreign DNA", "heterologous gene" and "heterologous DNA" refer to genetic material native to one organism that has been placed within a host microorganism by various means. The gene of interest may be a naturally occurring gene, a mutated gene, or a synthetic gene.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The term "genetically altered" refers to the process of changing hereditary material by transformation or mutation.

The terms "recombinant microorganism" and "transformed host" refer to any microorganism having been transformed with heterologous or foreign genes or extra copies of homologous genes. The recombinant microorganisms of the present invention express foreign genes encoding glycerol-3-phosphate dehydrogenase (GPD1), glycerol-3-phosphatase (GPP2), glycerol dehydratase (dhaB1, dhaB2 and dhaB3), dehydratase reactivation factor (orfZ and orfX), and optionally 1,3-propanediol oxidoreductase (dhaT) for the production of 1,3-propanediol from suitable carbon substrates. A preferred embodiment is an *E. coli* transformed with these genes but lacking a functional dhaT. A host microorganism, other than *E. coli*, may also be transformed to contain the disclosed genes and the gene for the non-specific catalytic activity for the interconversion of 3-HPA and 1,3-propanediol, specifically excluding 1,3-propanediol oxidoreductase(s) (dhaT).

"Gene" refers to a nucleic acid fragment that expresses a specific protein, including regulatory sequences preceding (5' non-coding) and following (3' non-coding) the coding region. The terms "native" and "wild-type" refer to a gene as found in nature with its own regulatory sequences.

The terms "encoding" and "coding" refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences.

The term "isolated" refers to a protein or DNA sequence that is removed from at least one component with which it is naturally associated.

An "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

"Substantially similar" refers to nucleic acid molecules wherein changes in one or more nucleotide bases result in substitution of one or more amino acids, but do not affect the functional properties of the protein encoded by the DNA sequence. "Substantially similar" also refers to nucleic acid molecules wherein changes in one or more nucleotide bases do not affect the ability of the nucleic acid molecule to mediate alteration of gene expression by antisense or co-suppression technology. "Substantially similar" also refers to modifications of the nucleic acid molecules of the instant invention (such as deletion or insertion of one or more nucleotide bases) that do not substantially affect the functional properties of the resulting transcript vis-á-vis the ability to mediate alteration of gene expression by antisense or co-suppression technology or alteration of the functional properties of the resulting protein molecule. The invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology*; Lesk, A. M., Ed.; Oxford University Press: New York, 1988; *Biocomputing: Informatics and Genome Projects*; Smith, D. W., Ed.; Academic Press: New York, 1993; *Computer Analysis of Sequence Data, Part I*; Griffin, A. M. and Griffin, H. G., Eds.; Humana Press: New Jersey, 1994; *Sequence Analysis in Molecular Biology*; von Heinje, G., Ed.; Academic Press: New York, 1987; and *Sequence Analysis Primer*; Gribskov, M. and Devereux, J., Eds.; Stockton Press: New York, 1991. Preferred methods to determine identity are designed to give the largest match between the sequences tested.

Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad Sci. USA* 85:2444–2448 (1988). The BLASTX program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990); Altschul et al., "Gapped BLAST and PSI-BLAST: a new generation of protein database search programs", *Nucleic Acids Res.* 25:3389–3402 (1997)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "homologous" refers to a protein or polypeptide native or naturally occurring in a given host cell. The invention includes microorganisms producing homologous proteins via recombinant DNA technology.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without effecting the amino acid sequence of an encoded polypeptide. Accordingly, the instant invention relates to any nucleic acid molecule that encodes all or a substantial portion of the amino acid sequence as set forth in SEQ ID NO:57. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Construction of Recombinant Organisms

Recombinant organisms containing the necessary genes that will encode the enzymatic pathway for the conversion of a carbon substrate to 1,3-propanediol may be constructed using techniques well known in the art. Genes encoding glycerol-3-phosphate dehydrogenase (GPD1), glycerol-3-phosphatase (GPP2), glycerol dehydratase (dhaB1, dhaB2, and dhaB3), dehydratase reactivation factor (orfZ and orfX) and 1,3-propanediol oxidoreductase (dhaT) were isolated from a native host such as Klebsiella or Saccharomyces and used to transform host strains such as E. coli DH5α, ECL707, AA200, or KLP23.

Isolation of Genes

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, cosmid libraries may be created where large segments of genomic DNA (35–45 kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook, J. et al., *Molecular Cloning: A Laboratory Manual*, Second Edition (1989) Cold Spring Harbor Laboratory Press, herein incorporated by reference.

Typically to clone cosmids, foreign DNA is isolated and ligated, using the appropriate restriction endonucleases, adjacent to the cos region of the cosmid vector. Cosmid vectors containing the linearized foreign DNA are then reacted with a DNA packaging vehicle such as bacteriophage. During the packaging process the cos sites are cleaved and the foreign DNA is packaged into the head portion of the bacterial viral particle. These particles are then used to transfect suitable host cells such as *E. coli*. Once injected into the cell, the foreign DNA circularizes under the influence of the cos sticky ends. In this manner large segments of foreign DNA can be introduced and expressed in recombinant host cells.

Isolation and Cloning of Genes Encoding Glycerol Dehydratase (dhaB1, dhaB2, and dhaB3), Dehydratase Reactivating Factors (orfZ and orfX), and 1,3-propanediol Dehydrogenase (dhaT)

Cosmid vectors and cosmid transformation methods were used within the context of the present invention to clone large segments of genomic DNA from bacterial genera known to possess genes capable of processing glycerol to 1,3-propanediol. Specifically, genomic DNA from *K. pneumoniae* was isolated by methods well known in the art and digested with the restriction enzyme Sau3A for insertion into a cosmid vector Supercos 1 and packaged using GigapackII packaging extracts. Following construction of the vector *E. coli* XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene from *C. freundii*, demonstrating that these transformants contained DNA encoding the glycerol dehydratase gene. Other 1,3-propanediol positive transformants were analyzed and the cosmids were named pKP4 and pKP5. DNA sequencing revealed that these cosmids carried DNA encoding a diol dehydratase gene.

Although the instant invention utilizes the isolated genes from within a *Klebsiella* cosmid, alternate sources of dehydratase genes and dehydratase reactivation factor genes include, but are not limited to, *Citrobacter, Clostridia* and *Salmonella* (see Table 1).

Genes Encoding G3PDH and G3P Phosphatase

The present invention provides genes suitable for the expression of G3PDH and G3P phosphatase activities in a host cell.

Genes encoding G3PDH are known. For example, GPD1 has been isolated from *Saccharomyces* and has the base sequence given by SEQ ID NO:53, encoding the amino acid sequence given in SEQ ID NO:54 (Wang et al., supra). Similarly, G3PDH activity has also been isolated from *Saccharomyces* encoded by GPD2 (Eriksson et al., *Mol. Microbiol.* 17, 95 (1995)).

For the purposes of the present invention it is contemplated that any gene encoding a polypeptide responsible for NADH-dependent G3PDH activity is suitable wherein that activity is capable of catalyzing the conversion of dihydroxyacetone phosphate (DHAP) to glycerol-3-phosphate (G3P). Further, it is contemplated that any gene encoding the amino acid sequence of NADH-dependent G3PDH's corresponding to the genes DAR1, GPD1, GPD2, GPD3, and gpsA will be functional in the present invention wherein that amino acid sequence may encompass amino acid substitutions, deletions or additions that do not alter the function of the enzyme. The skilled person will appreciate that genes encoding G3PDH isolated from other sources will also be suitable for use in the present invention. Genes encoding G3P phosphatase are known. For example, GPP2 has been isolated from *Saccharomyces cerevisiae* and has the base sequence given by SEQ ID NO:55, which encodes the amino acid sequence given in SEQ ID NO:56 (Norbeck et al., *J. Biol. Chem.* 271, 13875 (1996)).

For the purposes of the present invention, any gene encoding a G3P phosphatase activity is suitable for use in the method wherein that activity is capable of catalyzing the conversion of glycerol-3-phosphate plus $H_2O$ to glycerol plus inorganic phosphate. Further, any gene encoding the amino acid sequence of G3P phosphatase corresponding to the genes GPP2 and GPP1 will be functional in the present invention including any amino acid sequence that encompasses amino acid substitutions, deletions or additions that do not alter the function of the G3P phosphatase enzyme. The skilled person will appreciate that genes encoding G3P phosphatase isolated from other sources will also be suitable for use in the present invention.

Host Cells

Suitable host cells for the recombinant production of 1,3-propanediol may be either prokaryotic or eukaryotic and will be limited only by the host cell ability to express the active enzymes for the 1,3-propanediol pathway. Suitable host cells will be bacteria such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces*, and *Pseudomonas*. Preferred in the present invention are *E. coli, E. blattae, Klebsiella, Citrobacter*, and *Aerobacter*.

Microorganisms can be converted to a high titer 1,3-propanediol producer by using the following general protocol.

1. Determine the presence in a potential host organism of an endogenous dhaT-like activity that allows for the steady state concentration of a toxic or inhibitory level of 3-HPA in the presence of 1–2 M 1,3-propanediol.
2. If such an activity exists in the potential host organism, perform suitable mutagenisis to delete or inactivate this activity. Confirmation of a non-functional or deleted dhaT-like activity can be detected by the lack of 3-HPA accumulation in the presence of 1–2 M 1,3-propanediol.

3. Express appropriate genes for a) glycerol production, if glycerol is not the carbon source, b) glycerol dehydratase and the associated maintenance system, and c) yqhD.

Considerations which would need to be taken with respect to certain microorganisms concern the expression or repression of endogenous dhaT-like enzymes under the conditions for 1,3-propanediol production. These might also include the presence of glycerol, glucose or anaerobisis.

Vectors and Expression Cassettes

The present invention provides a variety of vectors and transformation and expression cassettes suitable for the cloning, transformation and expression of G3PDH, G3P phosphatase, dehydratase, and dehydratase reactivation factor into a suitable host cell. Suitable vectors will be those which are compatible with the microorganism employed. Suitable vectors can be derived, for example, from a bacteria, a virus (such as bacteriophage T7 or a M-13 derived phage), a cosmid, a yeast or a plant. Protocols for obtaining and using such vectors are known to those in the art (Sambrook et al., *Molecular Cloning: A Laboratory Manual*—volumes 1, 2, 3 (Cold Spring Harbor Laboratory: Cold Spring Harbor, N.Y., 1989)).

Typically, the vector or cassette contains sequences directing transcription and translation of the appropriate gene, a selectable marker, and sequences allowing autonomous replication or chromosomal integration. Suitable vectors comprise a region 5' of the gene, which harbors transcriptional initiation controls, and a region 3' of the DNA fragment which controls transcriptional termination. It is most preferred when both control regions are derived from genes homologous to the transformed host cell. Such control regions need not be derived from the genes native to the specific species chosen as a production host.

Initiation control regions, or promoters, which are useful to drive expression of the G3PDH and G3P phosphatase genes (DAR1 and GPP2, respectively) in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Particularly useful in the present invention are the vectors pDT29 and pKP32 which are designed to be used in conjunction with pAH48. The essential elements of pDT29 and pKP32 are derived from the dha regulon isolated from *Klebsiella pneumoniae*. pDT29 contains the open reading frames dhaR, orfY, dhaT, orfX, orfW, dhaB1, dhaB2, and dhaB3, nucleotide the sequences of which are contained within SEQ ID NO:1. pKP32 contains the same set of open reading frames as found on pDT29, from the same source, with the difference that pKP32 lacks the dhaT. pAH48 is the vehicle used for the introduction of DAR1 and GPP2 genes into the host cell and more specifically comprises the DAR1 and GPP2 genes isolated from *Saccharomyces cerevisiae*.

Transformation of Suitable Hosts and Expression of Genes for the Production of 1,3-propanediol Once suitable cassettes are constructed they are used to transform appropriate host cells. Introduction of the cassette containing the genes encoding G3PDH, G3P phosphatase, dehydratase, and dehydratase reactivation factor into the host cell may be accomplished by known procedures such as by transformation (e.g., using calcium-permeabilized cells, electroporation), or by transfection using a recombinant phage virus (Sambrook et al., supra).

In the present invention cassettes were used to transform the *E. coli* as fully described in the GENERAL METHODS and EXAMPLES.

Mutants

In addition to the cells exemplified, it is contemplated that the present method will be able to make use of cells having single or multiple mutations specifically designed to enhance the production of 1,3-propanediol. Cells that normally divert a carbon feed stock into non-productive pathways, or that exhibit significant catabolite repression could be mutated to avoid these phenotypic deficiencies. For example, many wild type cells are subject to catabolite repression from glucose and by-products in the media and it is contemplated that mutant strains of these wild type organisms, capable of 1,3-propanediol production that are resistant to glucose repression, would be particularly useful in the present invention.

Methods of creating mutants are common and well known in the art. For example, wild type cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See for example Brock, Supra; DeMancilha et al., *Food Chem.* 14, 313 (1984).

The elimination of an undesired enzyme activity may be also accomplished by disruption of the gene encoding the enzyme. Such methods are known to those skilled in the art and are exemplified in Example 4 and Example 8.

Alterations in the 1,3-propanediol Production Pathway Representative Enzyme Pathway.

Figure 5:
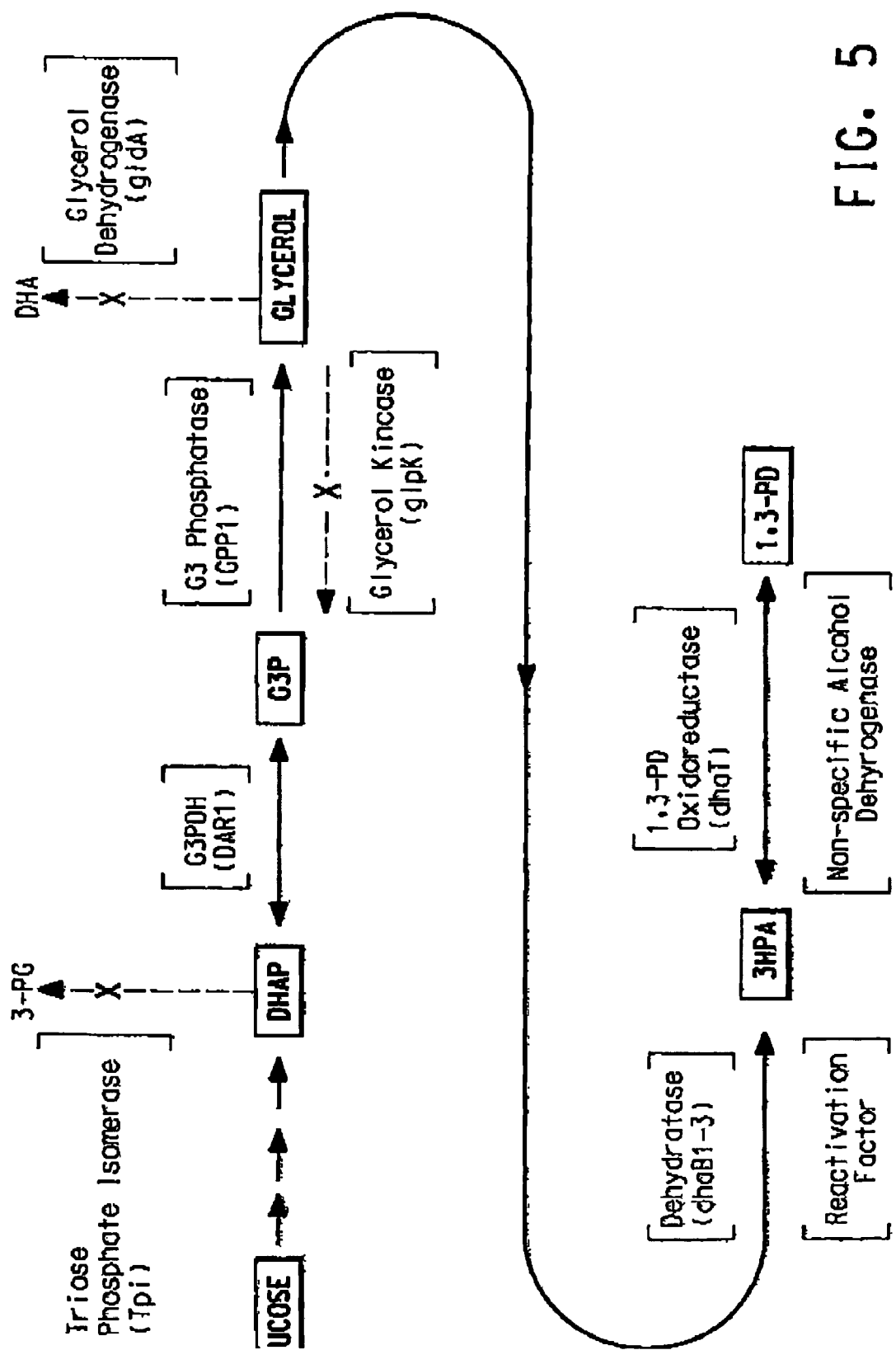
FIG. 5 is a flow diagram illustrating the metabolic conversion of glucose to 1,3-propanediol.

The production of 1,3-propanediol from glucose can be accomplished by the following series of steps. This series is representative of a number of pathways known to those skilled in the art and is illustrated in FIG. 5. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases, which are known to be non-specific with respect to their substrates, or the activity can be introduced into the host by recombination. The reduction step can be catalyzed by a NAD+ (or NADP+) linked host enzyme or the activity can be introduced into the host by recombination. It is notable that the dha regulon contains a glycerol dehydrogenase (E.C. 1.1.1.6) that catalyzes the reversible reaction of Equation 3.

Glycerol→3-HPA+H₂O        (Equation 1)

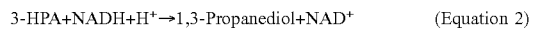
3-HPA+NADH+H⁺→1,3-Propanediol+NAD⁺        (Equation 2)

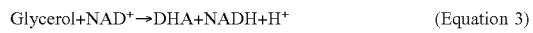
Glycerol+NAD⁺→DHA+NADH+H⁺        (Equation 3)

Glycerol is converted to 1,3-propanediol via the intermediate 3-hydroxypropionaldehye (3-HPA) as has been described in detail above. The intermediate 3-HPA is produced from glycerol, Equation 1, by a dehydratase enzyme that can be encoded by the host or can be introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HPA, Equation 2, by a NAD⁺-(or NADP⁺) linked host enzyme or the activity can be introduced into the host by recombination. This final reaction in the production of 1,3-propanediol can be catalyzed by 1,3-propanediol dehydrogenase (E.C. 1.1.1.202) or other alcohol dehydrogenases.

Mutations and transformations that affect carbon channeling.

A variety of mutant microorganisms comprising variations in the 1,3-propanediol production pathway will be useful in the present invention. For example the introduction of a triosephosphate isomerase mutation (tpi-) into the microorganism of the present invention is an example of the use of a mutation to improve the performance by carbon channeling. Triosephosphate isomerase is the enzyme responsible for the conversion of DAHP to 3-phosphoglyceraldehyde, and as such allows the diversion of carbon flow from the main pathway form glucose to glycerol and 1,3-propanediol (FIG. 5). Thus, the deletion mutation (tpi-) enhances the overall metabolic efficiency of the desired pathway over that described in the art. Similarly, mutations which block alternate pathways for intermediates of the 1,3-propanediol production pathway would also be useful to the present invention. For example, the elimination of glycerol kinase prevents glycerol, formed from G3P by the action of G3P phosphatase, from being re-converted to G3P at the expense of ATP (FIG. 5). Also, the elimination of glycerol dehydrogenase (for example, gldA) prevents glycerol, formed from DHAP by the action of NADH-dependent glycerol-3-phosphate dehydrogenase, from being converted to dihydroxyacetone (FIG. 5). Mutations can be directed toward a structural gene so as to impair or improve the activity of an enzymatic activity or can be directed toward a regulatory gene, including promoter regions and ribosome binding sites, so as to modulate the expression level of an enzymatic activity.

It is thus contemplated that transformations and mutations can be combined so as to control particular enzyme activities for the enhancement of 1,3-propanediol production. Thus, it is within the scope of the present invention to anticipate modifications of a whole cell catalyst which lead to an increased production of 1,3-propanediol.

The present invention utilizes a preferred pathway for the production of 1,3-propanediol from a sugar substrate where the carbon flow moves from glucose to DRAP, G3P, Glycerol, 3-HPA and finally to 1,3-propanediol. The present production strains have been engineered to maximize the metabolic efficiency of the pathway by incorporating various deletion mutations that prevent the diversion of carbon to non-productive compounds. Glycerol may be diverted from conversion to 3HPA by transformation to either DHA or G3P via glycerol dehydrogenase or glycerol kinase as discussed above (FIG. 5). Accordingly, the present production strains contain deletion mutations in the gld, and glpK genes. Similarly DHAP may be diverted to 3-PG by triosephosphate isomerase, thus the present production microorganism also contains a deletion mutation in this gene. The present method additionally incorporates a dehydratase enzyme for the conversion of glycerol to 3HPA, which functions in concert with the reactivation factor, encoded by orjX and orfZ of the dha regulon (FIG. 5). Although conversion of the 3HPA to 1,3-propanediol is typically accomplished via a 1,3-propanediol oxidoreductase, the present method utilizes a non-specific catalytic activity that produces greater titers and yields of the final product, 1,3-propanediol (FIG. 5). In such a process, titers of 1,3-propanediol of at least 10 g/L are achieved, where titers of 200 g/L are expected.

Alternatively, an improved process for 1,3-propanediol production may utilize glycerol or dihydroxyacetone as a substrate where the pathway comprises only the last three substrates, glycerol→3HPA→1,3-propanediol. In such a process, the oxidoreductase is again eliminated in favor of the non-specific catalytic activity, (expected to be an alcohol dehydrogenase), however the need for deletion mutations are nullified by the energy considerations of adding glycerol to the culture. In such as process titers of 1,3-propanediol of at least 71 g/L are achieved where titers of 200 g/L are expected.

Similarly it is within the scope of the invention to provide mutants of wildtype microorganisms that have been modified by the deletion or mutation of the dhaT activity to create improved 1,3-propandiol producers. For example, microorganisms, which naturally contain all the elements of the dha regulon, may be manipulated so as to inactivate the dhaT gene encoding the 1,3-propandiol oxidoreductase activity.

These microorganisms will be expected to produce. higher yields and titers of 1,3-propanediol, mediated by the presence of an endogenous catalytic activity, expected to be an alcohol dehydrogenase. Examples of such microorganisms include but are not limited to *Klebsiella* sp., *Citrobacter* sp., and *Clostridium* sp.

Media and Carbon Substrates

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. Glycerol production from single carbon sources (e.g., methanol, formaldehyde or formate) has been reported in methylotrophic yeasts (K. Yamada et al., *Agric. Biol. Chem.* 53(2), 541–543 (1989)) and in bacteria (Hunter et. al., *Biochemistry* 24, 4148–4155 (1985)). These microorganisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York (1986)). The ribulose monophosphate pathway involves the condensation of formate with ribulose 5-phosphate to form a 6-carbon sugar that becomes fructose and eventually the three-carbon product glyceraldehyde-3-phosphate. Likewise, the serine pathway assimilates the one-carbon compound into the glycolytic pathway via methylenetetrahydrofolate.

In addition to one and two carbon substrates, methylotrophic microorganisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153(5), 485–489 (1990)). Hence, it is contemplated that the source of carbon utilized in the present invention may encompass a wide variety of carbon-containing substrates and will only be limited by the choice of microorganism or process.

Although it is contemplated that all of the above mentioned carbon substrates and mixtures (co-feed) thereof are suitable in the present invention, preferred carbon substrates are glucose, fructose, sucrose, or methanol where the process intends to produce an endogenous glycerol, and glycerol or dihydroxyacetone where the process anticipates a glycerol or dihydroxyacetone feed.

In addition to an appropriate carbon source, fermentation media must contain suitable minerals, salts, cofactors, buffers and other components, known to those skilled in the art, suitable for the growth of the cultures and promotion of the enzymatic pathway necessary for 1,3-propanediol production. Particular attention is given to Co(II) salts and/or vitamin $B_{12}$ or precursors thereof.

Adenosyl-cobalamin (coenzyme $B_{12}$) is an essential cofactor for dehydratase activity. Synthesis of coenzyme $B_{12}$ is found in prokaryotes, some of which are able to synthesize the compound de novo, for example, *Escherichia blattae*, *Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, need be provided in *E. coli* fermentations.

Vitamin $B_{12}$ additions to *E. coli* fermentations may be added continuously, at a constant rate or staged as to coincide with the generation of cell mass, or may be added in single or multiple bolus additions. Preferred ratios of vitamin $B_{12}$ (mg) fed to cell mass (OD550) are from 0.06 to 0.60. Most preferred ratios of vitamin $B_{12}$ (mg) fed to cell mass (OD550) are from 0.12 to 0.48.

Although vitamin $B_{12}$ is added to the transformed *E. coli* of the present invention it is contemplated that other microorganisms, capable of de novo $B_{12}$ biosynthesis will also be suitable production cells and the addition of $B_{12}$ to these microorganisms will be unnecessary.

Culture Conditions:

Typically cells are grown at 35° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations.

Suitable pH ranges for the fermentation are between pH 5.0 to pH 9.0, where pH 6.0 to pH 8.0 is preferred as the initial condition.

Reactions may be performed under aerobic or anaerobic conditions where anaerobic or microaerobic conditions are preferred.

Fed-batch fermentations may be performed with carbon feed, for example, glucose, limited or excess.

Batch and Continuous Fermentations:

The present process employs a batch method of fermentation. Classical batch fermentation is a closed system where the composition of the media is set at the beginning of the fermentation and is not subject to artificial alterations during the fermentation. Thus, at the beginning of the fermentation the media is inoculated with the desired microorganism or microorganisms and fermentation is permitted to occur adding nothing to the system. Typically, however,"batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Identification and Purification of 1,3-propanediol:

Methods for the purification of 1,3-propanediol from fermentation media are known in the art. For example, propanediols can be obtained from cell media by subjecting the reaction mixture to extraction with an organic solvent, distillation, and column chromatography (U.S. Pat No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01N sulfuric acid in an isocratic fashion.

EXAMPLES

General Methods

Procedures for phosphorylations, ligations and transformations are well known in the art. Techniques suitable for use in the following examples may be found in Sambrook, J. et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters, 50 amp is 50 µg/mL ampicillin, and LB-50 amp is Luria-Bertani broth containing 50 µg/mL ampicillin.

Within the tables the following abbreviations are used. "Con." is conversion, "Sel." is selectivity based on carbon, and "nd" is not detected.

Strains and vectors used and constructed in the following examples are listed in the chart below:

| STRAIN/PLASMID | DELETION | ORF/GENE |
|---|---|---|
| KLP23 | gldA | |
| | glpK | |
| RJ8m | gldA | |
| | glpK | |
| | Tpi | |
| pAH48 | | GPP2 |
| | | DAR1 |
| pDT29 | | dhaR |
| | | orfY |
| | | dhaT |
| | | orfX |
| | | orfW |
| | | dhaB1 |
| | | dhaB2 |
| | | dhaB3 |
| | | orfZ |
| pKP32 | | dhaR |
| | | orfY |
| | | orfX |
| | | orfW |
| | | dhaB1 |
| | | dhaB2 |
| | | dhaB3 |
| | | orfZ |

Enzyme Assays

Assays for Dehydratase Enzymes:

Dehydratase activity in cell-free extracts was determined using either glycerol or 1,2-propanediol as substrate. Typically, cell-free extracts were prepared by cell disruption using a french press followed by centrifugation of the cellular debris. The assay, based on the reaction of aldehydes with methylbenzo-2-thiazolone hydrazone, has been described by Forage and Foster (*Biochim. Biophys. Acta* 569, 249 (1979)).

Honda et al. (*J. Bacteriol.* 143, 1458 (1980)) disclose an assay that measures the reactivation of dehydratases. Dehydratase activity was determined in toluenized whole cells, with and without ATP, using either glycerol or 1,2-propanediol as substrate. Reactivation was determined by the ratio of product formation with versus without the ATP addition. Product formation (3-HPA or propionaldehyde when glycerol or 1,2-propanediol is used as substrate, respectively) was measured directly, using HPLC, or indirectly, using the methylbenzo-2-thiazolone hydrazone reagent. Alternatively, product formation was determined by coupling the conversion of the aldehyde to its respective alcohol using a NADH linked alcohol dehydrogenase and monitoring the disappearance of NADH.

Assays for 1,3-propanediol Oxidoreductase:

The activity of 1,3-propanediol oxidoreductase, sometimes referred to as 1,3-propanediol dehydrogenase, was determined for cell-free extracts in solution or in slab gels using 1,3-propanediol and NAD$^+$ as substrates has been described (Johnson and Lin, *J. Bacteriol.* 169, 2050 (1987)). Alternatively, the conversion of 3-HPA and NADH to 1,3-propanediol and NAD$^+$ was determined by the disappearance of NADH. The slab gel assay has the potential advantage of separating the activity of 1,3-propanediol oxidoreductase (dhaT) from that of non-specific alcohol dehydrogenases by virtue of size separation. The native molecular weights of 1,3-propanediol oxidoreductases (dhaT) from *Citrobacter frendii*, *Klebsiella pneumoniae*, and *Clostridium pasteurianum* are unusually large, on the order of 330,000 to 440,000 daltons. *Lactobacillus brevis* and *Lactobacillus buchneri* contain dehydratase associated 1,3-propanediol oxidoreductases with properties similar to those of known 1,3-propanediol oxidoreductases (dhaT).

Assays for Glycerol 3-phosphate Dehydrosenase Activity:

A procedure was used as modified below from a method published by Bell et al. (*J. Biol. Chem.* 250, 7153 (1975)). This method involved incubating a cell-free extract sample in a cuvette that contained 0.2 mM NADH, 2.0 mM dihydroxyacetone phosphate (DHAP), and enzyme in 0.1 M Tris/HCl, pH 7.5 buffer with 5 mM DTT, in a total volume of 1.0 mL at 30° C. A background rate of the reaction of enzyme and NADH was first determined at 340 nm for at least 3 min. The second substrate, DHAP, was subsequently added and the absorbance change over time was further monitored for at least 3 min. G3PDH activity was defined by subtracting the background rate from the gross rate.

Assay for Glycerol-3-phosphatase Activity:

The assay for enzyme activity was performed by incubating the extract with an organic phosphate substrate in a bis-Tris or MES and magnesium buffer, pH 6.5. The substrate used was either l-α-glycerol phosphate, or d,l-α-glycerol phosphate. The final concentrations of the reagents in the assay are: buffer (20 mM, bis-Tris or 50 mM MES); MgCl$_2$ (10 mM); and substrate (20 mM). If the total protein in the sample was low and no visible precipitation occurs with an acid quench, the sample was conveniently assayed in the cuvette. This method involved incubating an enzyme sample in a cuvette that contained 20 mM substrate (50 μL, 200 mM), 50 mM MES, 10 mM MgCl$_2$, pH 6.5 buffer. The final phosphatase assay volume was 0.5 mL. The enzyme-containing sample was added to the reaction mixture; the contents of the cuvette were mixed and then the cuvette was placed in a circulating water bath at T=37° C. for 5 to 120 min, the length of time depending on whether the phosphatase activity in the enzyme sample ranged from 2 to 0.02 U/mL. The enzymatic reaction was quenched by the addition of the acid molybdate reagent (0.4 mL). After the Fiske SubbaRow reagent (0.1 mL) and distilled water (1.5 mL) were added, the solution was mixed and allowed to develop. After 10 min, to allow full color development, the absorbance of the samples was read at 660 nm using a Cary 219 UV/vis spectrophotometer. The amount of inorganic phosphate released was compared to a standard curve that was prepared by using a stock inorganic phosphate solution (0.65 mM) and preparing 6 standards with final inorganic phosphate concentrations ranging from 0.026 to 0.130 μmol/mL.

Assay for Glycerol Kinase Activity:

An appropriate amount of enzyme, typically a cell-free crude extract, was added to a reaction mixture containing 40 mM ATP, 20 mM MgSO$_4$, 21 mM uniformly $^{13}$C labelled glycerol (99%, Cambridge Isotope Laboratories), and 0.1 M Tris-HCl, pH 9 for 75 min at 25° C. The conversion of glycerol to glycerol 3-phosphate was detected by $^{13}$C-NMR (125 MHz): glycerol (63.11 ppm, δ, J=41 Hz and 72.66 ppm, t, J=41 Hz); glycerol 3-phosphate (62.93 ppm, δ, J=41 Hz; 65.31 ppm, br d, J=43 Hz; and 72.66 ppm, dt, J=6, 41 Hz).

NADH-Linked Glycerol Dehydrogenase Assay:

NADH-linked glycerol dehydrogenase activity (gldA) in cell-free extracts from *E. coli* strains was determined after protein separation by non-denaturing polyacrylamide gel electrophoresis. The conversion of glycerol plus NAD$^+$ to dihydroxyacetone plus NADH was coupled with the conversion of 3-[4,5-dimethylthiazol-2-yl]-2,5-diphenyltetrazolium bromide (MTT) to a deeply colored formazan, using phenazine methosulfate (PMS) as mediator (Tang et al., *J. Bacteriol.* 140, 182 (1997)).

Electrophoresis was performed in duplicate by standard procedures using native gels (8–16% TG, 1.5 mm, 15 lane gels from Novex, San Diego, Calif.). Residual glycerol was removed from the gels by washing 3× with 50 mM Tris or potassium carbonate buffer, pH 9 for 10 min. The duplicate gels were developed, with and without glycerol (approximately 0.16 M final concentration), in 15 mL of assay solution containing 50 mM Tris or potassium carbonate, pH 9, 60 mg ammonium sulfate, 75 mg NAD$^+$, 1.5 mg MTT, and 0.5 mg PMS.

The presence or absence of NADH-linked glycerol dehydrogenase activity in *E. coli* strains (glda) was also determined, following polyacrylamide gel electrophoresis, by reaction with polyclonal antibodies raised to purified *K. pneumoniae* glycerol dehydrogenase (dhaD).

Isolation and Identification of 1,3-propanediol:

The conversion of glycerol to 1,3-propanediol was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N H$_2$SO$_4$ as mobile phase at a flow rate of 0.5 mL/min. When quantitative analysis was desired, samples were prepared with a known amount of trimethylacetic acid as external standard. Typically, the retention times of glucose (RI detection), glycerol, 1,3-propanediol (RI detection), and trimethylacetic acid (UV and RI detection) were 15.27 min, 20.67 min, 26.08 min, and 35.03 min, respectively.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated were compared to that of authentic 1,3-propanediol (m/e: 57, 58).

An alternative method for GC/MS involved derivatization of the sample. To 1.0 mL of sample (e.g., culture supernatant) was added 30 μL of concentrated (70% v/v) perchloric acid. After mixing, the sample was frozen and lyophilized. A 1:1 mixture of bis(trimethylsilyl)trifluoroacetamide:pyridine (300 μL) was added to the lyophilized material, mixed vigorously and placed at 65° C. for one h. The sample was clarified of insoluble material by centrifugation. The resulting liquid partitioned into two phases, the upper of which was used for analysis. The sample was chromatographed on a DB-5 column (48 m, 0.25 mm I.D., 0.25 μm film thickness; from J&W Scientific) and the retention time and mass spectrum of the 1,3-propanediol derivative obtained from culture supernatants were compared to that obtained from authentic standards. The mass spectra of TMS-derivatized 1,3-propanediol contains the characteristic ions of 205, 177, 130 and 115 AMU.

Cell Lysis:

Cell lysis was estimated by measuring the extracellular soluble protein concentration in the fermentation broth. Fermenter samples were centrifuged in a desktop centrifuge (typically, 3–5 min at 12,000 rpm in an Eppendorf, Model 5415C micro centrifuge) in order to separate cells. The resulting supernatant was analyzed for protein concentration by the Bradford method using a commercially available reagent (Bio-Rad Protein Assay, Bio-Rad, Hercules, Calif.).

Viability:

Cell viability was determined by plating, at appropriate dilutions, cells obtained from the fermenter on non-selective LB agar plates. Cell viability between fermenter experiments is compared by using the ratio of viable cells per mL of fermenter broth divided by OD550 (AU).

Example 1

Cloning and Transformation of *E. coli* Host Cells with Cosmid DNA for the Expression of 1,3-propanediol Media:

Synthetic S12 medium was used in the screening of bacterial transformants for the ability to make 1,3-propanediol. S12 medium contains: 10 mM ammonium sulfate, 50 mM potassium phosphate buffer, pH 7.0, 2 mM $MgCl_2$, 0.7 mM $CaCl_2$, 50 μM $MnCl_2$, 1 μM $FeCl_3$, 1 μM ZnCl, 1.7 μM $CuSO_4$, 2.5 μM $CoCl_2$, 2.4 μM $Na_2MoO_4$, and 2 μM thiamine hydrochloride.

Medium A used for growth and fermentation consisted of: 10 mM ammonium sulfate; 50 mM MOPS/KOH buffer, pH 7.5; 5 mM potassium phosphate buffer, pH 7.5; 2 mM $MgCl_2$; 0.7 mM $CaCl_2$; 50 μM $MnCl_2$; 1 μM $FeCl_3$; 1 μM ZnCl; 1.72 μM $CuSO_4$; 2.53 μM $CoCl_2$; 2.42 μM $Na_2MoO_4$; 2 μM thiamine hydrochloride; 0.01% yeast extract; 0.01% casamino acids; 0.8 μg/mL vitamin $B_{12}$; and 50 μg/mL amp. Medium A was supplemented with either 0.2% glycerol or 0.2% glycerol plus 0.2% D-glucose as required.

Cells:

*Klebsiella pneumoniae* ECL2106 (Ruch et al., *J. Bacteriol.* 124, 348 (1975)), also known in the literature as *K. aerogenes* or *Aerobacter aerogenes*, was obtained from E. C. C. Lin (Harvard Medical School, Cambridge, Mass.) and was maintained as a laboratory culture.

*Klebsiella pneumoniae* ATCC 25955 was purchased from American Type Culture Collection (Manassas, Va.).

*E. coli* DH5α was purchased from Gibco/BRL and was transformed with the cosmid DNA isolated from *Klebsiella pneumoniae* ATCC 25955 containing a gene coding for either a glycerol or diol dehydratase enzyme. Cosmids containing the glycerol dehydratase were identified as pKP1 and pKP2 and cosmid containing the diol dehydratase enzyme were identified as pKP4. Transformed DH5α cells were identified as DH5α-pKP1, DH5α-pKP2, and DH5α-pKP4.

*E. coli* ECL707 (Sprenger et al., *J. Gen. Microbiol.* 135, 1255 (1989)) was obtained from E. C. C. Lin (Harvard Medical School, Cambridge, Mass.) and was similarly transformed with cosmid DNA from *Klebsiella pneumoniae*. These transformants were identified as ECL707-pKP1 and ECL707-pKP2, containing the glycerol dehydratase gene and ECL707-pKP4 containing the diol dehydratase gene.

*E. coli* AA200 containing a mutation in the tpi gene (Anderson et al., *J. Gen. Microbiol.* 62, 329 (1970)) was purchased from the *E. coli* Genetic Stock Center, Yale University (New Haven, Conn.) and was transformed with *Klebsiella* cosmid DNA to give the recombinant microorganisms AA200-pKP1 and AA200-pKP2, containing the glycerol dehydratase gene, and AA200-pKP4, containing the diol dehydratase gene.

DH5α:

Six transformation plates containing approximately 1,000 colonies of *E. coli* XL1-Blue MR transfected with *K. pneumoniae* DNA were washed with 5 mL LB medium and centrifuged. The bacteria were pelleted and resuspended in 5 mL LB medium+glycerol. An aliquot (50 μL) was inoculated into a 15 mL tube containing S12 synthetic medium with 0.2% glycerol+400 ng per mL of vitamin $B_{12}$+0.001% yeast extract+50 amp. The tube was filled with the medium to the top and wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production, were serially diluted and plated onto LB-50 amp plates in order to isolate single colonies. Forty-eight single colonies were isolated and checked again for the production of 1,3-propanediol. Cosmid DNA was isolated from 6 independent clones and transformed into *E. coli* strain DH5α. The transformants were again checked for the production of 1,3-propanediol. Two transformants were characterized further and designated as DH5α-pKP1 and DH5α-pKP2.

A 12.1 kb EcoRI-SalI fragment from pKP1, subcloned into pIBI31 (IBI Biosystem, New Haven, Conn.), was sequenced and termed pHK28-26 (SEQ ID NO:1). Sequencing revealed the loci of the relevant open reading frames of the dha operon encoding glycerol dehydratase and genes necessary for regulation. Referring to SEQ ID NO:1, a fragment of the open reading frame for dhaK1 encoding dihydroxyacetone kinase is found at bases 1–399 (complement); the open reading frame dhaD encoding glycerol dehydrogenase is found at bases 1010–2107; the open reading frame dhaR encoding the repressor is found at bases 2209–4134; the open reading frame orfW, encoding a protein of unknown function is found at bases 4112–4642 (complement); the open reading frame orfX encoding a dehydratase reactivation protein is found at bases 4643–4996 (complement); the open reading frame dhaT encoding 1,3-propanediol oxidoreductase is found at bases 5017–6180 (complement); the open reading frame orfY, encoding a protein of unknown function is found at bases 6202–6630 (complement); the open reading frame dhaB1 encoding the alpha subunit glycerol dehydratase is found at bases 7044–8711; the open reading frame dhaB2 encoding the beta subunit glycerol dehydratase is found at bases 8724–9308; the open reading frame dhaB3 encoding the gamma subunit glycerol dehydratase is found at bases 9311–9736; the open reading frame dhaBX, encoding a dehydratase reactivation protein is found at bases 9749–11572; and a fragment of the open reading frame for glpF encoding a glycerol uptake facilitator protein is found at bases 11626–12145.

Single colonies of E. coli XL1-Blue MR transfected with packaged cosmid DNA from K. pneumoniae were inoculated into microtiter wells containing 200 µL of S15 medium (ammonium sulfate, 10 mM; potassium phosphate buffer, pH 7.0, 1 mM; MOPS/KOH buffer, pH 7.0, 50 mM; $MgCl_2$, 2 mM; $CaCl_2$, 0.7 mM; $MnCl_2$, 50 µM; $FeCl_3$, 1 µM; ZnCl, 1 µM; $CuSO_4$, 1.72 µM; $CoCl_2$, 2.53 µM; $Na_2MoO_4$, 2.42 µM; and thiamine hydrochloride, 2 µM)+0.2% glycerol+400 ng/mL of vitamin $B_{12}$+0.001% yeast extract+50 µg/mL ampicillin. In addition to the microtiter wells, a master plate containing LB-50 amp was also inoculated. After 96 h, 100 µL was withdrawn and centrifuged in a Rainin microfuge tube containing a 0.2 micron nylon membrane filter. Bacteria were retained and the filtrate was processed for HPLC analysis. Positive clones demonstrating 1,3-propanediol production were identified after screening approximately 240 colonies. Three positive clones were identified, two of which had grown on LB-50 amp and one of which had not. A single colony, isolated from one of the two positive clones grown on LB-50 amp and verified for the production of 1,3-propanediol, was designated as pKP4. Cosmid DNA was isolated from E. coli strains containing pKP4 and E. coli strain DH5α was transformed. An independent transformant, designated as DH5α-pKP4, was verified for the production of 1,3-propanediol.

ECL707:

E. coli strain ECL707 was transformed with cosmid K. pneumoniae DNA corresponding to one of pKP1, pKP2, pKP4 or the Supercos vector alone and named ECL707-pKP1, ECL707-pKP2, ECL707-pKP4, and ECL707-sc, respectively. ECL707 is defective in glpK, gld, and ptsD which encode the ATP-dependent glycerol kinase, $NAD^+$-linked glycerol dehydrogenase, and enzyme II for dihydroxyacetone of the phosphoenolpyruvate-dependent phosphotransferase system, respectively.

Twenty single colonies of each cosmid transformation and five of the Supercos vector alone (negative control) transformation, isolated from LB-50 amp plates, were transferred to a master LB-50 amp plate. These isolates were also tested for their ability to convert glycerol to 1,3-propanediol in order to determine if they contained dehydratase activity. The transformants were transferred with a sterile toothpick to microtiter plates containing 200 µL of Medium A supplemented with either 0.2% glycerol or 0.2% glycerol plus 0.2% D-glucose. After incubation for 48 h at 30° C., the contents of the microtiter plate wells were filtered through a 0.45 micron nylon filter and chromatographed by HPLC. The results of these tests are given in Table 2.

TABLE 2

Conversion of glycerol to 1,3-propanediol by transformed ECL707

| transformant | glycerol* | glycerol plus glucose* |
|---|---|---|
| ECL707-pKP1 | 19/20 | 19/20 |
| ECL707-pKP2 | 18/20 | 20/20 |
| ECL707-pKP4 | 0/20 | 20/20 |
| ECL707-sc | 0/5 | 0/5 |

*(Number of positive isolates/number of isolates tested)

AA200:

E. coli strain AA200 was transformed with cosmid K. pneumoniae DNA corresponding to one of pKP1, pKP2, pKP4 and the Supercos vector alone and named AA200-pKP1, AA200-pKP2, AA200-pKP4, and AA200-sc, respectively. Strain AA200 is defective in triosephosphate isomerase ($tpi^-$).

Twenty single colonies of each cosmid transformation and five of the empty vector transformation were isolated and tested for their ability to convert glycerol to 1,3-propanediol as described for E. coli strain ECL707. The results of these tests are given in Table 3.

TABLE 3

Conversion of glycerol to 1,3-propanediol by transformed AA200

| transformant | glycerol* | glycerol plus glucose* |
|---|---|---|
| AA200-pKP1 | 17/20 | 17/20 |
| AA200-pKP2 | 17/20 | 17/20 |
| AA200-pKP4 | 2/20 | 16/20 |
| AA200-sc | 0/5 | 0/5 |

*(Number of positive isolates/number of isolates tested)

Example 2

Engineering of Glycerol Kinase Mutants of E. coli FM5 for Production of Glycerol from Glucose Construction of Integration Plasmid for Glycerol Kinase Gene Replacement in E. coli FM5:

E. coli FM5 (ATCC 53911) genomic DNA was prepared using the Puregene DNA Isolation Kit (Gentra Systems, Minneapolis, MN). A 1.0 kb DNA fragment containing partial glpF and glycerol kinase (glpK) genes was amplified by PCR (Mullis and Faloona, Methods Enzymol. 155, 335 (1987)) from FM5 genomic DNA using primers SEQ ID NO:2 and SEQ ID NO:3. A 1.1 kb DNA fragment containing partial glpK and glpX genes was amplified by PCR from FM5 genomic DNA using primers SEQ ID NO:4 and SEQ ID NO:5. A MunI site was incorporated into primer SEQ ID NO:4. The 5' end of primer SEQ ID NO:4 was the reverse complement of primer SEQ ID NO:3 to enable subsequent overlap extension PCR. The gene splicing by overlap extension technique (Horton et al., BioTechniques 8, 528 (1990)) was used to generate a 2.1 kb fragment by PCR using the above two PCR fragments as templates and primers SEQ ID NO:2 and SEQ ID NO:5. This fragment represented a deletion of 0.8 kb from the central region of the 1.5 kb glpK gene. Overall, this fragment had 1.0 kb and 1.1 kb flanking regions on either side of the MunI cloning site (within the partial glpK) to allow for chromosomal gene replacement by homologous recombination.

The above 2.1 kb PCR fragment was blunt-ended (using mung bean nuclease) and cloned into the pCR-Blunt vector using the Zero Blunt PCR Cloning Kit (Invitrogen, San Diego, Calif.) to yield the 5.6 kb plasmid pRN100 containing kanamycin and Zeocin resistance genes. The 1.2 kb HincII fragment from pLoxCat1 (unpublished results), containing a chloramphenicol-resistance gene flanked by bacteriophage P1 loxP sites (Snaith et al., Gene 166, 173 (1995)), was used to interrupt the glpK fragment in plasmid pRN100 by ligating it to MunI-digested (and blunt-ended) plasmid pRN100 to yield the 6.9 kb plasmid pRN101-1. A 376 bp fragment containing the R6K origin was amplified by PCR from the vector pGP704 (Miller and Mekalanos, J. Bacteriol. 170, 2575–2583 (1988)) using primers SEQ ID NO:6 and SEQ ID NO:7, blunt-ended, and ligated to the 5.3 kb, Asp718-AatII fragment (which was blunt-ended) from pRN101-1 to yield the 5.7 kb plasmid pRN102-1 containing kanamycin and chloramphenicol resistance genes. Substitution of the ColE1 origin region in pRN101-1 with the R6K origin to generate pRN102-1 also involved deletion of most of the Zeocin resistance gene. The host for pRN102-1 replication was E. coli SY327 (Miller and Mekalanos, J. Bacteriol. 170, 2575–2583 (1988)) which contains the pir gene necessary for the function of the R6K origin.

Engingering of Glycerol Kinase Mutant RJF10m with Chloramphenicol Resistance Gene Interrupt:

E. coli FM5 was electrotransformed with the non-replicative integration plasmid pRN102-1 and transformants that were chloramphenicol-resistant (12.5 μg/mL) and kanamycin-sensitive (30 μg/mL) were further screened for glycerol non-utilization on M9 minimal medium containing 1 mM glycerol. An EcoRI digest of genomic DNA from one such mutant, RJF10m, when probed with the intact glpK gene via Southern analysis (Southern, J. Mol. Biol. 98, 503–517 (1975)) indicated that it was a double-crossover integrant (glpK gene replacement) since the two expected 7.9 kb and 2.0 kb bands were observed, owing to the presence of an additional EcoRI site within the chloramphenicol resistance gene. The wild-type control yielded the single expected 9.4 kb band. A $^{13}$C NMR analysis of mutant RJF10m confirmed that it was incapable of converting $^{13}$C-labeled glycerol and ATP to glycerol-3-phosphate. This glpK mutant was further analyzed by genomic PCR using primer combinations SEQ ID NO:8 and SEQ ID NO:9, SEQ ID NO:10 and SEQ ID NO:11, and SEQ ID NO:8 and SEQ ID NO:11 which yielded the expected 2.3 kb, 2.4 kb, and 4.0 kb PCR fragments respectively. The wild-type control yielded the expected 3.5 kb band with primers SEQ ID NO:8 and SEQ ID NO:11. The glpK mutant RTF10m was electrotransformed with plasmid pAH48 to allow glycerol production from glucose. The glpK mutant E. coli RJF10m has been deposited with ATCC under the terms of the Budapest Treaty on Nov. 24, 1997.

Engineering of Glycerol Kinase Mutant RJF10 with Chloramphenicol Resistance Gene Interrupt Removed:

After overnight growth on YENB medium (0.75% yeast extract, 0.8% nutrient broth) at 37° C., E. coli RJF10m in a water suspension was electrotransformed with plasmid pJW168 (unpublished results), which contained the bacteriophage P1 Cre recombinase gene under the control of the IPTG-inducible lacUV5 promoter, a temperature-sensitive pSC101 replicon, and an ampicillin resistance gene. Upon outgrowth in SOC medium at 30° C., transformants were selected at 30° C. (permissive temperature for pJW168 replication) on LB agar medium supplemented with carbenicillin (50 μg/mL) and IPTG (1 mM). Two serial overnight transfers of pooled colonies were carried out at 30° C. on fresh LB agar medium supplemented with carbenicillin and IPTG in order to allow excision of the chromosomal chloramphenicol resistance gene via recombination at the loxP sites mediated by the Cre recombinase (Hoess and Abremski, J. Mol. Biol. 181, 351–362(1985)). Resultant colonies were replica-plated on to LB agar medium supplemented with carbenicillin and IPTG and LB agar supplemented with chloramphenicol (12.5 μg/mL) to identify colonies that were carbenicillin-resistant and chloramphenicol-sensitive indicating marker gene removal. An overnight 30° C. culture of one such colony was used to inoculate 10 mL of LB medium. Upon growth at 30° C. to OD (600 nm) of 0.6 AU, the culture was incubated at 37° C. overnight. Several dilutions were plated on prewarmed LB agar medium and the plates incubated overnight at 42° C. (the non-permissive temperature for pJW168 replication). Resultant colonies were replica-plated on to LB agar medium and LB agar medium supplemented with carbenicillin (75 μg/mL) to identify colonies that were carbenicillin-sensitive indicating loss of plasmid pJW168. One such glpK mutant, RJF10, was further analyzed by genomic PCR using primers SEQ ID NO:8 and SEQ ID NO:11 and yielded the expected 3.0 kb band confirming marker gene excision. Glycerol non-utilization by mutant RJF10 was confirmed by lack of growth on M9 minimal medium containing 1 mM glycerol. The glpK mutant RJF10 was electrotransformed with plasmid pAH48 to allow glycerol production from glucose.

Example 3

Construction of E. coli Strain with gldA Gene Knockout

The gldA gene was isolated from E. coli by PCR (K. B. Mullis and F. A. Faloona, Meth. Enzymol. 155, 335–350 (1987)) using primers SEQ ID NO:12 and SEQ ID NO:13, which incorporate terminal Sph1 and Xba1 sites, respectively, and cloned (T. Maniatis (1982) Molecular Cloning: A Laboratory Manual. Cold Spring Harbor, Cold Spring Harbor, N.Y.) between the Sph1 and Xba1 sites in pUC18, to generate pKP8. pKP8 was cut at the unique Sal1 and Nco1 sites within the gldA gene, the ends flushed with Klenow and religated, resulting in a 109 bp deletion in the middle of gldA and regeneration of a unique Sal1 site, to generate pKP9. A 1.4 kb DNA fragment containing the gene conferring kanamycin resistance (kan), and including about 400 bps of DNA upstream of the translational start codon and about 100 bps of DNA downstream of the translational stop codon, was isolated from pET-28a(+) (Novagen, Madison, Wis.) by PCR using primers SEQ ID NO:14 and SEQ ID NO:15, which incorporate terminal Sal1 sites, and subcloned into the unique Sal1 site of pKP9, to generate pKP13. A 2.1 kb DNA fragment beginning 204 bps downstream of the gldA translational start codon and ending 178 bps upstream of the gldA translational stop codon, and containing the kan insertion, was isolated from pKP13 by PCR using primers SEQ ID NO:16 and SEQ ID NO:17, which incorporate terminal Sph1 and Xba1 sites, respectively, was subcloned between the Sph1 and Xba1 sites in pMAK705 (Genencor International, Palo Alto, Calif.), to generate pMP33. E. coli FM5 was transformed with pMP33 and selected on 20 μg/mL kan at 30° C., which is the permissive temperature for pMAK705 replication. One colony was expanded overnight at 30° C. in liquid media supplemented with 20 μg/mL kan. Approximately 32,000 cells were plated on 20 μg/mL kan and incubated for 16 h at 44° C., which is the restrictive temperature for pMAK705 replication. Transformants growing at 44° C. have plasmid integrated into the chromosome, occurring at a frequency of approximately 0.0001. PCR and Southern blot (E. M. Southern, *J. Mol. Biol.* 98, 503–517 (1975)) analyses were used to determine the nature of the chromosomal integration events in the transformants. Western blot analysis (Towbin et al., *Proc. Natl. Acad. Sci.* 76, 4350 (1979)) was used to determine whether glycerol dehydrogenase protein, the product of gldA, is produced in the transformants. An activity assay was used to determine whether glycerol dehydrogenase activity remained in the transformants. Activity in glycerol dehydrogenase bands on native gels was determined by coupling the conversion of glycerol plus NAD$^+$ to dihydroxyacetone plus NADH to the conversion of a tetrazolium dye, MTT [3-(4,5-dimethylthiazol-2-yl)-2,5-diphenyltetrazolium bromide] to a deeply colored formazan, with phenazine methosulfate as mediator. Glycerol dehydrogenase also requires the presence of 30 mM ammonium sulfate and 100 mM Tris, pH 9 (Tang et al., *J. Bacteriol.* 140, 182 (1997)). Of 8 transformants analyzed, 6 were determined to be gldA knockouts. *E. coli* MSP33.6 has been deposited with ATCC under the terms of the Budapest Treaty on Nov. 24, 1997.

Example 4

Construction of an *E. coli* Strain with glpK and gldA Gene Knockouts

A 1.6 kb DNA fragment containing the gldA gene and including 228 bps of DNA upstream of the translational start codon and 220 bps of DNA downstream of the translational stop codon was isolated from *E. coli* by PCR using primers SEQ ID NO:18 and SEQ ID NO:19, which incorporate terminal Sph1 and Xba1 sites, respectively, and cloned between the Sph1 and Xba1 sites of pUC18, to generate pQN2. pQN2 was cut at the unique Sal1 and Nco1 sites within the gldA gene, the ends flushed with Klenow and religated, resulting in a 109 bps deletion in the middle of gldA and regeneration of a unique Sal1 site, to generate pQN4. A 1.2 kb DNA fragment containing the gene conferring kanamycin resistance (kan), and flanked by loxP sites was isolated from pLoxKan2 (Genencor International, Palo Alto, Calif.) as a Stu1/Xho1 fragment, the ends flushed with Klenow, and subcloned into pQN4 at the Sal1 site after flushing with Klenow, to generate pQN8. A 0.4 kb DNA fragment containing the R6K origin of replication was isolated from pGP704 (Miller and Mekalanos, *J. Bacteriol.* 170, 2575–2583 (1988)) by PCR using primers SEQ ID NO:20 and SEQ ID NO:21, which incorporate terminal Sph1 and Xba1 sites, respectively, and ligated to the 2.8 kb Sph1/Xba1 DNA fragment containing the gldA::kan cassette from pQN8, to generate pKP22. A 1.0 kb DNA fragment containing the gene conferring chloramphenicol resistance (cam), and flanked by loxP sites was isolated from pLoxCat2 (Genencor International, Palo Alto, Calif.) as an Xba1 fragment, and subcloned into pKP22 at the Xba1 site, to generate pKP23. *E. coli* strain RJF10 (see Example 2), which is glpK-, was transformed with pKP23 and transformants with the phenotype kanRcamS were isolated, indicating double crossover integration, which was confirmed by southern blot analysis. Glycerol dehydrogenase gel activity assays (as described in Example 3) demonstrated that active glycerol dehydrogenase was not present in these transformants. The kan marker was removed from the chromosome using the Cre-producing plasmid pJW168, as described in Example 2, to produce strain KLP23. Several isolates with the phenotype-kanS demonstrated no glycerol dehydrogenase activity, and southern blot analysis confirmed loss of the kan marker.

Example 5

Plasmid Construction and Strain Construction for the Expression of Glycerol 3-phosphate Dehydrogenase (DAR1) and/or Glycerol 3-phosphatase (GPP2)

Construction of Expression Cassettes for Glycerol 3-phosphatase (gpp2):

The *Saccharomyces cerevisiae* chromosomeV lamda clone 6592 (GenBank, accession # U18813x11) was obtained from ATCC. The glycerol 3-phosphate phosphatase gene (GPP2) was cloned by cloning from the lamda clone as target DNA using synthetic primers (SEQ ID NO:22 with SEQ ID NO:23) incorporating an BamHI-RBS-XbaI site at the 5' end and a SmaI site at the 3' end. The product was subcloned into pCR-Script (Stratagene, Madison, Wis.) at the SrfI site to generate the plasmid pAH15 containing GPP2. The plasmid pAH15 contains the GPP2 gene in the inactive orientation for expression from the lac promoter in pCR-Script SK+. The BamHI-SmaI fragment from pAH15 containing the GPP2 gene was inserted into pBlueScriptII SK+ to generate plasmid pAH19. The pAH19 contains the GPP2 gene in the correct orientation for expression from the lac promoter. The XbaI-PstI fragment from pAH19 containing the GPP2 gene was inserted into pPHOX2 to create plasmid pAH21. The pAH21/DH5α is the expression plasmid.

Construction of Expression Cassettes for Glycerol 3-phosphate Dehydrogenase (DAR1):

DAR1 was isolated by PCR cloning from genomic *S. cerevisiae* DNA using synthetic primers (SEQ ID NO:24 with SEQ ID NO:25). Successful PCR cloning places an NcoI site at the 5' end of DAR1 where the ATG within NcoI is the DAR1 initiator methionine. At the 3' end of DAR1 a BamHI site is introduced following the translation terminator. The PCR fragments were digested with NcoI+BamHI and cloned into the same sites within the expression plasmid pTrc99A (Pharmacia, Piscataway, N.J.) to give pDAR1A.

In order to create a better ribosome binding site at the 5' end of DAR1, an SpeI-RBS-NcoI linker obtained by annealing synthetic primers (SEQ ID NO:26 with SEQ ID NO:27) was inserted into the NcoI site of pDAR1A to create pAH40. Plasmid pAH40 contains the new RBS and DAR1 gene in the correct orientation for expression from the trc promoter of pTrc99A (Pharmacia, Piscataway, N.J.). The NcoI-BamHI fragment from pDAR1A and an second set of SpeI-RBS-NcoI linker obtained by annealing synthetic primers (SEQ ID NO:28 with SEQ ID NO:29) was inserted into the SpeI-BamHI site of pBC-SK+ (Stratagene, Madison, Wis.) to create plasmid pAH42. The plasmid pAH42 contains a chloramphenicol resistant gene.

Construction of Expression Cassettes for dar1 and gpp2:

Expression cassettes for DAR1 and GPP2 were assembled from the individual DAR1 and GPP2 subclones described above using standard molecular biology methods. The BamHI-PstI fragment from pAH19 containing the ribosomal binding site (RBS) and GPP2 gene was inserted into pAH40 to create pAH43. The BamHI-PstI fragment from pAH19 containing the RBS and GPP2 gene was inserted into pAH42 to create pAH45.

The ribosome binding site at the 5' end of GPP2 was modified as follows. A BamHI-RBS-SpeI linker, obtained by annealing synthetic primers GATCCAGGAAACAGA (SEQ ID NO:30) with CTAGTCTGTTTCCTG (SEQ ID NO:31) to the XbaI-PstI fragment from pAH19 containing the GPP2 gene, was inserted into the BamHI-PstI site of pAH40 to create pAH48. Plasmid pAH48 contains the DAR1 gene, the modified RBS, and the GPP2 gene in the correct orientation for expression from the trc promoter of pTrc99A (Pharmacia, Piscataway, N.J.).

Transformation of E. coli:

The plasmids described here were transformed into E. coli DH5α, FM5 and KLP23 using standard molecular biology techniques. The transformants were verified by their DNA RFLP pattern.

Example 6

Construction of Expression Plasmids for Use in Transformation of *Escherichia coli* with Genes from the *Klebsiella pneumoniae* dha Regluon Construction of the Expression Vector pTacIQ:

The E. coli expression vector pTacIQ was prepared by inserting lacIq gene (Farabaugh, Nature 274(5673), 765–769 (1978)) and tac promoter (Amann et al., Gene 25, 167–178 (1983)) into the restriction endonuclease site EcoRI of pBR322 (Sutcliffe, Cold Spring Harb. Symp. Quant. Biol. 43, 77–90 (1979)). A multiple cloning site and terminator sequence (SEQ ID NO:32) replaces the pBR322 sequence from EcoRI to SphI.

Subcloning the Glycerol Dehydratase Genes (dhaB1,2,3, X):

The open reading frame for the dhaB3 gene was amplified from pHK28-26 by PCR using primers (SEQ ID NO:33 and SEQ ID NO:34) incorporating an EcoRI site at the 5' end and a XbaI site at the 3' end. The product was subcloned into pLitmus29 (New England Biolab, Inc., Beverly, Mass.) to generate the plasmid pDHAB3 containing dhaB3.

The region containing the entire coding region for dhaB1, dhaB2, dhaB3 and dhaBX of the dhaB operon from pHK28-26 was cloned into pBluescriptIIKS+ (Stratagene, La Jolla, Calif.) using the restriction enzymes KpnI and EcoRI to create the plasmid pM7.

The dhaBX gene was removed by digesting plasmid pM7 with ApaI and XbaI, purifying the 5.9 kb fragment and ligating it with the 325-bp ApaI-XbaI fragment from plasmid pDHAB3 to create pM11 containing dhaB1, dhaB2 and dhaB3.

The open reading frame for the dhaB1 gene was amplified from pHK28-26 by PCR using primers (SEQ ID NO:35 and SEQ ID NO:36) incorporating a HindIII site and a consensus ribosome binding site at the 5' end and a XbaI site at the 3' end. The product was subcloned into pLitmus28 (New England Biolab, Inc., Beverly, Mass.) to generate the plasmid pDT1 containing dhaB1.

A NotI-XbaI fragment from pM11 containing part of the dhaB1 gene, the dhaB2 gene and the dhaB3 gene was inserted into pDT1 to create the dhaB expression plasmid, pDT2. The HindIII-XbaI fragment containing the dhaB(1, 2,3) genes from pDT2 was inserted into pTacIQ to create pDT3.

Subcloning the 1,3-propanediol Dehydrogenase Gene (dhaT):

The KpnI-SacI fragment of pHK28-26, containing the 1,3-propanediol dehydrogenase (dhaT) gene, was subcloned into pBluescriptII KS+ creating plasmid pAH1. The dhaT gene was amplified by PCR from pAH1 as template DNA and synthetic primers (SEQ ID NO:37 with SEQ ID NO:38) incorporating an XbaI site at the 5' end and a BamHI site at the 3' end. The product was subcloned into pCR-Script (Stratagene) at the SrfI site to generate the plasmids pAH4 and pAH5 containing dhaT. The plasmid pAH4 contains the dhaT gene in the right orientation for expression from the lac promoter in pCR-Script and pAH5 contains dhat gene in the opposite orientation. The XbaI-BamHI fragment from pAH4 containing the dhaT gene was inserted into pTacIQ to generate plasmid pAH8. The HindII-BamHI fragment from pAH8 containing the RBS and dhaT gene was inserted into pBluescriptIIKS+ to create pAH11.

Construction of an Expression Cassette for dhaT and dhaB (1,2,3):

An expression cassette for dhaT and dhaB(1,2,3) was assembled from the individual dhaB(1,2,3) and dhaT subclones described previously using standard molecular biology methods. A SpeI-SacI fragment containing the dhaB(1, 2,3) genes from pDT3 was inserted into pAH11 at the SpeI-SacI sites to create pAH24. A SalI-XbaI linker (SEQ ID NO:39 and SEQ ID NO:40) was inserted into pAH5 that was digested with the restriction enzymes SalI-XbaI to create pDT16. The linker destroys the XbaI site. The 1 kb SalI-MluI fragment from pDT16 was then inserted into pAH24 replacing the existing SalI-MluI fragment to create pDT18. pDT21 was constructed by inserting the SalI-NotI fragment from pDT18 and the NotI-XbaI fragment from pM7 into pCL1920 (SEQ ID NO:41). The glucose isomerase promoter sequence from *Streptomyces* (SEQ ID NO:42) was cloned by PCR and inserted into EcoRI-HinDIII sites of pLitmus28 to construct pDT5. pCL1925 was constructed by inserting EcoRI-PvuII fragment of pDT5 into the EcoRI-PvuI site of pCL1920. pDT24 was constructed by cloning the HinDIII-MluII fragment of pDT21 and the MluI-XbaI fragment of pDT21 into the HinDIII-XbaI sites of pCL1925.

Construction of an Expression Cassette for dhaT and dhaB (1,2,3,X):

pDT21 was constructed by inserting the SalI-NotI fragment from pDT18 and the NotI-XbaI fragment from pM7 into pCL1920 (SEQ ID NO:41). The glucose isomerase promoter sequence from *Streptomyces* (SEQ ID NO:42) was cloned by PCR and inserted into EcoRI-HinDIII sites of pLitmus28 to construct pDT5. pCL1925 was constructed by inserting EcoRI-PvuII fragment of pDT5 into the EcoRI-PvuI site of pCL1920. pDT24 was constructed by cloning the HinDIII-MluII fragment of pDT21 and the MluI-XbaI fragment of pDT21 into the HinDIII-XbaI sites of pCL1925.

Construction of an Expression Cassette for dhaR, orfY, dhaT, orfX, orfW and dhaB(1,2,3,X):

pDT29 was constructed by inserting the SacI-EcoRI fragment of pHK28-26 into SacI-EcoRI sites of pCL1925.

Construction of an Expression Cassette for dhaR, orfY, orfx, orfW and dhaB(1,2,3,X):

A derivative of plasmid pDT29 was constructed in which all except the first 5 and the last 5 codons (plus stop codon) of the gene dhaT were deleted by a technique known as PCR-mediated overlap extension. Using pDT29 as template, 2 primary PCR products were generated using the following primers:

SEQ ID NO:43=5'GAC GCA ACA GTA TTC CGT CGC3';
SEQ ID NO:44=5'ATG AGC TAT CGT ATG TTC CGC CAG GCA TTC TGA GTG TTA ACG3';
SEQ ID NO:45=5'GCC TGG CGG AAC ATA CGA TAG CTC ATA ATA TAC3';
SEQ ID NO:46=5' CGG GCG GCT GGG CCA GTA CTG3'.

SEQ ID NO:45 was paired with SEQ ID NO:46 to generate a product of 931 bps and encompassing nucleic acid including 5' dhaB1 (to unique ScaI site), all of orfY, and the first five codons of dhaT. SEQ ID NO:43 was paired with SEQ ID NO:44 to generate a product of 1348 bps and encompassing nucleic acid including the last five codons (plus stop codon) of dhaT, all of orfX, all of orfW, and 5' dhaR (to unique SapI site). The 15 bases at the 5' end of SEQ ID NO:44 constitute a tail that is the inverse complement of a 15 base portion of SEQ ID NO:45. Similarly, the 11 bases at the 5' end of SEQ ID NO:45 constitute a tail that is the inverse complement of an 11 base portion of SEQ ID NO:44. Thus, the 2 primary PCR products were joined together after annealing (via 26 bp tail overlap) and extending by PCR, to generate a third nucleic acid product of 2253 bps. This third PCR product was digested with SapI and ScaI and ligated into pDT29 which was also digested with SapI and ScaI, to generate the plasmid pKP32, which is identical to pDT29, except for the large, in-frame deletion within dhaT.

Example 7

Conversion of Glucose to 1,3-propanediol Using *E. coli* Strain KLP23/pAH48/pDT29 and the Improved Process Using KLP23/pAH48/pKP32

Pre-Culture:
KLP23/pAH48/pDT29 and KLP23/pAH48/pKP32 were pre-cultured for seeding a fermenter in 2YT medium (10 g/L yeast extract, 16 g/L tryptone, and 10 g/L NaCl) containing 200 mg/L carbenicillin (or ampicillin) and 50 mg/L spectinomycin. KLP23/pAH48/pKP32 is identical to KLP23/pAH48/pDT29 except that dhaT is deleted.

Cultures were started from frozen stocks (10% DMSO as cryoprotectant) in 500 mL of medium in a 2-L Erlenmeyer flask, grown at 35° C. in a shaker at 250 rpm until an $OD_{550}$ of approximately 1.0 AU was reached and used to seed the fermenter.

Fermenter medium:
The following components were sterilized together in the fermenter vessel: 45 g $KH_2PO_4$, 12 g citric acid, 12 g $MgSO_4.7H_2O$, 30 g yeast extract, 2.0 g ferric ammonium citrate, 5 mL Mazu DF204 as antifoam, 1.2 g $CaCl_2.2H_2O$, and 7.3 mL sulfuric acid. The pH was raised to 6.8 with 20–28% $NH_4OH$ and the following components were added: 1.2 g carbenicillin or ampicillin, 0.30 g spectinomycin, 60 mL of a solution of trace elements and glucose (from a 60–67 weight % feed). After inoculation, the volume was 6.0 L and the glucose concentration was 10 g/L. The solution of trace elements contained (g/L): citric acid. $H_2O$ (4.0), $MnSO_4.H_2O$ (3.0), NaCl (1.0), $FeSO_4.7H_2O$ (0.10), $CoCl_2.6H_2O$ (0.10), $ZnSO_4.7H_2O$ (0.10), $CuSO_4.5H_2O$ (0.010), $H_3BO_3$ (0.010), and $Na_2MoO_4.2H_2O$ (0.010).

Fermentation Growth:
A 15 L stirred tank fermenter was prepared with the medium described above. The temperature was controlled at 35° C. and aqueous ammonia (20–28 weight %) was used to control pH at 6.8. Initial values for air flow rate (set to minimum values of between 6 and 12 standard liters per min) and agitator speed (set to minimum values of between 350 and 690 rpm) were set so that dissolved oxygen (DO) control was initiated when OUR values reached approximately 140 mmol/L/h. Back pressure was controlled at 0.5 bar. DO control was set at 10%. Except for minor excursions, glucose was maintained at between 0 g/L and 10 g/L with a 60% or 67% (wt) feed. Vitamin $B_{12}$ or coenzyme $B_{12}$ was added as noted below.

Fermentation with KLP23/PAH48/pDT29:
A representative fermentation summary of the conversion of glucose to 1,3-propanediol (1,3-PD) using *E. coli* strain KLP23/pAH48/pDT29 is given in Table 4. Vitamin $B_{12}$ (0.075 g/L, 500 mL) was fed, starting 3 h after inoculation, at a rate of 16 mL/h. The yield of 1,3-propanediol was 24 wt % (g 1,3-propanediol/g glucose consumed) and a titer of 68 g/L 1,3-propanediol was obtained.

TABLE 4

Representative fermentation summary of the conversion of glucose to 1,3-propanediol (1,3-PD) using *E. coli* strain KLP23/pAH48/pDT29

| Time (h) | OD550 (AU) | DO (%) | Glucose (g/L) | Glycerol (g/L) | 1,3-PD (g/L) |
|---|---|---|---|---|---|
| 0 | 0 | 150 | 12.9 | 0.0 | 0 |
| 6 | 17 | 80 | 8.3 | 3.1 | 1 |
| 12 | 42 | 53 | 2.8 | 12.5 | 9 |
| 18 | 98 | 9 | 5.7 | 12.6 | 32 |
| 24 | 136 | 11 | 32.8 | 12.0 | 51 |
| 30 | 148 | 10 | 12.3 | 13.3 | 62 |
| 32 | 152 | 11 | 12.5 | 14.3 | 65 |
| 38 | 159 | 11 | 1.5 | 17.2 | 68 |

Similar results were obtained with an identical vitamin $B_{12}$ feed at twice the concentration or bolus additions of vitamin $B_{12}$ across the time course of the fermentation. The highest titer obtained was 77 g/L.

Improved Fermentation with KLP23/pAH48/pKP32:
A representative fermentation summary of the conversion of glucose to 1,3-propanediol (1,3-PD) using *E. coli* strain KLP23/pAH48/pKP32 is given in Table 5. Vitamin $B_{12}$ (0.150 g/L, 500 mL) was fed, starting 3 h after inoculation, at a rate of 16 mL/h. After 36 h, approximately 2 L of fermentation broth was purged in order to allow for the continued addition of glucose feed. The yield of 1,3-propanediol was 26 wt % (g 1,3-propanediol/g glucose consumed) and a titer of 112 g/L 1,3-propanediol was obtained.

TABLE 5

Representative fermentation summary of the improved conversion of glucose to 1,3-propanediol (1,3-PD) using *E. coli* strain KLP23/pAH48/pKP32

| Time (h) | OD550 (AU) | DO (%) | Glucose (g/L) | Glycerol (g/L) | 1,3-PD (g/L) |
|---|---|---|---|---|---|
| 0 | 0 | 148 | 12.8 | 0.0 | 0 |
| 6 | 22 | 84 | 6.9 | 3.3 | 0 |
| 12 | 34 | 90 | 9.7 | 10.4 | 7 |
| 18 | 66 | 43 | 9.3 | 5.9 | 24 |
| 24 | 161 | 9 | 0.2 | 2.5 | 46 |
| 30 | 200 | 10 | 0.2 | 6.0 | 67 |
| 36 | 212 | 10 | 1.2 | 9.7 | 88 |
| 42 | 202 | 2 | 0.1 | 15.5 | 98 |
| 48 | 197 | 12 | 1.2 | 23.8 | 112 |

Similar results were obtained with an identical vitamin $B_{12}$ feed at half the concentration or bolus additions of vitamin $B_{12}$ across the time course of the fermentation. The highest titer obtained was 114 g/L.

Example 8

Engineering of Triosephosphate Isomerase Mutant of *E. coli* KLP23 for Enhanced Yield of 1,3-propanediol from Glucose Construction of plasmid for triosephosphate isomerase gene replacement in *E. coli* KLP23:

*E. coli* KLP23 genomic DNA was prepared using the Puregene DNA Isolation Kit (Gentra Systems, Minneapolis, Minn.). A 1.0 kb DNA fragment containing cdh and the 3' end of triosephosphate isomerase (tpiA) genes was amplified by PCR (Mullis and Faloona, *Methods Enzymol.* 155, 335–350 (1987)) from KLP23 genomic DNA using primers SEQ ID NO:47 and SEQ ID NO:48. A 1.0 kb DNA fragment containing the 5' end of tpiA, yiiQ, and the 5' end of yiiR genes was amplified by PCR from KLP23 genomic DNA using primers SEQ ID NO:49 and SEQ ID NO:50. A ScaI site was incorporated into primer SEQ ID NO:49. The 5' end of primer SEQ ID NO:49 was the reverse complement of primer SEQ ID NO:48 to enable subsequent overlap extension PCR. The gene splicing by overlap extension technique (Horton et al., *BioTechniques* 8, 528–535 (1990)) was used to generate a 2.0 kb fragment by PCR using the above two PCR fragments as templates and primers SEQ ID NO:47 and SEQ ID NO:50. This fragment represented a deletion of 73% of the 768 bp tpiA structural gene. Overall, this fragment had 1.0 kb flanking regions on either side of the ScaI cloning site (within the partial tpiA) to allow for chromosomal gene replacement by homologous recombination.

The above blunt-ended 2.0 kb PCR fragment was cloned into the pCR-Blunt vector using the Zero Blunt PCR Cloning Kit (Invitrogen, San Diego, Calif.) to yield the 5.5 kb plasmid pRN106-2 containing kanamycin and Zeocin resistance genes. The 1.2 kb HincII fragment from pLoxCat1 (unpublished results), containing a chloramphenicol-resistance gene flanked by bacteriophage P1 loxP sites (Snaith et al., *Gene* 166, 173–174 (1995)), was used to interrupt the tpiA fragment in plasmid pRN106-2 by ligating it to ScaI-digested plasmid pRN106-2 to yield the 6.8 kb plasmid pRN107-1.

Engineering of Triosephosphate Isomerase Mutant RJ8m by Linear DNA Transformation:

Using pRN107-1 as template and primers SEQ ID NO:47 and SEQ ID NO:50, the 3.2 kb fragment containing tpiA flanking regions and the loxP-CmR-loxP cassette was PCR amplified and gel-extracted. *E. coli* KLP23 was electrotransformed with up to 1 µg of this 3.2 kb linear DNA fragment and transformants that were chloramphenicol-resistant (12.5 µg/mL) and kanamycin-sensitive (30 µg/mL) were further screened on M9 minimal media for poor glucose utilization on 1 mM glucose, for normal gluconate utilization on 1 mM gluconate, and to ensure the glycerol non-utilization phenotype of host KLP23 on 1 mM glycerol. An EcoRI digest of genomic DNA from one such mutant, RJ8m, when probed with the intact tpiA gene via Southern analysis (Southern, *J. Mol. Biol.* 98, 503–517 (1975)) indicated that it was a double-crossover integrant (tpiA gene replacement) since the two expected 6.6 kb and 3.0 kb bands were observed, owing to the presence of an additional EcoRI site within the chloramphenicol resistance gene. As expected, the host KLP23 and wild-type FM5 controls yielded single 8.9 kb and 9.4 kb bands respectively. This tpiA mutant was further analyzed by genomic PCR using primers SEQ ID NO:51 and SEQ ID NO:52, which yielded the expected 4.6 kb PCR fragment while for the same primer pair the host KLP23 and wild-type FM5 strains both yielded the expected 3.9 kb PCR fragment. When cell-free extracts from tpiA mutant RJ8m and host KLP23 were tested for tpiA activity using glyceraldehyde 3-phosphate as substrate, no activity was observed with RJ8m. The tpiA mutant RJ8m was electrotransformed with plasmid pAH48 to allow glycerol production from glucose and also with both plasmids pAH48 and pDT29 or pKP32 to allow 1,3-propanediol production from glucose. The chloramphenicol resistance marker was eliminated from RJ8m to give RJ8.

Example 9

Conversion of Glucose to 1,3-propanediol Using *E. coli* Strain RJ8/pAH48/pDT29 and the Improved Process Using RJ8/pAH48/pKP32

Pre-Culture:

RJ8/pAH48/pDT29 and RJ8/pAH48/pKP32 were pre-cultured for seeding a fermenter as described in Example 7. RJ8/pAH48/pKP32 is identical to RJ8/pAH48/pDT29 except that dhaT is deleted.

Fermenter Medium:

Fermenter medium was as described in Example 7.

Fermentation Growth:

Fermenter growth was as described in Example 7 except that initial values for air flow rate (set to minimum values of between 5 and 6 standard liters per min) and agitator speed (set to minimum values of between 300 and 690 rpm) were set so that dissolved oxygen (DO) control was initiated when OUR values reached between 60 and 100 mmol/L/h. Vitamin $B_{12}$ or coenzyme $B_{12}$ was added as noted below.

Fermentation with RJ8/pAH48/pDT29:

A representative fermentation summary of the conversion of glucose to 1,3-propanediol (1,3-PD) using *E. coli* strain RJ8/pAH48/pDT29 is given in Table 6. Vitamin $B_{12}$ was provided as bolus additions of 2, 16 and 16 mg at 2, 8, and 26 h, respectively. The yield of 1,3-propanediol was 35 wt % (g 1,3-propanediol/g glucose consumed) and a titer of 50.1 g/L 1,3-propanediol was obtained.

TABLE 6

Representative fermentation summary of the conversion of glucose to 1,3-propanediol (1,3-PD) using *E. coli* strain RJ8/pAH48/pDT29

| Time (h) | OD550 (AU) | DO (%) | Glucose (g/L) | Glycerol (g/L) | 1,3-PD (g/L) |
| --- | --- | --- | --- | --- | --- |
| 0 | 0 | 140 | 10.6 | 0.1 | 0.0 |
| 6 | 5 | 107 | 11.1 | 0.5 | 0.4 |
| 10 | 16 | 90 | 8.5 | 1.7 | 1.3 |
| 14 | 25 | 86 | 1.8 | 2.4 | 5.9 |
| 19 | 38 | 53 | 3.5 | 5.9 | 15.4 |
| 25 | 53 | 38 | 0.1 | 9.2 | 26.7 |
| 31 | 54 | 10 | 4.5 | 7.4 | 39.0 |
| 37 | 37 | 23 | 17.2 | 6.0 | 45.0 |
| 43 | 21 | 13 | 9.9 | 7.7 | 50.1 |

Improved Fermentation with RJ8/pAH48/pKP32:

A representative fermentation summary of the conversion of glucose to 1,3-propanediol (1,3-PD) using *E. coli* strain RJ8/pAH48/pKP32 is given in Table 7. Vitamin $B_{12}$ was provided as bolus additions of 48 and 16 mg at approximately 26 and 44 hr, respectively. The yield of 1,3-propanediol was 34 wt % (g 1,3-propanediol/g glucose consumed) and a titer of 129 g/L 1,3-propanediol was obtained.

TABLE 7

Representative fermentation summary of the improved conversion of glucose to 1,3-propanediol (1,3-PD) using E. coli strain RJ8/pAH48/pKP32.

| Time (h) | OD550 (AU) | DO (%) | Glucose (g/L) | Glycerol (g/L) | 1,3-PD (g/L) |
|---|---|---|---|---|---|
| 0 | 0 | 150 | 12.6 | 0.1 | 0 |
| 6 | 12 | 113 | 6.0 | 2.6 | 0 |
| 12 | 24 | 99 | 0.0 | 10.6 | 0 |
| 18 | 51 | 76 | 2.4 | 28.9 | 0 |
| 24 | 78 | 82 | 2.4 | 44.2 | 5 |
| 30 | 114 | 70 | 3.8 | 26.9 | 33 |
| 36 | 111 | 72 | 0.0 | 20.0 | 57 |
| 42 | 139 | 65 | 0.1 | 21.9 | 69 |
| 48 | 157 | 36 | 0.1 | 22.4 | 79 |
| 55 | 158 | 25 | 0.2 | 21.4 | 94 |
| 64 | 169 | 14 | 0.1 | 15.8 | 113 |
| 72 | 169 | 12 | 0.1 | 13.4 | 119 |
| 74 | 162 | 14 | 0.1 | 14.8 | 129 |

Example 10

Identification of the E. coli Non-Specific Catalytic Activity (yqhD) in the Improved 1,3-propanediol Process Demonstration of Non-specific Catalytic Activity in 1,3-propanediol-producing Fermentations with the Improved Catalyst:

A whole cell assay for 1,3-propanediol dehydrogenase activity was used to demonstrate that the non-specific catalytic activity in E. coli is present under fermentative conditions after the addition of vitamin $B_{12}$ and the production of 3-hydroxypropionaldehyde (3-HPA), but not before. A recombinant E. coli strain containing the glycerol-production and 1,3-propanediol-production plasmids, pAH48 and pKP32, respectively, was grown in 10 L fermenters, essentially as described in Example 7, but in the absence of vitamin $B_{12}$. A vitamin $B_{12}$ bolus (48 mg) was added when the tanks reached approximately 100 $OD_{550}$. Aliquots of cells were taken from the tanks immediately before and 2 h post-vitamin $B_{12}$ addition. The cells were recovered by centrifugation and resuspended to their original volume in PBS buffer containing 150 µg/mL chloramphenicol to inhibit new protein synthesis. An appropriate volume of the chloramphenicol treated cells was added to 250 mL baffled flasks containing a reaction mixture (PBS buffer containing 10 g/L glucose, 10 g/L glycerol, 1 mg/L coenzyme $B_{12}$, and 150 µg/mL chloramphenicol) so that the final volume was 50 mL at an $OD_{550}$ of approximately 10. The flasks, protected from light, were shaken at 250 rpm at 35° C. Aliquots for HPLC analysis were taken over time. Time-dependent production of 3-HPA was observed in flasks containing cells recovered from the fermenter either pre- or post-vitamin $B_{12}$ addition. In direct contrast, significant levels of 1,3-propanediol were observed only in those flasks containing cells recovered from the fermenter post-vitamin $B_{12}$ addition.

Detection of Non-Specific Catalytic Activity in Cell-Free Extracts:

A native gel activity stain assay was used to demonstrate non-specific catalytic activity in cell-free extracts. Cells were recovered, pre- and post-vitamin $B_{12}$ addition, from representative 10-L fermentations employing recombinant E. coli strains containing the glycerol-production and 1,3-propanediol-production plasmids, pAH48 and pKP32, respectively; and cell-free extracts were prepared by cell disruption using a French press. The cell-free extracts, a preparation of pure Klebsiella pneumoniae 1,3-propanediol dehydrogenase (dhaT), and molecular weight standards were applied to and run out on native gradient polyacrylamide gels. The gels were then exposed to either the substrates 1,3-propanediol and $NAD^+$ or ethanol and $NAD^+$. As expected in the gels where 1,3-propanediol was the substrate, an activity stain for DhaT was observed which migrated on the native gel at approximately 340 Kdal. This activity was observed only in lanes where pure Klebsiella pneumoniae 1,3-propanediol dehydrogenase was applied. In contrast, where 1,3-propanediol was the substrate and post-vitamin $B_{12}$ cell-free extracts were applied, a non-specific catalytic activity was observed at approximately 90 Kdal. When ethanol was used as a substrate, neither the DhaT band nor the non-specific catalytic activity band were visible, but a separate band was found pre- and post-vitamin $B_{12}$ addition at approximately 120 Kdal. This new band most likely represents an alcohol dehydrogenase with specificity towards ethanol as substrate as is typically found in all organisms.

This native gel assay, where proteins are separated by molecular weight prior to the enzymatic assay step, offered greater sensitivity and accuracy in measuring the reduction of 1,3-propanediol in those constructs with low activity and where the activity is likely to be distinct from the alcohol dehydrogenases with specificity towards ethanol as substrate that have been well characterized for E. coli and found in all organisms. The dehydrogenase assay works on the principle that dehydrogenase catalyzes the transfer of electrons from 1,3-propanediol (or other alcohols) to $NAD^+$. PMS (phenazine methosulfate) then couples electron transfer between NADH and a tetrazolium bromide dye (MTT, 3-[4,5-dimethylthiazol-2-yl]-2,5-diphenyltetrazolium bromide) which forms a precipitate in the gel. After a few hours to overnight soaking in the substrates, the gels are washed to remove reagents and soluble dye. At bands on the gel where there is an active dehydrogenase, an insoluble blue dye forms. Various aspects of the assay have been described by Johnson and Lin (J. Bacteriol. 169:2050 (1987)).

Figure 6:
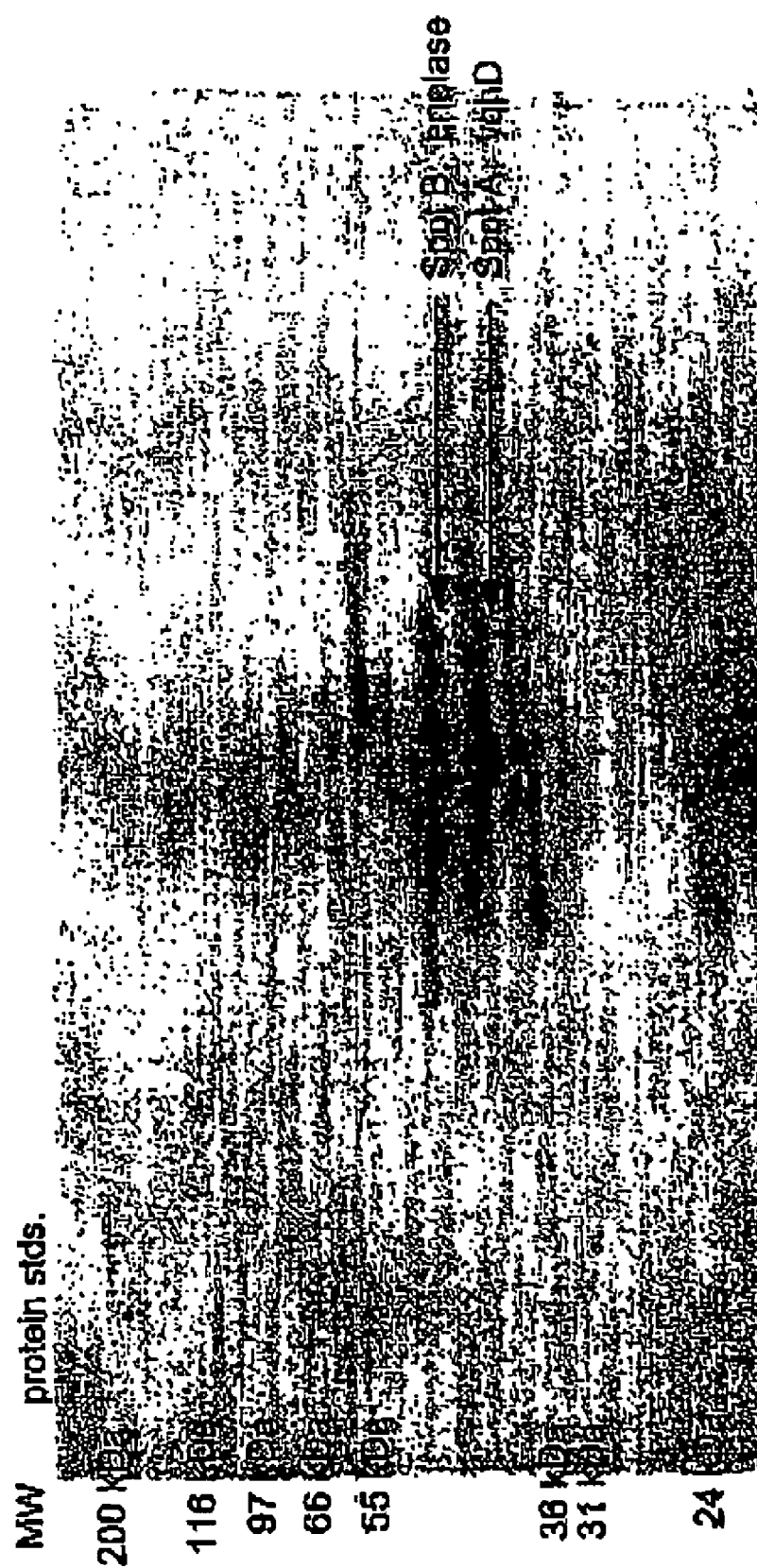
FIG. 6 is a 2D-PAGE membrane blot with the soluble protein fraction extracted from a band showing endogenous E. coli oxidoreductase activity (non-specific catalytic activity) on a native gel.

Purification and Identification of the Non-Specific Catalytic Activity in E. coli:

A large scale, partial purification of non-specific catalytic activity was performed on cells harvested from the end of a typical 1,3-propanediol production run as described in the improved process using KLP23/pAH48/pKP32 of Example 7. The cell pellet (16 g) was washed and resuspended three times in 20 mL of 50 mM Hepes buffer, pH 7.5. The cells in the suspension were lysed by sonication. The cell-free extract was obtained by centrifugation (15 min, 20,000×g, 10° C.) and the supernatant was further clarified by addition of 250 mg of protamine sulfate with stirring on ice. The supernatant obtained by centrifugation (20 min, 20,000×g, 10° C.) was fractionated by passage through a Superdex® 200 preparative grade column (6×60 cm) equilibrated with Hepes buffer. Fractions of 10 mL each were collected and an aliquot of each was concentrated twentyfive-fold using 10,000 MW cutoff Centricon® membranes prior to assay by the native gel activity stain. The non-specific catalytic activity was identified in fractions 107–112, and the peak activity in fractions 108–109. A larger aliquot (7 mL each) of fractions 108 and 109 were concentrated fifty-fold and loaded on all lanes of a 12-lane native gel. The gel was cut in half and one half was stained for dehydrogenase activity where a dark blue band appeared that represented the non-specific catalytic activity. The unstained gel was aligned top to bottom with the stained gel and a band was cut on the unstained gel that corresponded to the band of non-specific catalytic activity. The gel strip was pulverized and soluble protein was extracted by immersing the pulverized particles in 0.5 mL of 2D-loading buffer, heating to 95° C. for 5 min, and centrifugation to remove the gel particles. The supernatant was loaded onto an isoelectricfocusing (IEF) strip for 2-dimension polyacrylamide gel electrophoresis (2D-PAGE) using conditions described for 2D-PAGE of *E. coli* extracts in the Swiss 2D database (http://www.expasy.ch/ch2d/; Tonella et al. *Electrophoresis* 19:1960–1971 (1998)). The gel was transferred to a PVDF membrane by electroblotting. The membrane was stained for proteins using the Colloidal blue gel stain. The stained blot used to obtain the identity of the non-specific catalytic activity is shown in FIG. 6. Spots were identified using standard techniques for amino terminus peptide sequencing. Only a single spot (Spot A) encoded for an oxidoreductase activity. Nineteen cycles of Spot A (FIG. 6) yielded a 100% identity match by the FASTA search tool with the amino-terminus of yqhD, an *E. coli* open reading frame with putative oxidoreductase activity. Complete amino acid sequence for the protein encoded by yqhD is given in SEQ ID NO:57; the corresponding DNA sequence is given in SED ID NO:58. They qhD gene has 40% identity to the gene adhB in *Clostridium*, a probable NADH-dependent butanol dehydrogenase 2.

Gene Disruption of yqhD in *E. coli* KLP23:

Biochemical assays and amino-terminal amino acid sequencing suggested that non-specific catalytic activity may be encoded by the *E. coli* yqhD gene. This gene of unknown function encodes a hypothetical oxidoreductase and contains two alcohol dehydrogenase signatures also found in the *Citrobacter freundii* and *Klebsiella pneumoniae* 1,3-propanediol dehydrogenase encoded by the dhaT gene.

To disrupt this gene, yqhD and 830 bp of 5'-flanking DNA sequence and 906 bp of 3'-flanking DNA sequence were amplified from *E. coli* KLP23 (Example 4) genomic DNA in a PCR using Taq polymerase and the following primers:
(SEQ ID NO:59) 5'-GCGGTACCGTTGCTCGACGCT-CAGGTTTTCGG-3'
(SEQ ID NO:60) 5'-GCGAGCTCGACGCTTGCCCT-GATCGAGTTTTGC-3' The reaction was run at 94° C. for 1 min, 50° C. for 1 min, and 72° C. for 3 min for 35 cycles followed by a final extension at 72° C. for 5 min. The resulting 3.7 Kb DNA fragment was purified, digested with SacI and KpnI and ligated to similarly digested pBluescriptII KS(+) (Strategene) for 16 h at 16° C. The ligated DNA was used to transform *E. coli* DH5α (Gibco/BRL) and the expected plasmid, pJSP29, was isolated from a transformant demonstrating white colony color on LB agar (Difco) containing X-gal (40 µg/mL) and ampicillin (100 µg/mL). Plasmid pJSP29 was digested with AflII and NdeI to liberate a 409 bp DNA fragment comprising 363 bp of the yqhD gene and 46 bp of 3'-flanking DNA sequence. The remaining 5,350 bp DNA fragment was purified and ligated to the 1,374 bp AflII/NdeI DNA fragment containing the kanamycin resistance gene from pLoxKan2 (Genencor International, Palo Alto, Calif.) for 16 h at 16° C. The ligated DNA was used to transform *E. coli* DH5α and the expected plasmid, pJSP32-Blue, was isolated from a transformant selected on LB agar media containing kanamycin (50 µg/mL). Plasmid pJSP32-Blue was digested with KpnI and SacI and the 3,865 bp yqhD disruption cassette was purified and ligated to similarly digested pGP704 (Miller and Mekalanos, *J. Bacteriol.* 170:2575–2583 (1988)) for 16 h at 16° C. The ligated DNA was used to transform *E. coli* SY327 (Miller and Mekalanos, *J. Bacteriol.* 170:2575–2583 (1988)) and the expected plasmid, pJSP32, was isolated from a transformant selected on LB agar media containing kanamycin (50 µg/mL). Plasmid pJSP32 was transformed into *E. coli* KLP23 and transformants were selected on LB agar containing kanamycin (50 µg/mL). Of the 200 kanamycin-resistant transformants screened, two demonstrated the ampicillin-sensitive phenotype expected for a double-crossover recombination event resulting in replacement of the yqhD gene with the yqhD disruption cassette.

The disruption of the yqhD gene was confirmed by PCR using genomic DNA isolated from these two transformants as the template and the following sets of primer pairs:

Set #1:
(SEQ ID NO:61) 5'-GCGAGCTCGACGCTTGCCCT-GATCGAGTTTTGC-3'
(SEQ ID NO:62) 5'-CAGCTGGCAATTCCGGTTCG-3'

Set #2:
(SEQ ID NO:63) 5'-CCCAGCTGGCAATTCCGGT-TCGCTTGCTGT-3'
(SEQ ID NO:64) 5'-GGCGACCCGACGCTCCAGACG-GAAGCTGGT-3'

Set #3:
(SEQ ID NO:65) 5'-CCGCAAGATTCACGGATG-CATCGTGAAGGG-3'
(SEQ ID NO:66) 5'-CGCCTTCTTGACGAGTTCT-GAGCGGGA-3'

Set #4:
(SEQ ID NO:67) 5'-GGAATTCATGAACAACTTTAATCT-GCACAC-3'
(SEQ ID NO:68) 5'-GTTTGAGGCGTAAAAAGCT-TAGCGGGCGGC-3'

The reactions were run using either Expand High Fidelity Polymerase (Boehringer Manheim) or Platinum PCR Supermix containing Taq polymerase (Gibco/BRL) at 94° C. for 1 min, 50° C. for 1 min, and 72° C. for 2 min for 35 cycles followed by final extension at 72° C. for 5 min. The resulting PCR products were analyzed by gel electrophoresis in 1.0% (w/v) agarose. The results summarized in Table 8 confirmed disruption of the yqhD gene in both transformants.

TABLE 8

| Primer Set | Expected Size (bp) | | Observed Size (bp) |
|---|---|---|---|
| | yqhD disruption | yqhD wild-type | |
| 1 | 1,200 | no product | ~1,200 |
| 2 | 1,266 | no product | ~1,266 |
| 3 | 2,594 | no product | ~2,594 |
| 4 | no product | 1,189 | ~900 |

The yqhD disruption deletes the 3' end of yqhD, including 46 bp of 3'-flanking intergenic DNA sequence. The deletion removes 363 bp of 3' yqhD coding sequence corresponding to 121 amino acids. A stop codon is present 15 bp downstream of the remaining yqhD coding sequence in the kanamycin resistance cassette.

Plasmids pAH48 and pKP32 were co-transformed into *E. coli* KLP23 (yqhD⁻) and transformants containing both plasmids were selected on LB agar containing ampicillin (100 μg/mL) and spectinomycin (50 μg/mL). A representative transformant was tested for its ability to covert glucose to 1,3-propanediol in 10 L fermentations either in the presence or absence of vitamin $B_{12}$.

Demonstration that yqhD is Required for Significant 1,3-propanediol Production in *E. coli* Strain KLP23/pAH48/pKP32:

Fermentations for the production of 1,3-propanediol were performed, essentially as described in Example 7, with the *E. coli* strain KLP23 (yqhD⁻)/pAH48/pKP32 in order to test for the effect of the yqhD disruption on 1,3-propanediol production.

A representative 10-L fermentation using the knockout of the non-specific catalytic activity, *E. coli* strain KLP23 (yqhD⁻)/pAH48/pKP32, is shown in Table 9. The organism steadily accumulated cell mass and glycerol until the addition of vitamin $B_{12}$ when the $OD_{550}$ exceeded 30 A (10.4 h). Vitamin $B_{12}$ was added as a bolus addition of 8 mg at 10.4 h and thereafter vitamin B 12 was continuously fed at a rate of 1.32 mg/h. In the 4 h that followed $B_{12}$ addition, glucose consumption slowed, the oxygen utilization rate dropped and there was no further increase in optical density. Fermentation of glucose ceased and the glucose concentration in the tank accumulated. The highest titer of 1,3-propanediol obtained was 0.41 g/L. The organism was checked for its viability by plating a dilution series of the cells on agar plates containing ampicillin and spectinomycin. The plates were incubated for 24 h in a 30° C. incubator. There were no viable colonies on the plate from the fermentation of *E. coli* KLP23 (yqhD⁻)/pAH48/pKP32, Table 11.

By contrast, the cell suspension from a control tank to which no vitamin $B_{12}$ was added continued to accrue cell mass and glycerol until the 10-L tank was full due to the complete addition of the glucose feed solution (Table 10). An agar plate viability determination by dilution series of the cell suspension at the end of this fermentation showed a viable cell count that was consistent with the total cell number estimated by the optical density value (Table 11).

TABLE 9

Representative fermentation summary of the failed conversion of glucose to 1,3-propanediol (1,3-PD) using *E. coli* strain KLP23 (yqhD-)/pAH48/pKP32.

| time (h) | OD550 (AU) | DO (%) | glucose (g/L) | glycerol (g/L) | 1,3-PD (g/L) |
|---|---|---|---|---|---|
| 0 | 0.4 | 150 | 11.3 | 0.05 | 0 |
| 2.3 | 3.0 | 134 | 10.7 | 0.13 | 0 |
| 4.3 | 10.8 | 85.0 | 8.2 | 1.41 | 0 |
| 8.3 | 23.1 | 81.8 | 0.9 | 10.0 | 0 |
| 16.3 | 37.2 | 149 | 13.1 | 21.4 | 0.41 |
| 18.3 | 47.6 | 149 | 18.9 | 21.6 | 0.39 |
| 20.3 | 39.6 | 149 | 24.4 | 22.3 | 0.42 |
| 23.8 | 33.6 | 149 | 25.4 | 22.0 | 0.41 |

TABLE 10

Representative fermentation summary of the conversion of glucose to glycerol using *E. coli* strain KLP23 (yqhD-)/pAH48/pKP32.

| Time (h) | $OD_{550}$ (AU) | DO (%) | glucose (g/L) | glycerol (g/L) |
|---|---|---|---|---|
| 0 | 0.2 | 148 | 9.5 | 0.06 |
| 2.2 | 2.8 | 128 | 8.9 | 0.13 |
| 4.2 | 10.4 | 58.5 | 7.0 | 1.4 |
| 8.2 | 21.6 | 57.6 | 2.7 | 11.2 |
| 16.2 | 76.8 | 10.7 | 0 | 40.5 |
| 20.2 | 117 | 10.2 | 0 | 52.9 |
| 23.7 | 154 | 8.5 | 0 | 63.9 |
| 36.2 | 239 | 10.1 | 0.1 | 122 |

TABLE 11

Representative summary of viability plate counts from endpoints of fermentations of glucose using *E. coli* strain KLP23 (yqhD-)/pAH48/pKP32 in the absence and presence of vitamin $B_{12}$.

| vitamin $B_{12}$ | time (h) at endpoint | $OD_{550}$ (AU) | viable counts (cfu/mL) |
|---|---|---|---|
| no | 36.2 | 239 | 2.1E11 |
| yes | 23.8 | 33.6 | 0 |
| yes | 23.8 | 41.2 | 0 |

What is claimed is:

1. A microorganism transformed with a chimeric gene comprising an isolated nucleic acid fragment encoding a polypeptide with non-specific catalytic activity for the conversion of 3-hydroxypropionaldehyde to 1,3-propanediol operably linked to suitable regulatory sequences, wherein the isolated nucleic acid fragment is selected from the group consisting of:

(a) an isolated nucleic acid fragment encoding the amino acid sequence of SEQ ID NO:57;

(b) an isolated nucleic acid fragment encoding a polypeptide of at least 387 amino acids having at least 95% identity with the amino acid sequence of SEQ ID NO:57;

(c) an isolated nucleic acid fragment that hybridizes with (a) or (b) under hybridization conditions of 0.1×SSC, 0.1% SDS, 65° C. and washed with 2×SSC, 0.1% SDS followed by 0.1×SSC, 0.1% SDS; and (d) an isolated nucleic acid fragment that is complementary to (a), (b) or (c);

wherein the transformed microorganism is further transformed with genes encoding a glycerol or diol dehydratase enzyme, and is selected from the group consisting of *Citrobacter, Enterobacter, Clostridium, Kiebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Salmonella, Bacillus, Streptomyces, Escherichia,* and *Pseudomonas*.

* * * * *